United States Patent
Kugimiya et al.

(10) Patent No.: US 11,638,717 B2
(45) Date of Patent: May 2, 2023

(54) COMPLEX OF NUCLEIC ACID MEDICINE AND MULTIBRANCHED LIPID

(71) Applicant: SHIONOGI & CO., LTD., Osaka (JP)

(72) Inventors: Akira Kugimiya, Toyonaka (JP); Mitsuaki Sekiguchi, Amagasaki (JP); Norikazu Kuroda, Toyonaka (JP); Jun Nakamura, Toyonaka (JP); Tetsuya Tanino, Toyonaka (JP); Yasunori Mitsuoka, Toyonaka (JP); Takeshi Kasuya, Osaka (JP); Yasuharu Kato, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 358 days.

(21) Appl. No.: 16/497,323

(22) PCT Filed: Mar. 28, 2018

(86) PCT No.: PCT/JP2018/012649
§ 371 (c)(1),
(2) Date: Sep. 24, 2019

(87) PCT Pub. No.: WO2018/181428
PCT Pub. Date: Oct. 4, 2018

(65) Prior Publication Data
US 2020/0384010 A1 Dec. 10, 2020

(30) Foreign Application Priority Data
Mar. 29, 2017 (JP) .............................. JP2017-064336

(51) Int. Cl.
*A61K 31/7088* (2006.01)
*A61K 47/50* (2017.01)
*C12N 15/113* (2010.01)

(52) U.S. Cl.
CPC .......... *A61K 31/7088* (2013.01); *A61K 47/50* (2017.08); *C12N 15/113* (2013.01)

(58) Field of Classification Search
CPC ...... A61K 9/107; A61K 9/127; A61K 9/1075; A61K 9/1271; C12N 15/113; C12N 2310/14; C12N 2320/32
USPC ....... 424/9.1; 435/6.1, 23, 1, 24.5, 455, 458; 536/23.1, 24.5
See application file for complete search history.

(56) References Cited

U.S. PATENT DOCUMENTS

| | | | |
|---|---|---|---|
| 5,512,671 | A | 4/1996 | Piantadosi et al. |
| 2009/0239814 | A1 | 9/2009 | Manoharan et al. |
| 2012/0142765 | A1 | 6/2012 | Jimenez et al. |
| 2013/0178541 | A1 | 7/2013 | Stanton et al. |
| 2013/0202652 | A1 | 8/2013 | Manoharan et al. |
| 2015/0018540 | A1 | 1/2015 | Prakash et al. |
| 2015/0197746 | A1 | 7/2015 | Rajeev et al. |
| 2016/0159834 | A1 | 6/2016 | Lee et al. |
| 2018/0264105 | A1 | 9/2018 | Kugimiya et al. |

FOREIGN PATENT DOCUMENTS

| | | | |
|---|---|---|---|
| EP | 2 229 186 A2 | 9/2010 | |
| EP | 2 264 167 A1 | 12/2010 | |
| EP | 2 618 847 A2 | 7/2013 | |
| EP | 2 751 270 A1 | 7/2014 | |
| JP | WO 2009/123185 A1 | 10/2009 | |
| JP | 2011-505425 A | 2/2011 | |
| JP | 2014-500233 A | 1/2014 | |
| JP | WO 2017/057540 A1 | 4/2017 | |
| WO | WO 2009/126933 A2 | 10/2009 | |
| WO | WO 2010/150004 A1 | 12/2010 | |
| WO | WO 2012/016188 A2 | 2/2012 | |
| WO | WO 2012/037254 A1 | 3/2012 | |
| WO | WO 2013/089283 A1 | 6/2013 | |
| WO | WO 2014/022739 A2 | 2/2014 | |
| WO | WO 2015/012912 A2 | 1/2015 | |
| WO | WO-2015012912 A2 * | 1/2015 | ............... A61K 9/14 |
| WO | WO 2015/0105083 A1 | 7/2015 | |
| WO | WO-2017057540 A1 * | 4/2017 | ........... A61K 31/713 |

OTHER PUBLICATIONS

Spelios et al (Biochemistry, vol. 49, No. 27, pp. 5753-5759 (2010)) (Year: 2010).*
Structure attachments Kugimiya, Spelios.*
International Search Report dated Jul. 3, 2018 in PCT/JP2018/012649 filed on Mar. 28, 2018.
Spelios, M. et al., "Effect of spacer attachment sites and pH-sensitive headgroup expansion on cationic lipid-mediated gene delivery of three novel myristoyl derivatives", Biophysical Chemistry, vol. 129, 2007, pp. 137-147.
Wolfrum, C. et al., "Mechanismsand optimization of in vivo delivery of lipophilic siRNAs", Nature Biotechnology, vol. 25, No. 10, 2007, pp. 1149-1157.
Ueno, Y. et al., "Synthesis and silencing properties of siRNAs possessing lipophilic groups at their 3'-termini", Bioorganic & Medicinal Chemistry, vol. 16, 2008, pp. 7698-7704.
Suzuki, Y. et al., "siRNA-lipid nanoparticles with long-term storage stability facilitate potent gene-silencing in vivo", Journal of Controlled Release, vol. 220, 2015, pp. 44-50.
Nikan, M. et al., "Synthesis and Evaluation of Parenchymal Retention and Efficacy of a Metabolically Stable O-Phosphocholine-N-docosahexaenoyl-L-serine siRNA Conjugate in Mouse Brain", Bioconjugate Chemistry, vol. 28, 2017, pp. 1758-1766.
Nikan, M. et al., "Docosahexaenoic Acid Conjugation Enhances Distribution and Safety of siRNA upon Local Administration in Mouse Brain", Molecular Therapy—Nucleic Acids, vol. 5, 2016, pp. 1-11.

(Continued)

*Primary Examiner* — Jane J Zara
(74) *Attorney, Agent, or Firm* — Oblon, McClelland, Maier & Neustadt, L.L.P.

(57) ABSTRACT

The purpose of the present invention is to provide novel complexes that improve the effect of nucleic acid medicines. Provided is a complex in which a multibranched lipid(s) binds through a linker to a strand of an oligonucleotide comprising a nucleic acid medicine having suppressing activity of the target gene expression.

20 Claims, No Drawings
Specification includes a Sequence Listing.

(56) References Cited

OTHER PUBLICATIONS

Osborn, M. F. et al., "Hydrophobicity drives the systemic distribution of lipid-conjugated siRNAs via lipid transport pathways", Nucleic Acids Research, vol. 47, No. 3, 2019, pp. 1070-1081.

Japanese Office Action dated Mar. 15, 2022 in Japanese Patent Application No. 2019-509946, 4 pages.

Tao Chen, et al., "DNA Micelle Flares for Intracellular mRNA Imaging and Gene Therapy," Angew. Chem. Int. Ed., vol. 52, 2013, pp. 2012-2016.

Extended European Search Report dated Dec. 1, 2020 in European Patent Application No. 18 775 491.6, 7 pages.

\* cited by examiner

SEQUENCE LISTING

<160> NUMBER OF SEQ ID NOS: 15

<210> SEQ ID NO 1
<211> LENGTH: 19
<212> TYPE: RNA
<213> ORGANISM: Artificial sequence
<220> FEATURE:
<223> OTHER INFORMATION: Antisense oligonucleotide of Hprt1 siRNA

<400> SEQUENCE: 1
uuaaaguuga gagaucauc                                                    19

<210> SEQ ID NO 2
<211> LENGTH: 19
<212> TYPE: RNA
<213> ORGANISM: Artificial sequence
<220> FEATURE:
<223> OTHER INFORMATION: Sense oligonucleotide of Hprt1 siRNA

<400> SEQUENCE: 2
gaugaucucu caacuuuaa                                                    19

<210> SEQ ID NO 3
<211> LENGTH: 21
<212> TYPE: RNA
<213> ORGANISM: Artificial sequence
<220> FEATURE:
<223> OTHER INFORMATION: Antisense oligonucleotide of Luc siRNA

<400> SEQUENCE: 3
guaggaguag ugaaaggcca g                                                 21

<210> SEQ ID NO 4
<211> LENGTH: 21
<212> TYPE: RNA
<213> ORGANISM: Artificial sequence
<220> FEATURE:
<223> OTHER INFORMATION: Sense oligonucleotide of Luc siRNA

<400> SEQUENCE: 4
ggccuuucac uacuccuacg a                                                 21

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5
ctaccctctg gtagattgtc g                                                 21

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
tcgagagctt cagactcgtc ta                                                22

<210> SEQ ID NO 7
<211> LENGTH: 20
<212> TYPE: DNA
<213> ORGANISM: Artificial sequence

```
<220> FEATURE:
<223> OTHER INFORMATION: Primer

<400> SEQUENCE: 7
gcaccgtcaa ggctgagaac                                               20

<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8
tggtgaagac gccagtgga                                                19

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
ttgttgttgg atatgccctt gacta                                         25

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
aggcagatgg ccacaggact a                                             21

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
tgtgtccgtc gtggatctga                                               20

<210> SEQ ID NO 12
<211> LENGTH: 21
<212> TYPE: DNA
<213> ORGANISM: Artificial sequence
<220> FEATURE:
<223> OTHER INFORMATION: Primer

<400> SEQUENCE: 12
ttgctgttga agtcgcagga g                                             21

<210> SEQ ID NO 13
<211> LENGTH: 16
<212> TYPE: RNA
<213> ORGANISM: Artificial sequence
<220> FEATURE:
<223> OTHER INFORMATION: Sense oligonucleotide of Hprt1 siRNA

<400> SEQUENCE: 13
gaucucucaa cuuuaa                                                   16
```

```
<210> SEQ ID NO 14
<211> LENGTH: 5
<212> TYPE: PRT
<213> ORGANISM: Artificial sequence
<220> FEATURE:
<223> OTHER INFORMATION: Amino acid linker

<400> SEQUENCE: 14

Trp Cys Ala Ala Lys
1               5

<210> SEQ ID NO 15
<211> LENGTH: 5
<212> TYPE: PRT
<213> ORGANISM: Artificial sequence
<220> FEATURE:
<223> OTHER INFORMATION: Amino acid linker

<400> SEQUENCE: 15

Trp Cys Lys Val Lys
1               5
```

COMPLEX OF NUCLEIC ACID MEDICINE AND MULTIBRANCHED LIPID

FIELD OF THE INVENTION

The present invention relates to a complex of a nucleic acid medicine having suppressing activity of the target gene expression and a multibranched lipid(s). More particularly, it relates to a complex in which a multibranched lipid(s) binds to an oligonucleotide having suppressing activity of the target gene expression through a linker (hereinafter referred to as "the complex of the present invention").

BACKGROUND ART

Nucleic acid medicines targeting mRNA include antisense oligonucleotides, siRNA, microRNAs (hereinafter referred to as "miRNA") and the like.

An antisense oligonucleotide is an oligonucleotide complementary to mRNA, mRNA precursor or ncRNA (non-coding RNA) such as ribosomal RNA, transfer RNA, miRNA and the like, of the target gene, and a single-stranded DNA, RNA and/or structural analog thereof which consists of about 8 to 30 bases. The antisense oligonucleotide suppresses the function of mRNA, mRNA precursor or ncRNA by forming a double strand with the target mRNA, mRNA precursor or ncRNA.

A siRNA is a low molecular weight double-strand RNA complementary to the target gene which consists of about 19 to 25 base pairs. A siRNA is incorporated into a protein called RISC to be a single-stranded siRNA (guide strand), and then the more unstable single strand (passenger strand) is degraded. The guide strand binds to mRNA of the target gene having a complementary base sequence and then suppresses the gene expression by base sequence-specific mRNA degradation.

miRNA is an endogenous, non-coding RNA of about 20 to 25 bases encoded on the genome. miRNA is transcribed from a miRNA gene on the genomic DNA first as a primary transcript (Primary miRNA, Pri-miRNA) having a length of about several hundred to several thousand bases, and then processed into a pre-miRNA (precursor miRNA) having a hairpin structure of about 60 to 110 bases. Thereafter, it moves from the nucleus into the cytoplasm and is further spliced into a double-stranded miRNA of about 20 to 25 bases. The double-stranded miRNA is incorporated into a protein called RISC to be a single-stranded miRNA (guide strand), and then the more unstable single strand (passenger strand) is degraded. The single-stranded miRNA binds to mRNA of the target gene having a partially complementary base sequence and inhibit translation of the target gene.

However, these nucleic acid medicines are easily degraded by nucleases in vivo, and the efficiency of incorporation into target cells is low. So, it is difficult to put them into practical use. To overcome two major problems, the chemical modification of the nucleic acid itself, which is the active ingredient, and the drug delivery system (DDS) that delivers the nucleic acids into the target cells have been studied for many years.

Examples of chemical modifications of nucleic acids themselves are S-oligos (phosphorothioates) in which the phosphoric acid part is modified, 2',4'-BNA (bridged nucleic acid)/LNA (locked nucleic acid) in which the sugar moiety is modified, and the like (see Patent Documents 1 to 5).

Examples of DDSs include methods using carriers such as cationic liposomes and polymeric micelles, and methods of adding peptides, sugars or hydrophobic molecules such as cholesterols to nucleic acids. For example, Non-Patent Documents 1 and 2 disclose siRNAs in which single-chain lipids binds at the 3'-end. Patent Documents 6 and 7 and the like disclose a siRNA to which a lipid comprising an GalNac (N-acetylgalactosamine) derivative binds. Also, Patent Document 8 discloses a siRNA to which phosphatidylethanolamine binds.

In addition, Patent Document 9 discloses that by binding tocophenol to a double-stranded oligonucleotide comprising an RNA oligonucleotide complementary to an antisense oligonucleotide, the oligonucleotide was efficiently delivered to and accumulated in the liver and suppressed expression of the target gene in the liver compared to a single-stranded antisense oligonucleotide in mice. Patent Document 10 discloses that by binding a GalNac derivative to a double-stranded oligonucleotide comprising an RNA oligonucleotide complementary to an antisense oligonucleotide, when it administered not only intravenously but also subcutaneously, the oligonucleotide was efficiently delivered to and accumulated in the liver and suppressed expression of the target gene in the liver.

PRIOR ART

Patent Document

Patent Document 1: WO98/39352
Patent Document 2: WO2005/021570
Patent Document 3: WO2003/068795
Patent Document 4: WO2011/052436
Patent Document 5: WO2011/156202
Patent Document 6: WO2009/126933
Patent Document 7: WO2012/037254
Patent Document 8: WO2009/123185
Patent Document 9: WO2013/089283
Patent Document 10: WO2015/105083
Patent Document 11: WO2017/057540

Non-Patent Document

Non-Patent Document 1: Nature Biotechnology, 2007, vol. 25, no. 10, 1149-1157
Non-Patent Document 2: Bioorganic & Medicinal Chemistry, 2008, vol. 16, 7698-7704
Non-Patent Document 3: Journal of Controlled Release, 2015, vol. 220, 44-50

SUMMARY OF THE INVENTION

Problems to be Solved by the Invention

The purpose of the present invention is to provide novel complexes which can enhance suppressing activity of the target gene expression of the nucleic acid medicines in the complexes.

Means for Solving the Problem

The present inventors have intensively studied and synthesized a complex in which a multibranched lipid binds to an oligonucleotide comprising a nucleic acid medicine. They have found that a complex comprising siRNA as a nucleic acid medicine improves the suppressing activity of the target gene expression without using a gene transfection reagent and improves the suppressing activity of the target gene expression not only in liver but also in skeletal muscles, heart, fats, and the like. They have also found that a complex comprising a miRNA as a nucleic acid medicine have improved antitumor effect compared to a miRNA. They have also found that the complexes are resistant to lipolytic enzymes.

The present invention relates to a complex in which multibranched lipids bind through a linker to an oligonucleotide comprising a nucleic acid medicine. As the multibranched lipid, a multibranched lipid comprising 1 to 3 chain(s) consisting of an amide-mediated alkyl at the terminus thereof is especially preferable. The present inventors have confirmed that the suppressing activity of the target gene expression is reduced in a complex in which a multi-branched lipid comprising four chains of amide-mediated alkyl at the terminus bind to an oligonucleotide comprising a nucleic acid medicine (Comparative Example: siRNA 101).

The present invention specifically relates to the followings.
(1-1) A complex, wherein
a lipid of a group of the formula:

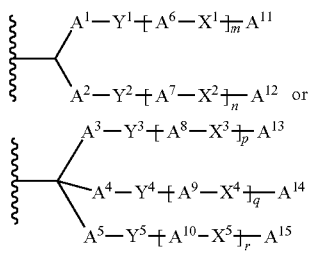

wherein
$A^{11}$ is substituted or unsubstituted alkyl, substituted or unsubstituted alkenyl, substituted or unsubstituted alkynyl, or a group of the formula:

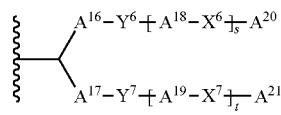

$A^1$ to $A^{10}$ and $A^{16}$ to $A^{19}$ are each independently a bond, substituted or unsubstituted alkylene, substituted or unsubstituted alkenylene, or substituted or unsubstituted alkynylene,
when $A^1$ and $A^2$ or $A^{16}$ and $A^{17}$ are substituted or unsubstituted alkylene, substituted or unsubstituted alkenylene, substituted or unsubstituted alkynylene or
any carbon atom of $A^1$ and any carbon atom of $A^2$, or any carbon atom of $A^{16}$ and any carbon atom of $A^{17}$ taken together may form substituted aromatic carbocycle or substituted non-aromatic carbocycle,
$Y^1$ to $Y^7$ are each independently a bond or O,
$X^1$, $X^3$ and $X^6$ are each independently $NR^1C(=O)$, $C(=O)NR^1$, $R^2C(=O)NR^1$ or $NR^1C(=O)R^2$,
$X^2$, $X^4$, $X^5$ and $X^7$ are each independently a bond, $NR^3C(=O)$, $C(=O)NR^3$, $R^4C(=O)NR^3$, $NR^3C(=O)R^4$ or S—S,
$R^2$ and $R^4$ are each independently O or $NR^5$,
$R^1$, $R^3$ and $R^5$ are each independently hydrogen, substituted or unsubstituted alkyl, substituted or unsubstituted alkenyl, or substituted or unsubstituted alkynyl,
$A^{12}$ is substituted or unsubstituted alkyl, substituted or unsubstituted alkenyl, substituted or unsubstituted alkynyl, or a group comprising a fat-soluble compound,
$A^{13}$ to $A^{15}$, $A^{20}$ and $A^{21}$ are each independently substituted or unsubstituted alkyl, substituted or unsubstituted alkenyl, or substituted or unsubstituted alkynyl,
m, n, p, q, r, s and t are each independently 1 or 2,
provided that a substituent for the alkyl, alkenyl, alkynyl, alkylene, alkenylene and alkynylene is halogen, hydroxy, carboxy, amino, imino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, aromatic carbocyclyl, non-aromatic carbocyclyl, non-aromatic heterocyclyl, non-aromatic heterocyclyl, aromatic carbocyclylcarbonyl, non-aromatic carbocyclylcarbonyl, aromatic heterocyclylcarbonyl or non-aromatic heterocyclylcarbonyl, and may have any one or more substituent(s) selected from Group α.

Group α hydroxy, alkyl, alkyloxy, mercapto, alkylthio, amino, alkylamino and halogen,
binds through a linker to an oligonucleotide having suppressing activity of the target gene expression.
(1-2) The complex of (1-1), wherein, in the lipid,
$A^1$ to $A^5$ and $Y^1$ to $Y^5$ are a bond,
$A^6$ to $A^{10}$ are each independently a bond, substituted or unsubstituted alkylene, substituted or unsubstituted alkenylene, or substituted or unsubstituted alkynylene,
$X^1$ to $X^5$ are NHC(=O), and
m, n, p, q and r are 1.
(1-3) The complex of (1-1) or (1-2), wherein $A^{11}$ and $A^{13}$ are C6 to C30 alkyl.
(1-4) The complex of any one of (1-1) to (1-3), wherein the lipid binds at the 3'-end and/or 5'-end of the oligonucleotide.
(1-5) The complex of any one of (1-1) to (1-4), wherein the linker is a group of the formula:

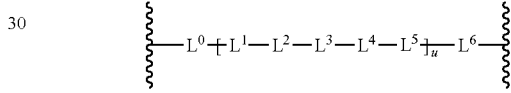

wherein
$L^0$ binds to the oligonucleotide and $L^6$ binds to lipid.
$L^0$ is a bond, a nucleotide linker or a non-nucleotide linker,
$L^1$ is a group of the formula:

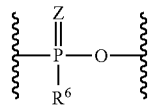

wherein
Z are each independently O or S,
$R^6$ are each independently hydroxy, alkyl or alkyloxy,
$L^2$ and $L^4$ are each independently a bond or substituted or unsubstituted C1 to C20 alkylene,
$L^3$ are each independently a bond; $C(=O)NR^7$, wherein $R^7$ is hydrogen or substituted or unsubstituted alkyl; $NR^8C(=O)$, wherein $R^8$ is hydrogen, substituted or unsubstituted alkyl or $R^8$ and a carbon atom in alkylene of $L^2$ taken together may form substituted or unsubstituted nitrogen-containing ring; or S—S,
$L^5$ are each independently a bond, substituted or unsubstituted C1 to C20 alkylene, $C(=O)NR^9$, $NR^9C(=O)$, $NR^9$, O, or substituted or unsubstituted non-aromatic heterocyclyl,
$R^9$ is each independently hydrogen, substituted or unsubstituted alkyl, substituted or unsubstituted alkenyl, or substituted or unsubstituted alkynyl,
u is 1 or 2, and
$L^6$ is a bond or an amino acid linker.
(1-6) The complex of any one of (C-1) to (C-7) which is any one of the followings:

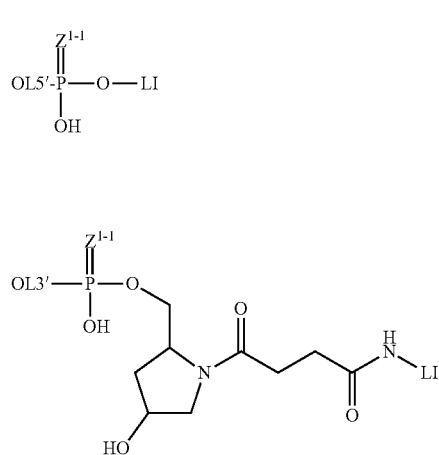

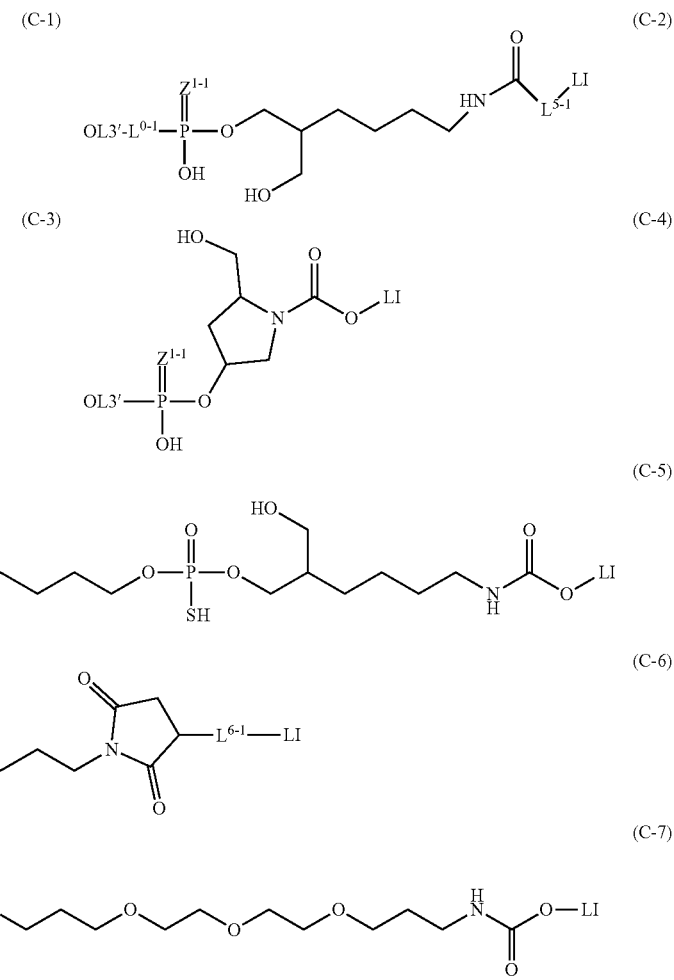

wherein
OL is an oligonucleotide having suppressing activity of the target gene expression,
5' means that it binds at the 5'-end of the oligonucleotide,
3' means that it binds at the 3'-end of the oligonucleotide,
$Z^{1-1}$ is O or S,
$L^{0-1}$ is a bond, a nucleotide linker or a non-nucleotide linker,
$L^{5-1}$ is a bond, NH or O,
$L^{6-1}$ is a bond or an amino acid linker,
LI is a lipid of any one of a group of the formula: (LI-1) to (LI-9).

(LI-1)

wherein
$A^{1-1}$ is a bond or methylene,
$A^{2-1}$ is C1 to C4 straight alkylene,
$A^{11-1}$ is C7 to C23 straight or branched alkyl, and
$A^{12-1}$ is C3 to C23 straight or branched alkyl or alkenyl, a group comprising a fat-soluble compound, or a group of the formula:

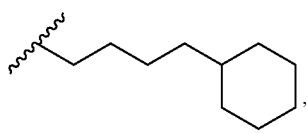

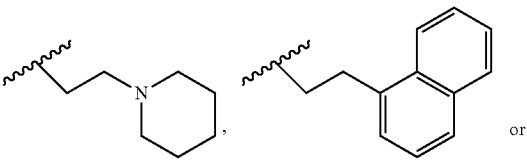

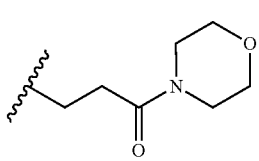

-continued (LI-2)

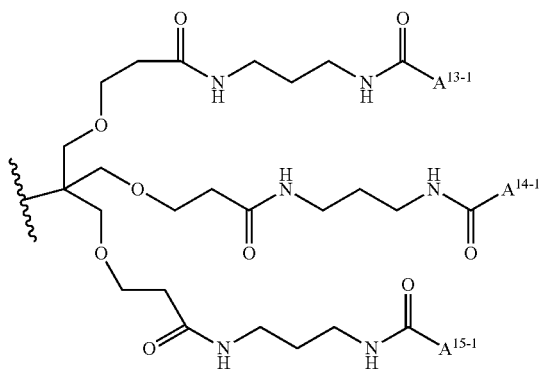

wherein $A^{13-1}$, $A^{14-1}$ and $A^{15-1}$ are C9 to C13 straight alkyl.

(LI-3)

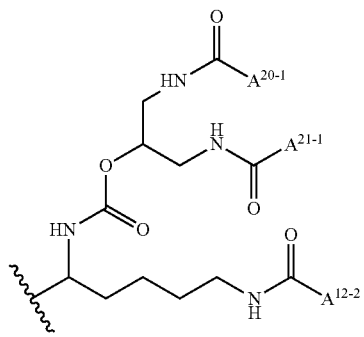

wherein
$A^{20-1}$ and $A^{21-1}$ is C13 straight alkyl, and
$A^{12-2}$ is C15 straight alkyl or a group comprising a fat-soluble compound.

(LI-4)

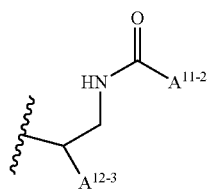

wherein
$A^{11-2}$ is C15 straight alkyl, and
$A^{12-3}$ is C1 to C4 straight alkyl substituted with amino.

(LI-5)

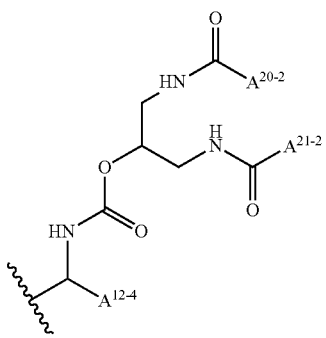

wherein
$A^{20-2}$ and $A^{21-2}$ are C13 straight alkyl, and
$A^{12-4}$ is C4 straight alkyl substituted with amino.

(LI-6)

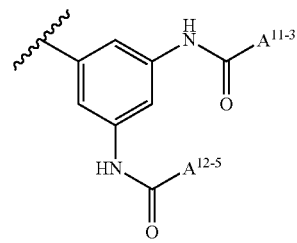

wherein $A^{11-3}$ and $A^{12-5}$ are C15 straight alkyl.

(LI-7)

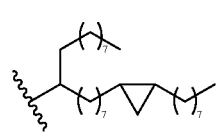

(LI-8)

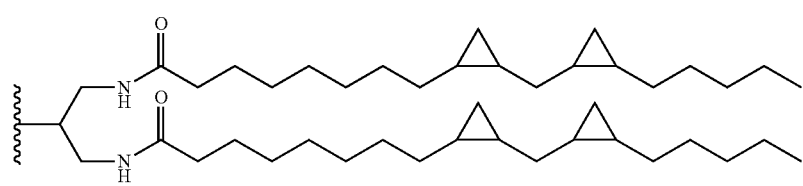

-continued

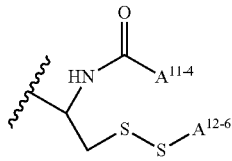

wherein
$A^{11-4}$ is C14 straight alkyl, and
$A^{12-6}$ is C6 to C12 straight alkyl.

(1-7) A pharmaceutical composition comprising the complex of any one of (1-1) to (1-6).

(1-8) The complex of (1-5), wherein, in the linker,
$L^2$ is substituted or unsubstituted C1 to C20 alkylene,
$L^3$ is $NR^8C(=O)$, wherein $R^8$ is hydrogen or substituted or unsubstituted alkyl,
$L^4$ is a bond,
$L^5$ is a bond, $NR^9$ or O,
u is 1, and
$L^6$ is a bond.

(1-9) The complex of (1-5), wherein, in the linker,
$L^0$ is a bond,
$L^2$ to $L^5$ is a bond,
$L^6$ is a bond, and
u is 1.

(1-10) The complex of (1-5), wherein, in the linker,
$L^0$ is a bond,
$L^3$ is $NR^8C(=O)$, wherein $R^8$ and a carbon atom in alkylene of $L^2$ taken together may form substituted or unsubstituted nitrogen-containing ring,
$L^5$ is $C(=O)NR^9$ or O,
u is 1, and
$L^6$ is a bond.

(1-11) The complex of (1-5), wherein, in the linker,
$L^0$ is a bond or a nucleotide linker,
$L^2$ and $L^4$ are substituted or unsubstituted C1 to C20 alkylene,
$L^3$ is $NHC(=O)$ or S—S,
$L^5$ is O, and
u is 1.

(1-12) The complex of (1-5), wherein, in the linker,
$L^2$ and $L^4$ are substituted or unsubstituted C1 to C20 alkylene,
$L^3$ is $NR^8C(=O)$, wherein $R^8$ is hydrogen or substituted or unsubstituted alkyl,
$L^5$ is substituted or unsubstituted non-aromatic heterocyclyl,
u is 1, and
$L^6$ is an amino acid linker.

The present invention also includes the followings.

(2-1) A complex in which a double-stranded oligonucleotide having suppressing activity of the target gene expression, and
the first strand is an oligonucleotide consisting of a sequence capable of hybridizing with the target sequence in the target gene, and
the second strand is an oligonucleotide consisting of a sequence capable of hybridizing with the first strand, (LI-9)

wherein a lipid of a group of the formula:

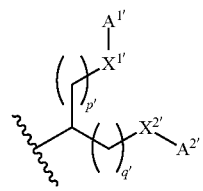

wherein
$X^{1'}$ and $X^{2'}$ are each independently a bond, $NR^{1'}C(=O)$, $C(=O)NR^{1'}$,
$R^{2'}C(=O)NR^{1'}$ or $NR^{1'}C(=O)R^{2'}$,
$R^{2'}$ is O or $NR^{3'}$,
$R^{1'}$ and $R^{3'}$ are each independently hydrogen, substituted or unsubstituted alkyl, substituted or unsubstituted alkenyl, or substituted or unsubstituted alkynyl,
$A^{1'}$ and $A^{2'}$ are each independently substituted or unsubstituted alkyl, substituted or unsubstituted alkenyl, or substituted or unsubstituted alkynyl, and
p' and q' are each independently an integer of 0 to 4,
provided that a substituent for alkyl, alkenyl and alkynyl is halogen, carboxy, amino, imino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, aromatic carbocyclyl, non-aromatic carbocyclyl, non-aromatic heterocyclyl or non-aromatic heterocyclyl, and may have any one or more substituent(s) selected from Group α'.
Group α': hydroxy, alkyl, alkyloxy, mercapto, alkylthio, amino, alkylamino and halogen.
binds through a linker to the first strand and/or the second strand.

(2-2) The complex of (2-1), wherein the lipid is a group of the formula:

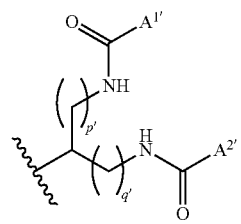

wherein $A^{1'}$, $A^{2'}$, p' or q' has the same meaning as claim 1.
(2-3) The complex of (2-1) or (2-2), wherein $A^{1'}$ and $A^{2'}$ are each independently C6 to C30 alkyl.
(2-4) The complex of any one of (2-1) to (2-3), wherein the lipid binds to the second strand.
(2-5) The complex of (2-4), wherein the lipid binds at the 3' end and/or 5' end of the oligonucleotide.
(2-6) The complex of any one of (2-1) to (2-5), wherein the linker is

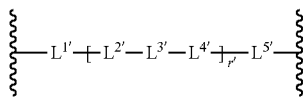

wherein $L^{1\prime}$ binds to the oligonucleotide, and $L^{5\prime}$ binds to the lipid. $L^{1\prime}$ is C(=O)NH, NHC(=O), NHC(=O)NH,

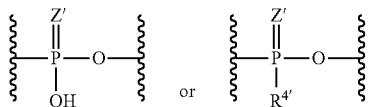

wherein $Z'$ is O or S, and $R^{4\prime}$ is alkyl or alkyloxy, $L^{2\prime}$ are each independently substituted or unsubstituted C1 to C20 alkylene which aromatic ring may mediate, or aromatic ring, $L^{3\prime}$ are each independently a bond; C(=O)NR$^{5\prime}$, wherein $R^{5\prime}$ is hydrogen or substituted or unsubstituted alkyl; or NR$^{6\prime}$C(=O), wherein $R^{6\prime}$ is hydrogen, substituted or unsubstituted alkyl or $R^{6\prime}$ and a carbon atom in alkylene of $L^{2\prime}$ taken together may form substituted or unsubstituted nitrogen-containing ring;

$L^{4\prime}$ are each independently a bond or substituted or unsubstituted C1 to C20 alkylene which aromatic ring may mediate, or aromatic ring, $L^{5\prime}$ is a bond, C(=O)NH, NHC(=O), NH or O, and $r'$ is an integer of 0 to 2.

(2-7) A pharmaceutical composition comprising the complex of any one of (2-1) to (2-6).

Effect of the Invention

The complexes of the present invention are capable of exerting suppressing activity of the target gene expression of nucleic acid medicines in the complexes without using a gene transfer reagent. In addition, since the nucleic acid medicines in the complexes are delivered, accumulated, and exerts the activity not only in liver but also in skeletal muscles, heart, fats and the like, a therapeutic or prophylactic effect of the disease, which it is desired to suppress the target gene expression in skeletal muscles, heart, fats and the like, can be obtained by administration a complex of the present invention including an appropriate nucleic acid medicine.

EMBODIMENTS FOR CARRYING OUT THE INVENTION

Terms used herein, unless otherwise indicated, are used in a sense normally used in this field.

In the present invention, a genetic manipulation method which is well known in this field can be used. For example, it is a method described in Molecular Cloning, A Laboratory Manual, Fourth Edition, Cold Spring Harbor Laboratory Press (2012) or Current Protocols Essential Laboratory Techniques, Current Protocols (2012).

Terms used in this description are explained below. Each term, unless otherwise indicated, has the same meaning when it is used alone or together with other terms.

A "nucleoside" means a compound that a nucleic-acid base and a sugar are bonded by an N-glycoside bond.

An "oligonucleotide" means nucleotides that some of same or different kinds of nucleotide are bonded.

A linkage between a sugar and a sugar in an oligonucleotide (internucleoside linkage) may be a linkage having a natural nucleic acid, phosphodiester (D-oligo), an artificially modified linkage or a linkage without phosphorus atom. Any linkage which is well-known in this field can be used. Examples of an artificially modified linkage are phosphorothioate (S-oligo), methylphosphonate (M-oligo) and boranophosphate. Furthermore, a linkage described in WO2013/022966, WO2011/005761, WO2014/012081, WO2015/125845 or the like can be used. An example of a linkage without phosphorus atom is a bivalent substituent deriving from non-aromatic carbocyclyl or the like substituted with alkyl, non-aromatic carbocyclyl, haloalkyl or halogen. Example is a bivalent substituent deriving from siloxane, sulfide, sulfoxide, sulfone, acetyl, acetyl formate, acetyl thioformate, acetyl methylene formate, acetyl thioformate, alkenyl, sulfamate, methyleneimino, methylenehydrazino, sulfonate, sulfonamide, amide or the like. In an oligonucleotide, linkages may be same or different.

In this description, a "DNA nucleoside" or "RNA nucleoside" means a natural DNA nucleoside or natural RNA nucleoside, and a part of a nucleotide, which is one unit for a component of an oligonucleotide. A "natural DNA nucleoside" is as below.

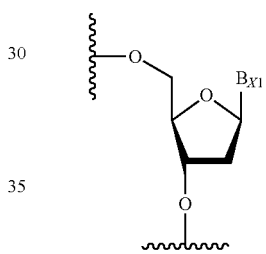

wherein $B_{X1}$ is adenine, guanine, cytosine or thymine.

A "natural RNA nucleoside" is as below.

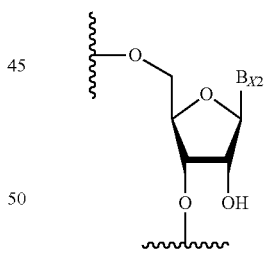

wherein $B_{X2}$ is adenine, guanine, cytosine or uracil.

An "DNA oligonucleotide" means an oligonucleotide that some DNA nucleosides are bounded. An "RNA oligonucleotide" means an oligonucleotide that some RNA nucleosides are bounded.

In this description, a "nucleoside derivative" means a nucleoside wherein the nucleic-acid base and/or sugar part of DNA nucleoside or RNA nucleoside was artificially modified. It also means abasic nucleoside wherein the nucleic-acid base is deleted. Any well-known modification for a nucleoside in this field can be used.

Examples of modification for a nucleic-acid base are 5-methyl cytosine, 5-hydroxymethyl cytosine and 5-propynyl cytosine.

An example of modification for a sugar part is a substituent at the 2' position of a sugar moiety. Examples are 2'-F, 2'-OCH$_3$ (2'-OMe) and 2'-OCH$_2$CH$_2$OCH$_3$ (2'-MOE).

The other example is the following bridged structure between the 4' and 2' positions of a sugar moiety.

4'-(CR$^{7'}$R$^{8'}$)m'-O-2', 4'-(CR$^{7'}$R$^{8'}$)m'-S-2', 4'-(CR$^{7'}$R$^{8'}$)m'-O—C(=O)-2', 4'-(CR$^{7'}$R$^{8'}$)m'-NR$^{9'}$-O—(CR$^{7'}$R$^{8'}$)m$_1$'-2', 4'-(CR$^{7'}$R$^{8'}$)m$_1$'-C(=O)—NR$^{9'}$-2', 4'-(CR$^{7'}$R$^{8'}$)m$_2$'-C(=O)—NR$^{9'}$-Y$^{4'}$-2', 4'-(CR$^{7'}$R$^{8'}$)m$_1$-SO$_2$—NR$^{9'}$-2', or

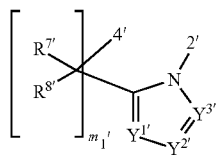

wherein
Y$^{4'}$ is O, S, NH or CH$_2$,
R$^{7'}$ are each independently a hydrogen atom, halogen, cyano, substituted or unsubstituted alkyl, substituted or unsubstituted alkenyl, or substituted or unsubstituted alkynyl,
R$^{8'}$ are each independently a hydrogen atom, halogen, cyano, substituted or unsubstituted alkyl, substituted or unsubstituted alkenyl, or substituted or unsubstituted alkynyl,
R$^{9'}$ is a hydrogen atom, substituted or unsubstituted alkyl, substituted or unsubstituted alkenyl, substituted or unsubstituted alkynyl, substituted or unsubstituted aromatic carbocyclyl, substituted or unsubstituted non-aromatic carbocyclyl, substituted or unsubstituted aromatic heterocyclyl, substituted or unsubstituted non-aromatic heterocyclyl, substituted or unsubstituted aromatic carbocyclylalky, substituted or unsubstituted non-aromatic carbocyclylalky, substituted or unsubstituted aromatic heterocyclylalkyl, or substituted or unsubstituted non-aromatic heterocyclylalkyl,
Y$^{1'}$ is CR$^{10'}$ or N,
Y$^{2'}$ is CR$^{11'}$ or N,
Y$^{3'}$ is CR$^{12'}$ or N,
R$^{10'}$, R$^{11'}$ and R$^{12'}$ are each independently a hydrogen atom, halogen, cyano, substituted or unsubstituted alkyl, substituted or unsubstituted alkenyl, substituted or unsubstituted alkynyl, substituted or unsubstituted amino, substituted or unsubstituted alkyloxy, substituted or unsubstituted alkylcarbonylamino, substituted or unsubstituted alkenylcarbonylamino, substituted or unsubstituted alkynylcarbonylamino, substituted or unsubstituted alkylcarbamoyl, substituted or unsubstituted alkenylcarbamoyl, or substituted or unsubstituted alkynylcarbamoyl,
m' is an integer of 1 to 4,
m$_1$' is an integer of 0 to 3,
m$_2$' is 0 or 1.

R$^{7'}$ and R$^{8'}$ is preferably a hydrogen atom.
R$^{9'}$ is preferably a hydrogen atom, alkyl, alkenyl, alkynyl, aromatic carbocyclyl, non-aromatic carbocyclyl, aromatic heterocyclyl, non-aromatic heterocyclyl, aromatic carbocyclylalky, non-aromatic carbocyclylalky, aromatic heterocyclylalkyl or non-aromatic heterocyclylalkyl, and may have any one or more substituent(s) selected from Group α'.

Group α': hydroxy, alkyl, alkyloxy, mercapto, alkylthio, amino, alkylamino and halogen.

The bridged structure is preferably 4'-(CR$^{7'}$R$^{8'}$)m'-O-2' or 4'-(CR$^{7'}$R$^{8'}$)m$_1$'-C(=O)—NR$^{9'}$-2' (AmNA, Bridged nucleic acid), wherein
R$^{7'}$ are each independently a hydrogen atom, halogen, cyano, substituted or unsubstituted alkyl, substituted or unsubstituted alkenyl, or substituted or unsubstituted alkynyl,
R$^{8'}$ are each independently a hydrogen atom, halogen, cyano, substituted or unsubstituted alkyl, substituted or unsubstituted alkenyl, or substituted or unsubstituted alkynyl,
R$^{9'}$ is a hydrogen atom, substituted or unsubstituted alkyl, substituted or unsubstituted alkenyl, or substituted or unsubstituted alkynyl,
m' is an integer of 1 to 4, and
m$_1$' is an integer of 0 to 2.

The bridged structure is more preferably 4'-(CH$_2$)m'-O-2', wherein m' is an integer of 1 to 4, or 4'-C(=O)—NR$^{9'}$-2', wherein R$^{9'}$ is a hydrogen atom or alkyl.

4'-(CH$_2$)m'-O-2', wherein m' is an integer of 1 to 4, is more preferably 4'-CH$_2$—O-2' (LNA, Locked nucleic acid). Examples and the methods for preparation are described in WO98/39352, WO2003/068795, WO2005/021570 or the like.

4'-C(=O)—NR$^{9'}$-2', wherein R$^{9'}$ is a hydrogen atom or alkyl, is more preferably 4'-C(=O)—NCH$_3$-2'. Examples and the methods for preparation are described in WO2011/052436.

Examples of the well-known modification for a nucleotide and the method for modification in this field are described in the following patent documents.
WO98/39352, WO99/014226, WO2000/056748, WO2005/021570, WO2003/068795, WO2011/052436, WO2004/016749, WO2005/083124, WO2007/143315, WO2009/071680, WO2014/112463, WO2014/126229 and the like.

"Halogen" includes a fluorine atom, a chlorine atom, a bromine atom and an iodine atom. A fluorine atom and a chlorine atom are especially preferable.

"Alkyl" includes a C1 to C15, preferably a C1 to C10, more preferably a C1 to C6 and even more preferably a C1 to C4 linear or branched hydrocarbon group. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl and n-decyl. A preferred embodiment is methyl, ethyl, n-propyl, isopropyl, n-butyl, isobutyl, sec-butyl, tert-butyl or n-pentyl. A more preferred embodiment is methyl, ethyl, n-propyl, isopropyl or tert-butyl.

"Alkenyl" includes a C2 to C15, preferably a C2 to C10, more preferably a C2 to C6 and further preferably a C2 to C4 linear or branched hydrocarbon group having one or more double bond(s) at any position(s). Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl and pentadecenyl. A preferred embodiment is vinyl, allyl, propenyl, isopropenyl or butenyl.

"Alkynyl" includes a C2 to C10, preferably a C2 to C8, more preferably a C2 to C6 and further preferably a C2 to C4 linear or branched hydrocarbon group having one or more triple bond(s) at any position(s). Examples include ethynyl, propynyl, butynyl, pentynyl, hexynyl, heptynyl, octynyl, nonynyl and decynyl. Furthermore, it may have double bond(s) at any position(s). A preferred embodiment is ethynyl, propynyl, butynyl or pentynyl.

"Aromatic carbocyclyl" means a cyclic aromatic hydrocarbon group which is monocyclic or polycyclic having two or more rings. Examples include phenyl, naphthyl, anthryl and phenanthryl. A preferred embodiment is phenyl.

"Non-aromatic carbocyclyl" means a cyclic saturated hydrocarbon group or cyclic unsaturated non-aromatic hydrocarbon group, which is monocyclic or polycyclic having two or more rings. Examples of the non-aromatic carbocyclyl, which is polycyclic having two or more rings, include a fused ring group wherein a non-aromatic carbocyclyl, which is monocyclic or polycyclic having two or more rings, is fused with a ring of the above "aromatic carbocyclyl".

In addition, examples of the "non-aromatic carbocyclyl" also include a group having a bridge and a group to form a spiro ring as follows:

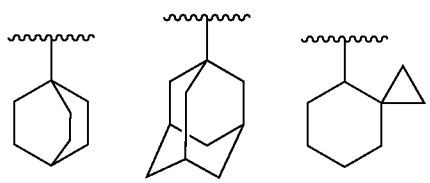 [SMILES: *C12CCC(CC1)CC2 ; *C12CC3CC(CC(C3)C1)C2 ; *C1CCCCC12CC2]

The non-aromatic carbocyclyl, which is monocyclic, is preferably C3 to C16, more preferably C3 to C12 and further preferably C4 to C8 carbocyclyl. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl and cyclohexadienyl.

Examples of non-aromatic carbocyclyl, which is polycyclic having two or more rings, include indanyl, indenyl, acenaphthyl, tetrahydronaphthyl and fluorenyl.

"Aromatic heterocyclyl" means an aromatic cyclyl, which is monocyclic or polycyclic having two or more rings, containing one or more of heteroatom(s) selected independently from O, S and N.

Examples of aromatic heterocyclyl, which is polycyclic having two or more rings, include a fused ring group wherein an aromatic heterocyclyl, which is monocyclic or polycyclic having two or more rings, is fused with a ring of the above "aromatic carbocyclyl" and/or "non-aromatic carbocyclyl".

The aromatic heterocyclyl, which is monocyclic, is preferably a 5- to 8-membered and more preferably 5- to 6-membered ring. Examples include pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl and thiadiazolyl.

Examples of aromatic heterocyclyl, which is bicyclic, include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl and thiazolopyridyl.

Examples of aromatic heterocyclyl, which is polycyclic having three or more rings, include carbazolyl, acridinyl, xanthenyl, phenothiazinyl, phenoxathiinyl, phenoxazinyl and dibenzofuryl.

"Non-aromatic heterocyclyl" means a non-aromatic cyclyl, which is monocyclic or polycyclic having two or more rings, containing one or more heteroatom(s) selected independently from O, S and N.

Examples of non-aromatic heterocyclyl, which is polycyclic having two or more rings, include a fused ring group wherein a non-aromatic heterocycle, which is monocyclic or polycyclic having two or more rings, is fused with a ring of "aromatic carbocyclyl", "non-aromatic carbocyclyl" and/or "aromatic heterocyclyl".

In addition, examples of the "non-aromatic heterocyclyl" also include a group having a bridge and a group to form a spiro ring as follows:

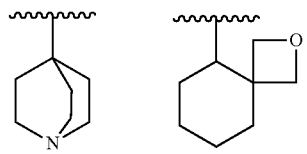 [SMILES: *C12CCN(CC1)CC2 ; *C1CCCCC12COC2]

The non-aromatic heterocyclyl, which is monocyclic, is preferably a 3- to 8-membered and more preferably 5- to 6-membered ring. Examples include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, tetrahydropyridazinyl, hexahydropyrimidinyl, dioxolanyl, dioxazinyl, aziridinyl, dioxolinyl, oxepanyl, thiolanyl, thiinyl and thiazinyl.

Examples of non-aromatic heterocyclyl, which is polycyclic having two or more rings, include indolinyl, isoindolinyl, chromanyl and isochromanyl.

"Haloalkyl" means a group wherein one or more "halogen" binds to "alkyl". Examples include monofluoromethyl, monofluoroethyl, monofluoropropyl, 2,2,3,3,3-pentafluoropropyl, monochloromethyl, trifluoromethyl, trichloromethyl, 2,2,2-trifluoroethyl, 2,2,2-trichloroethyl, 1,2-dibromoethyl and 1,1,1-trifluoropropane-2-yl. A preferred embodiment is trifluoromethyl or trichloromethyl.

"Alkylamino" includes monoalkylamino and dialkylamino.

"Monoalkylamino" means a group wherein a hydrogen atom attached to a nitrogen atom of an amino group is replaced with "alkyl". Examples include methylamino, ethylamino and isopropylamino. Preferably, it is methylamino or ethylamino.

"Dialkylamino" means a group wherein two hydrogen atoms attached to a nitrogen atom of an amino group are replaced with two "alkyl". These two alkyl groups may be the same or different. Examples include dimethylamino, diethylamino, N, N-diisopropylamino, N-methyl-N-ethylamino and N-isopropyl-N-ethylamino. Preferably, it is dimethylamino or diethylamino.

"Alkylcarbonylamino", "alkenylcarbonyamino" or "alkynylcarbonyamino" means a group wherein one or two hydrogen atoms attached to a nitrogen atom of an amino group are replaced with one or two "alkylcarbonyl", "alkenylcarbony" or "alkynylcarbony". The two alkylcarbonyl groups may be the same or different. Examples of "alkylcarbonylamino" include methylcarbonylamino, and ethylcarbonylamino. Examples of "alkenylcarbonylamino" include vinylcarbonylamino and propenylcarbonylamino. Examples of "alkynylcarbonylamino" include ethynylcarbonylamino and propynylcarbonylamino.

"Alkylcarbamoyl", "alkenylcarbamoyl" or "alkynylcarbamoyl" means a group wherein one or two hydrogen atoms attached to a nitrogen atom of a carbamoyl group are replaced with one or two alkyl(s), alkenyl(s) or alkynyl(s). These two alkyl groups may be the same or different. Examples of "alkylcarbamoyl" include methylcarbamoyl, ethylcarbamoyl, dimethylcarbamoyl and diethylcarbamoyl. Examples of alkenylcarbamoyl include vinylcarbamoyl and propenylcarbamoyl. Examples of alkynylcarbamoyl include ethynylcarbamoyl and propynylcarbamoyl.

"Aromatic carbocyclylalkyl" means an alkyl substituted with one or more "aromatic carbocyclyl". Examples include benzyl, phenethyl, phenylpropyl, benzhydryl, trityl, naphthylmethyl and a group of the formula of

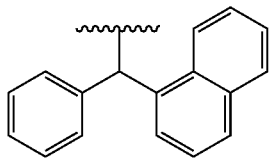 [SMILES: *C(c1ccccc1)c1cccc2ccccc12]

A preferred embodiment of "aromatic carbocyclylalkyl" is benzyl, phenethyl or benzhydryl.

"Non-aromatic carbocyclylalkyl" means an alkyl substituted with one or more "non-aromatic carbocyclyl". The "non-aromatic carbocyclylalkyl" also includes "non-aromatic carbocyclylalkyl" wherein the alkyl part is substituted with "aromatic carbocyclyl". Examples include cyclopropylmethyl, cyclobutylmethyl, cyclopenthylmethyl, cyclohexylmethyl and a group of the formula of

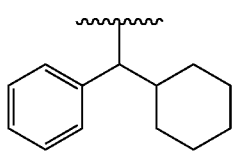 [SMILES: *C(c1ccccc1)C1CCCCC1]

"Aromatic heterocyclylalkyl" means an alkyl substituted with one or more "aromatic heterocyclyl". The "aromatic heterocyclylalkyl" also includes "aromatic heterocyclylalkyl" wherein the alkyl part is substituted with the above "aromatic carbocyclyl" and/or "non-aromatic carbocyclyl". Examples include pyridylmethyl, furanylmethyl, imidazolylmethyl, indolylmethyl, benzothiophenylmethyl, oxazolylmethyl, isoxazolylmethyl, thiazolylmethyl, isothiazolylmethyl, pyrazolylmethyl, isopyrazolylmethyl, pyrrolidinylmethyl, benzoxazolylmethyl and groups of the formula of

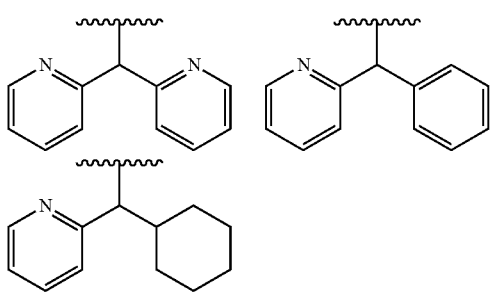

"Non-aromatic heterocyclylalkyl" means an alkyl substituted with one or more "non-aromatic heterocyclyl". The "non-aromatic heterocyclylalkyl" also includes "non-aromatic heterocyclylalkyl" wherein the alkyl part is substituted with "aromatic carbocyclyl", "non-aromatic carbocyclyl" and/or "aromatic heterocyclyl". Examples include tetrahydropyranylmethyl, morpholinylethyl, piperidinylmethyl, piperazinylmethyl and groups of the formula of

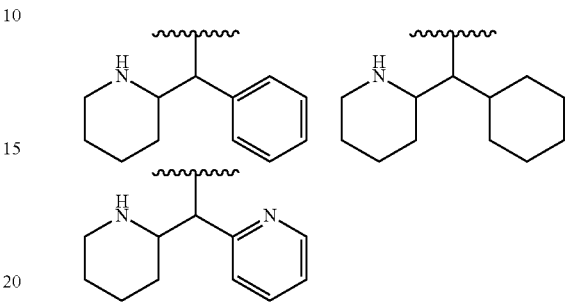

Examples of the substituents for "substituted or unsubstituted alkyl", "substituted or unsubstituted alkenyl", "substituted or unsubstituted alkynyl", "substituted or unsubstituted alkyloxy", "substituted or unsubstituted alkylcarbonylamino", "substituted or unsubstituted alkenylcarbonylamino", "substituted or unsubstituted alkynylcarbonylamino", "substituted or unsubstituted alkylcarbamoyl", "substituted or unsubstituted alkenylcarbamoyl "or "substituted or unsubstituted alkynylcarbamoyl" include the following substituents. A carbon atom at any position(s) may be bonded to one or more group(s) selected from the following Group ß.

Group ß: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, alkyloxy, alkenyloxy, alkynyloxy, haloalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalkyoxy, non-aromatic carbocyclylalkyoxy, aromatic heterocyclylalkyoxy, non-aromatic heterocyclylalkyloxy, aromatic carbocyclylalkyoxycarbonyl, non-aromatic carbocyclylalkyoxycarbonyl, aromatic heterocyclylalkyloxycarbonyl, non-aromatic heterocyclylalkyloxycarbonyl, aromatic carbocyclylalkyamino, non-aromatic carbocyclylalkyamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl and non-aromatic heterocyclylsulfonyl. Furthermore, the substituent may have one or more substituent(s) selected from the above Group α.

Examples of the substituents on the ring of "aromatic carbocyclyl", "non-aromatic carbocyclyl", "aromatic heterocyclyl" or "non-aromatic heterocyclyl" of "substituted or unsubstituted aromatic carbocyclyl", "substituted or unsubstituted non-aromatic carbocyclyl", "substituted or unsubstituted aromatic heterocyclyl" and "substituted or unsubstituted non-aromatic heterocyclyl" include the following substituents. An atom at any position(s) on the ring may be bonded to one or more group(s) selected from the following Group γ.

Group γ: halogen, hydroxy, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, alkyl, alkenyl, alkynyl, haloalkyl, alkyloxy, alkenyloxy, alkynyloxy, haloalkyloxy, alkyloxyalkyl, alkyloxyalkyloxy, alkylcarbonyl, alkenylcarbonyl, alkynylcarbonyl, monoalkylamino, dialkylamino, alkylsulfonyl, alkenylsulfonyl, alkynylsulfonyl, monoalkylcarbonylamino, dialkylcarbonylamino, monoalkylsulfonylamino, dialkylsulfonylamino, alkylimino, alkenylimino, alkynylimino, alkylcarbonylimino, alkenylcarbonylimino, alkynylcarbonylimino, alkyloxyimino, alkenyloxyimino, alkynyloxyimino, alkylcarbonyloxy, alkenylcarbonyloxy, alkynylcarbonyloxy, alkyloxycarbonyl, alkenyloxycarbonyl, alkynyloxycarbonyl, alkylsulfanyl, alkenylsulfanyl, alkynylsulfanyl, alkylsulfinyl, alkenylsulfinyl, alkynylsulfinyl, monoalkylcarbamoyl, dialkylcarbamoyl, monoalkylsulfamoyl, dialkylsulfamoyl, aromatic carbocyclyl, non-aromatic carbocyclyl, aromatic heterocyclyl, non-aromatic heterocyclyl, aromatic carbocyclyloxy, non-aromatic carbocyclyloxy, aromatic heterocyclyloxy, non-aromatic heterocyclyloxy, aromatic carbocyclylcarbonyl, non-aromatic carbocyclylcarbonyl, aromatic heterocyclylcarbonyl, non-aromatic heterocyclylcarbonyl, aromatic carbocyclyloxycarbonyl, non-aromatic carbocyclyloxycarbonyl, aromatic heterocyclyloxycarbonyl, non-aromatic heterocyclyloxycarbonyl, aromatic carbocyclylalky, non-aromatic carbocyclylalky, aromatic heterocyclylalkyl, non-aromatic heterocyclylalkyl, aromatic carbocyclylalkyoxy, non-aromatic carbocyclylalkyoxy, aromatic heterocyclylalkyloxy, non-aromatic heterocyclylalkyloxy, aromatic carbocyclylalkyoxycarbonyl, non-aromatic carbocyclylalkyoxycarbonyl, aromatic heterocyclylalkyloxycarbonyl, non-aromatic heterocyclylalkyloxycarbonyl, aromatic carbocyclylalkyoxyalkyl, non-aromatic carbocyclylalkyoxyalkyl, aromatic heterocyclylalkyloxyalkyl, non-aromatic heterocyclylalkyloxyalkyl, aromatic carbocyclylalkyamino, non-aromatic carbocyclylalkyamino, aromatic heterocyclylalkylamino, non-aromatic heterocyclylalkylamino, aromatic carbocyclylsulfanyl, non-aromatic carbocyclylsulfanyl, aromatic heterocyclylsulfanyl, non-aromatic heterocyclylsulfanyl, non-aromatic carbocyclylsulfonyl, aromatic carbocyclylsulfonyl, aromatic heterocyclylsulfonyl and non-aromatic heterocyclylsulfonyl. Furthermore, the substituent may have one or more substituent selected from the above Group α.

Additionally, "substituted or unsubstituted non-aromatic carbocyclyl" and "substituted or unsubstituted non-aromatic heterocyclyl" may be substituted with "oxo". In this case, it means a group wherein two hydrogen atoms on a carbon atom are substituted as below.

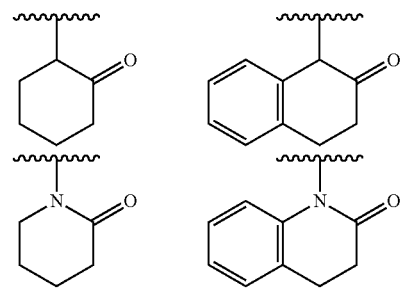

Here, the present invention is explained in detail.
The complex of the present invention is that a lipid of a group of the formula

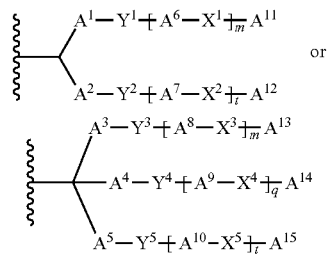

wherein
$A^{11}$ is substituted or unsubstituted alkyl, substituted or unsubstituted alkenyl, substituted or unsubstituted alkynyl or a group of the formula:

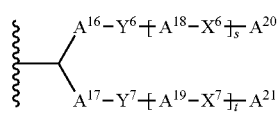

$A^1$ to $A^{10}$ and $A^{16}$ to $A^{19}$ are each independently a bond, substituted or unsubstituted alkylene, substituted or unsubstituted alkenylene, or substituted or unsubstituted alkynylene,
when $A^1$ and $A^2$ or $A^{16}$ and $A^{17}$ are substituted or unsubstituted alkylene, substituted or unsubstituted alkenylene, or substituted or unsubstituted alkynylene or
any carbon atom of $A^1$ and any carbon atom of $A^2$, or any carbon atom of $A^{16}$ and any carbon atom of $A^{17}$ taken together may form substituted aromatic carbocycle or substituted non-aromatic carbocycle,
$Y^1$ to $Y^7$ are each independently a bond or O,
$X^1$, $X^3$ and $X^6$ are each independently $NR^1C(=O)$, $C(=O)NR^1$, $R^2C(=O)NR^1$ or $NR^1C(=O)R^2$,
$X^2$, $X^4$, $X^5$ and $X^7$ are each independently a bond, $NR^3C(=O)$, $C(=O)NR^3$,
$R^4C(=O)NR^3$, $NR^3C(=O)R^4$ or S—S,
$R^2$ and $R^4$ are each independently O or $NR^5$,
$R^1$, $R^3$ and $R^5$ are each independently hydrogen, substituted or unsubstituted alkyl, substituted or unsubstituted alkenyl, or substituted or unsubstituted alkynyl, $A^{12}$ and $A^{14}$ are substituted or unsubstituted alkyl, substituted or unsubstituted alkenyl, substituted or unsubstituted alkynyl, or a group comprising a fat-soluble compound, $A^{13}$, $A^{15}$, $A^{20}$ and $A^{21}$ are each independently substituted or unsubstituted alkyl, substituted or unsubstituted alkenyl, or substituted or unsubstituted alkynyl, m, n, p, q, r, s and t are each independently 1 or 2, provided that a substituent for the alkyl, alkenyl, alkynyl, alkylene, alkenylene and alkynylene is halogen, hydroxy, carboxy, amino, imino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, aromatic carbocyclyl, non-aromatic carbocyclyl, non-aromatic heterocyclyl, non-aromatic heterocyclyl, aromatic carbocyclylcarbonyl, non-aromatic carbocyclylcarbonyl, aromatic heterocyclylcarbonyl or non-aromatic heterocyclylcarbonyl, and may have any one or more substituent(s) selected from Group α.

Group α hydroxy, alkyl, alkyloxy, mercapto, alkylthio, amino, alkylamino and halogen, binds through a linker to an oligonucleotide having suppressing activity of the target gene expression.

Any oligonucleotide known to have "suppressing activity of the target gene expression" can be used as the "oligonucleotide having suppressing activity of the target gene expression" of the complex of the present invention, and the oligonucleotide includes a nucleic acid medicine. "A nucleic acid medicine" includes, for example, a double-stranded oligonucleotide such as a siRNA and a miRNA, and a single-stranded oligonucleotide such as an antisense oligonucleotide. When the "nucleic acid medicine" is an antisense oligonucleotide, it may form a double-stranded oligonucleotide with a sequence capable of hybridizing.

The oligonucleotide of the complex of the present invention is an oligonucleotide, which is 8 to 50 bases, consisting of a sequence capable of hybridizing with the target sequence in the target gene. For example, it is 8 to 50 bases, 8 to 40 bases, 8 to 30 bases, 10 to 25 bases, and 15 to 25 bases.

When the oligonucleotide of the complex of the present invention is a double-stranded oligonucleotide, the second strand is an oligonucleotide, which is 8 to 60 bases, consisting of a sequence capable of hybridizing with the first strand consisting of a sequence capable of hybridizing with the target sequence in the target gene. For example, it is 8 to 60 bases, 8 to 50 bases, 8 to 40 bases, 8 to 30 bases, 10 to 25 bases, and 15 to 25 bases. The length of a second strand can be same with that of the first strand, and one or several nucleotide(s) shorter than that of the first strand as long as it can be hybridized with the first oligonucleotide. Furthermore, the length of a second strand can be longer than that of the first strand by adding one or several nucleotide(s) at one or both sides of a part hybridizing with the first strand.

"one or several base(s)" means one to ten, one to five, one to three, or one or two bases.

A preferable length of a second strand depends on the length of the first strand. For example, it is a length of 50% or more, 60% or more, 70% or more, 50 to 100%, 60 to 100% or 70 to 100% of the length of a first strand. A particularly preferred embodiment is 50 to 100% of the length of a first strand.

An oligonucleotide in the complex of the present invention includes the one comprising one or several mismatch(es) in a part of hybridization as long as it can be hybridized under a stringent condition with the target sequence in the target gene. For example, it is the oligonucleotide whose part for hybridization has at least 70% or more, preferably 80% or more, more preferably 90% or more, and most preferably 95% or more homology to the target sequence.

When an oligonucleotide in the complex of the present invention is a double-stranded oligonucleotide, an oligonucleotide of a second strand includes the one comprising one or several mismatch(es) in a part of hybridization as long as it can be hybridized under a stringent condition with a first strand capable of hybridizing with the target sequence in the target gene. For example, it is the oligonucleotide whose part for hybridization has at least 70% or more, preferably 80% or more, more preferably 90% or more, and most preferably 95% or more homology to the first strand.

The homology shows the similarity as a score, for example, by BLAST, a search program using algorithm discovered by Altschul et al. (The Journal of Molecular Biology, 215, 403-410 (1990).)

A "stringent condition" mean a condition under which a base sequence forms hybrid (so-called specific hybrid) with a specific sequence but any base sequence without the equivalent function does not form hybrid (so-called non-specific hybrid) with the specific sequences. People skilled in this field can easily select the condition by changing a temperature during hybridization reaction or washing, salt concentration in hybridization or washing buffer, or the like. In detail, an example of a stringent condition of the present invention is, but not limited to the condition, which the oligonucleotide is hybridized in 6×SSC (0.9 M NaCl, 0.09 M trisodium citrate) or 6×SSPE (3 M NaCl, 0.2 M $NaH_2PO_4$, 20 mM EDTA-2Na, pH 7.4) at 42° C. and then washed with 0.5×SSC at 42° C. As a hybridization method, well-known methods in this field, for example, southern blot hybridization or the like can be used. In detail, it can be performed according to a method disclosed in Molecular Cloning: A Laboratory Manual, Second Edition (1989) (Cold Spring Harbor Laboratory Press), Current Protocols in Molecular Biology (1994) (Wiley-Interscience), DNA Cloning 1: Core Techniques, A Practical Approach, Second Edition (1995) (Oxford University Press) or the like.

"One or several mismatch(es)" means one to five, preferably one to three, and more preferably one or two mismatch(es).

An "oligonucleotide" in the complex of the present invention is an oligonucleotide which nucleosides selected from the group consisting of DNA nucleosides, RNA nucleosides and nucleoside derivatives are bounded. All nucleosides can be same, or two or more kinds of nucleosides.

As a nucleoside derivative in an oligonucleotide in the complex of the present invention, any modification(s) for a nucleoside which is well-known in this field such as the above examples can be used.

A preferred embodiment is a nucleoside having a substituent at the 2' position of sugar and/or a nucleoside having a bridge structure between at the 4' and 2' positions of sugar.

As a substituent at the 2' position of a sugar, a preferred embodiment is F, $OCH_3$ or $OCH_2CH_2OCH_3$. $OCH_3$ is especially preferable.

As a bridge structure between the 4' and 2' positions of a sugar, a preferred embodiment is 4'-$(CH_2)$m'-O-2', wherein m' is an integer of 1 to 4, or 4'-C(=O)—$NR^{9'}$-2', wherein $R^{9'}$ is hydrogen atom or alkyl.

As an internucleoside linkage in the "oligonucleotide" in the complex of the present invention, any well-known internucleoside linkage such as the above examples in this field can be used. All internucleoside linkages can be same, or two or more kinds of linkages. A preferred embodiment is D-oligo and/or S-oligo.

The oligonucleotides in the complex of the present invention can be synthesized according to the usual methods in this field. For example, they can be easily synthesized by an automated nucleic acid synthesizer which is commercially available (e.g., the synthesizer by Applied Biosystems and Dainippon Seiki). A method for synthesizing is solid-phase synthesis using phosphoramidites, solid-phase synthesis using hydrogen phosphonates or the like. Examples are disclosed in the following Example 1, Tetrahedron Letters 22, 1859-1862 (1981) and the like.

When an oligonucleotide in the complex of the present invention is a double-stranded oligonucleotide, the synthesized first strand and second strand form a double-stranded oligonucleotide by hybridizing according to the well-known method. Examples are disclosed in the following Example 1 Example 1 in WO2013/089283 and the like.

In the complex of the present invention, the lipid binds through a linker to the oligonucleotide.

The "lipid" for the complex of the present invention is a lipid of a group of the formula:

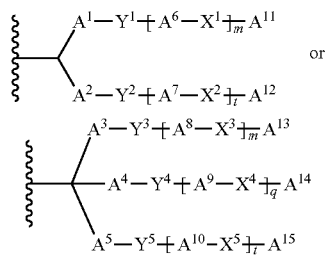

wherein
$A^{11}$ is substituted or unsubstituted alkyl, substituted or unsubstituted alkenyl, substituted or unsubstituted alkynyl or a group of the formula:

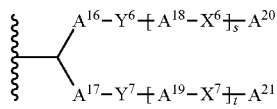

$A^1$ to $A^{10}$ and $A^{16}$ to $A^{19}$ are each independently a bond, substituted or unsubstituted alkylene, substituted or unsubstituted alkenylene, or substituted or unsubstituted alkynylene,
when $A^1$ and $A^2$ or $A^{16}$ and $A^{17}$ are substituted or unsubstituted alkylene, substituted or unsubstituted alkenylene, or substituted or unsubstituted alkynylene or
any carbon atom of $A^1$ and any carbon atom of $A^2$, or any carbon atom of $A^{16}$ and any carbon atom of $A^{17}$ taken together may form substituted aromatic carbocycle or substituted non-aromatic carbocycle,
$Y^1$ to $Y^7$ are each independently a bond or O,
$X^1$, $X^3$ and $X^6$ are each independently $NR^1C(=O)$, $C(=O)NR^1$, $R^2C(=O)NR^1$ or $NR^1C(=O)R^2$,
$X^2$, $X^4$, $X^5$ and $X^7$ are each independently a bond, $NR^3C(=O)$, $C(=O)NR^3$, $R^4C(=O)NR^3$, $NR^3C(=O)R^4$ or S—S,
$R^2$ and $R^4$ are each independently O or $NR^5$, $R^1$, $R^3$ and $R^5$ are each independently hydrogen, substituted or unsubstituted alkyl, substituted or unsubstituted alkenyl, or substituted or unsubstituted alkynyl,
$A^{12}$ and $A^{14}$ is substituted or unsubstituted alkyl, substituted or unsubstituted alkenyl, substituted or unsubstituted alkynyl, or a group comprising a fat-soluble compound,
$A^{13}$, $A^{15}$, $A^{20}$ and $A^{21}$ are each independently substituted or unsubstituted alkyl, substituted or unsubstituted alkenyl, or substituted or unsubstituted alkynyl,
m, n, p, q, r, s and t are each independently 1 or 2.
provided that a substituent for the alkyl, alkenyl, alkynyl, alkylene, alkenylene and alkynylene is halogen, hydroxy, carboxy, amino, imino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, aromatic carbocyclyl, non-aromatic carbocyclyl, non-aromatic heterocyclyl, non-aromatic heterocyclyl, aromatic carbocyclylcarbonyl, non-aromatic carbocyclylcarbonyl, aromatic heterocyclylcarbonyl or non-aromatic heterocyclylcarbonyl, and may have any one or more substituent(s) selected from Group α.

Group α: hydroxy, alkyl, alkyloxy, mercapto, alkylthio, amino, alkylamino and halogen.

$A^1$ and $A^2$ are substituted or unsubstituted alkylene, substituted or unsubstituted alkenylene or substituted or unsubstituted alkynylene, and "any carbon atom of $A^1$ and any carbon atom of $A^2$ taken together form substituted aromatic carbocycle or substituted non-aromatic carbocycle" means a group of the following left formula.

Also, $A^{16}$ and $A^{17}$ are substituted or unsubstituted alkylene, substituted or unsubstituted alkenylene or substituted or unsubstituted alkynylene, and "any carbon atom of $A^{16}$ and any carbon atom of $A^{17}$ taken together form substituted aromatic carbocycle or substituted non-aromatic carbocycle" means a group of the following right formula.

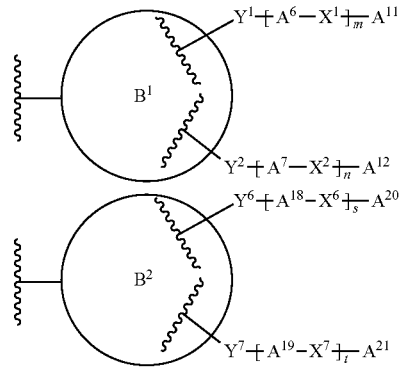

wherein ring $B^1$ or ring $B^2$ is substituted or unsubstituted aromatic carbocycle or substituted or unsubstituted non-aromatic carbocycle, and the other symbols has the same meaning as above. A group of the formula: $Y^1$-$[A^6$-$X^1]$m-$A^{11}$ and a group of the formula: $Y^2$-$[A^7$-$X^2]$n-$A^{12}$ bind to the different carbon atoms on ring $B^1$, and one or more of any substituent selected from the above γ group may be at the other carbon atom on ring $B^1$. A group of the formula: $Y^6$-$[A^{18}$-$X^6]$s-$A^{20}$ and a group of the formula: $Y^7$-$[A^{19}$-$X^7]$t-$A^{21}$ bind to the different carbon atoms on ring $B^2$, and one or more of any substituent selected from the above γ group may be at the other carbon atom on ring $B^2$. A group of the formula: $Y^6$-$[A^{18}$-$X^6]$s-$A^{20}$ and a group of the formula:

Y⁷-[A¹⁹-X⁷]t-A²¹ bind to the different carbon atoms on ring B², and one or more of any substituent selected from the above γ group may be at the other carbon atom on ring B¹.

As Ring B¹ or Ring B², a particularly preferred embodiment is phenyl.

As A¹ to A¹⁰ and A¹⁶ to A¹⁹, a particularly preferred embodiment is a bond or unsubstituted alkylene.

As X¹, X³ and X⁶, a particularly preferred embodiment is NHC(=O) or NHC(=O)NH.

As X², X⁴, X⁵ and X⁷, a particularly preferred embodiment is a bond or NHC(=O).

"A fat-soluble compound" is not limited as long as it is well-known a fat-soluble compound in this field. Examples include fat-soluble vitamins such as vitamin E, vitamin A, vitamin B, β-carotene, vitamin D and/or vitamin K (e.g., tocopherol and folic acid), crotamiton, teprenone, indometacin, prednisolone and tannic acid.

As a group comprising a fat-soluble compound, a preferred embodiment is a group comprising tocopherol, folic acid or cRGD.

A group comprising tocopherol means the following.

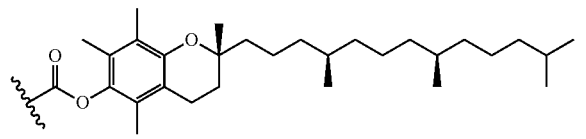 [SMILES: *C(=O)Oc1c(C)c(C)c2c(c1C)CC[C@@](C)(CCC[C@H](C)CCC[C@H](C)CCCC(C)C)O2]

A group comprising folic acid means the following.

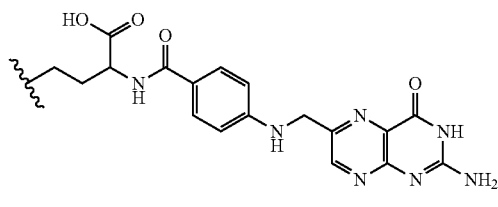 [SMILES: *CCC(NC(=O)c1ccc(NCc2cnc3nc(N)[nH]c(=O)c3n2)cc1)C(=O)O]

A group comprising cRGD means the following.

When A¹¹ to A¹⁵, A²⁰ and A²¹ are substituted or unsubstituted alkyl, substituted or unsubstituted alkenyl, or substituted or unsubstituted alkynyl, alkyl, alkenyl or alkynyl is preferably C6 to C30 and more preferably C6 to C24, and may be branched. The length of each A¹¹ and A¹², A¹³ to A¹⁵ or A²⁰ and A²¹ may be same or different.

As A¹¹ and A¹³, a particularly preferred embodiment is unsubstituted alkyl.

As A¹² and A¹⁴, a particularly preferred embodiment is substituted or unsubstituted alkyl, substituted or unsubstituted alkenyl or a group comprising a fat-soluble compound.

As m, n, p, q, r, s and t, a particularly preferred embodiment is 1.

As the "lipid", particularly preferred embodiments are the followings.

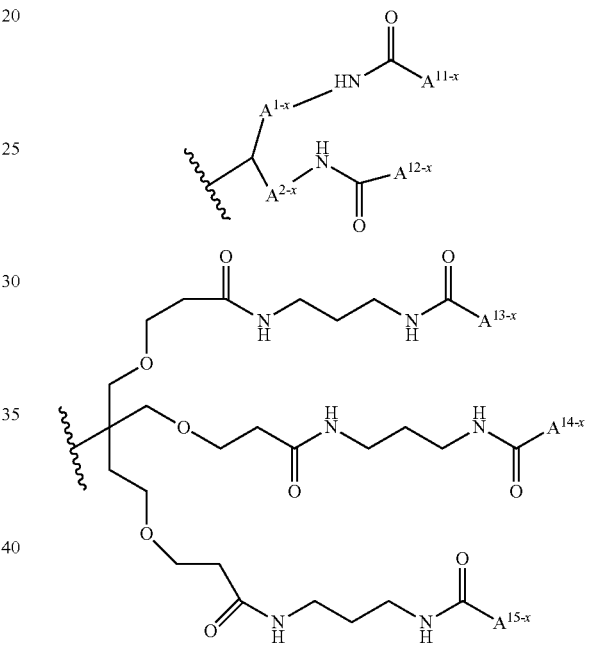

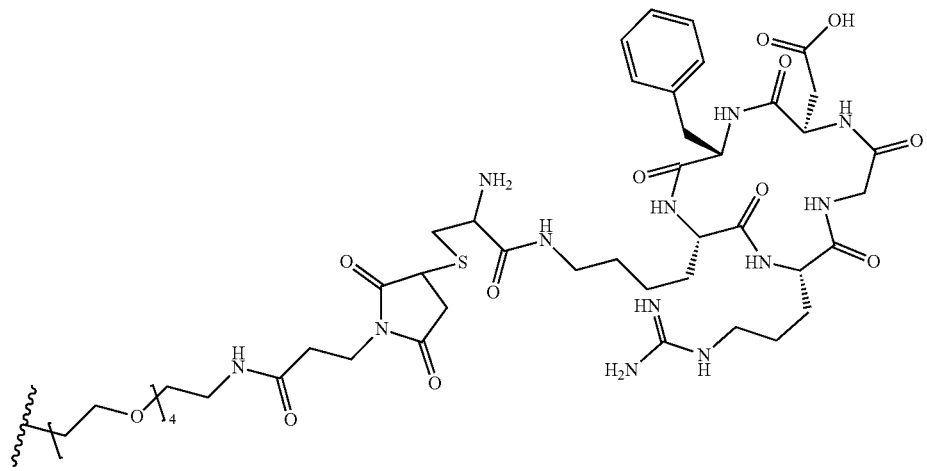

-continued

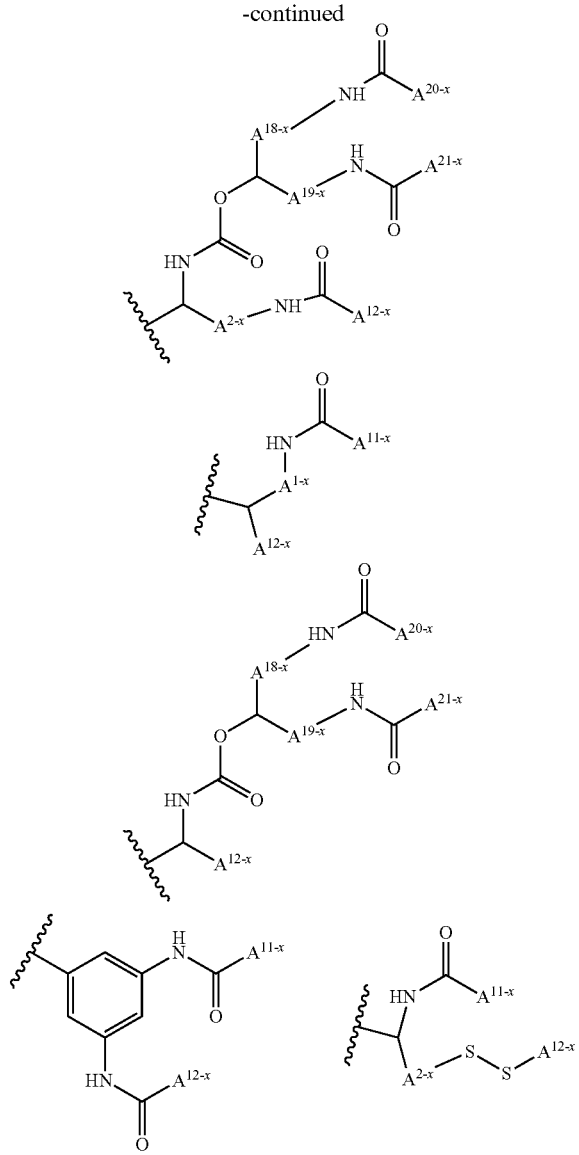

wherein $A^{1\text{-}X}$, $A^{2\text{-}X}$, $A^{18\text{-}X}$ and $A^{19\text{-}X}$ are alkylene, $A^{11\text{-}X}$, $A^{13\text{-}X}$, $A^{15\text{-}X}$, $A^{20\text{-}X}$ and $A^{21\text{-}X}$ are alkyl, and $A^{12\text{-}X}$ and $A^{14\text{-}X}$ are substituted or unsubstituted alkyl, or a group comprising a fat-soluble compound.

In the complex of the present invention, lipid can bind through a linker to at least one or more position(s) selected from at the 3'-end, at the 5'-end or in the strand of the oligonucleotide. The lipid preferably binds at one or two position(s) in the oligonucleotide. When an oligonucleotide in the complex of the present invention is a double-stranded oligonucleotide, the lipid preferably binds to the second strand. A particularly preferred embodiment is that the lipid binds at the 3'-end and/or the 5'-end of the second strand.

When a lipid binds at the 5'-end of an olgonucleotide, for example, it can bind in the following manner.

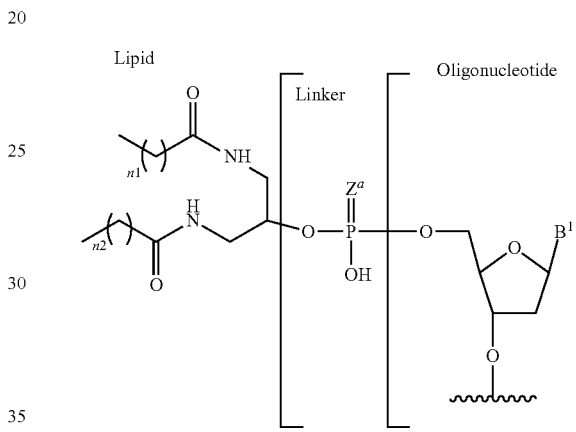

wherein $B^1$ is a base at the 3'-end of an oligonucleotide, $Z^a$ is O or S, n1 or n2 are each independently an integer of 5 to 29, and preferably each independently and integer of 10 to 18.

When a lipid binds at the 3'-end of an oligonucleotide, for example, it can bind in the following manner.

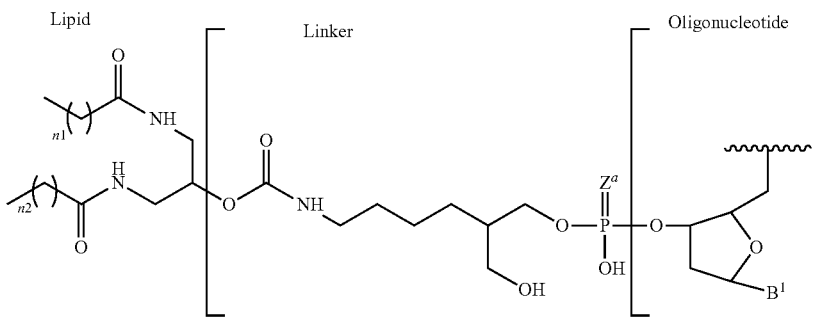

wherein
B¹ is a base at the 5'-end of an oligonucleotide,
$Z^a$ is O or S,
n1 or n2 are each independently an integer of 5 to 29, and preferably each independently an integer of 10 to 18.

When a lipid binds in the strand of an oligonucleotide, for example, it can bind in the following manner.

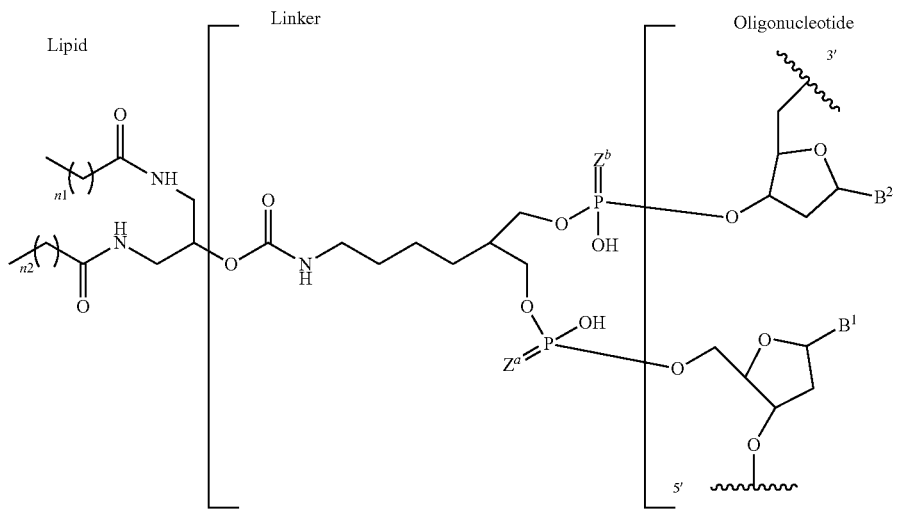

wherein
B¹ and B² are neighboring bases in an oligonucleotide,
$Z^a$ or $Z^b$ are each independently O or S,
n1 or n2 are each independently an integer of 5 to 29, and preferably each independently an integer of 10 to 18.

The lipid can be synthesized in reference to well-known methods in this field. Examples of the lipid or the preparation methods are disclosed in the following Example 1, Non-patent Document 3 and the like.

In the complex of the present invention, the lipid binds through a linker to an oligonucleotide. As a "linker", any linker used in this field can be used.

Examples are the followings.

A group of the formula:

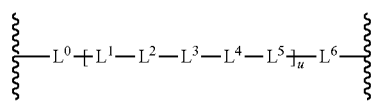

wherein
$L^0$ binds to the oligonucleotide and $L^6$ binds to lipid.
$L^0$ is a bond, a nucleotide linker or non-nucleotide linker,
$L^1$ is a group of the formula:

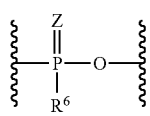

wherein Z are each independently O or S, and $R^6$ are each independently hydroxy, alkyl or alkyloxy,
$L^2$ and $L^4$ are each independently a bond or substituted or unsubstituted C1 to C20 alkylene, $L^3$ are each independently a bond; C(=O)NR⁷, wherein R⁷ is hydrogen or substituted or unsubstituted alkyl; NR⁸C(=O), wherein R⁸ is hydrogen, substituted or unsubstituted alkyl or R⁸ and a carbon atom in alkylene of $L^2$ taken together may form substituted or unsubstituted nitrogen-containing ring; or S—S, $L^5$ are each independently a bond, substituted or unsubstituted C1 to C20 alkylene, C(=O)NR⁹, NR⁹C(=O), NR⁹, O or substituted or unsubstituted non-aromatic heterocyclyl,
R⁹ are each independently hydrogen, substituted or unsubstituted alkyl, substituted or unsubstituted alkenyl, or substituted or unsubstituted alkynyl,
u is 1 or 2, and
$L^6$ is a bond or amino acid linker.

"A nucleotide linker" is a linker consisting of an oligonucleotide which nucleosides selected from the group consisting of DNA nucleosides, RNA nucleosides and nucleoside derivatives are bounded. All nucleosides can be same, or two or more kinds of nucleosides.

The length of a nucleotide linker is 1 to 10 bases, 2 to 8 bases, 4 bases, 5 bases, 6 bases and 7 bases. Examples are the following linkers.

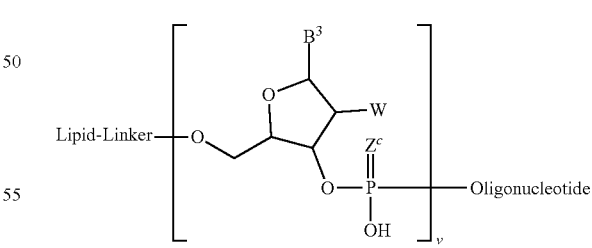

wherein
B³ is adenine (A), guanine (G), cytosine (C), 5-methylcytosine (5-Me-C), thymine (T) or uracil (U). Furthermore, B³ may be absent (Ab).
W are each independently H or OH, and preferably H.
$Z^e$ are each independently O or S.
v is an integer of 1 to 10.

A particularly preferred embodiment is that B³ is adenine or thymine; $Z^e$ is O; and v is 1 to 9.

Examples of a "non-nucleotide linker" include a linker which one to several alkanediol(s) (e.g., butanediol) are bounded, and a linker which one to several ethylene glycol(s) (e.g., triethylene glycol, hexaethylene glycol) are bounded.

"One to several" means 1 to 10, 1 to 8, 5, 6 or 7.

A preferred embodiment is a linker which 3 to 9 butanediols are bounded.

When $L^3$ is $NR^8C(=O)$, "$R^8$ and a carbon atom in alkylene of $L^2$ taken together may form substituted or unsubstituted nitrogen-containing ring" means the following.

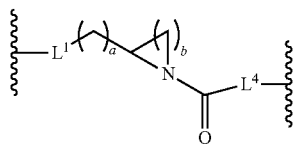

wherein a is an integer of 0 to 18, and b is an integer of 1 to 5. Alkylene may have one or more of any substituent selected from the above β group. A nitrogen-containing ring may have one or more of any substituent selected from the above γ group.

Examples are the followings.

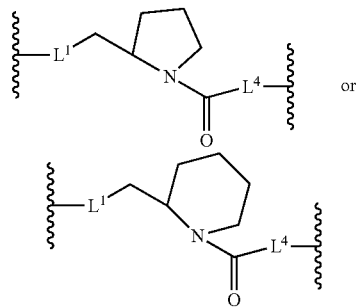

When $L^5$ is "substituted or unsubstituted non-aromatic heterocyclyl", a preferred embodiment is succinimide. It may have one or more of any substituent selected from the above γ group.

An "amino acid linker" means a linker derived from one or more amino acid(s). Any amino acid which is well-known in this field can be used as the amino acid. A preferred embodiment is a linker consisting of 2 to 10 amino acids. Examples include a linker derived from Lys-Ala-Ala-Cys-Trp (SEQ ID NO: 14, Compound 101) or Lys-Val-Lys-Cys-Trp (SEQ ID NO: 15, Compound 102) synthesized in the following A) of Example 1.

As $L^1$, a preferred embodiment is

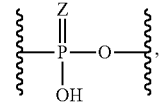

wherein Z is O or S.

As $L^2$, a preferred embodiment is substituted or unsubstituted C1 to C20 alkylene.

As $L^3$, a particularly preferred embodiment is a bond; $C(=O)NH$; or $NR^8C(=O)$, wherein $R^8$ and a carbon atom in alkylene of $L^2$ taken together may form substituted or unsubstituted nitrogen-containing ring.

As $L^5$, a particularly preferred embodiment is a bond, $C(=O)NH$, NH or O.

As

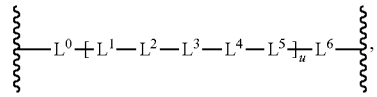

particularly preferred embodiments are the followings.

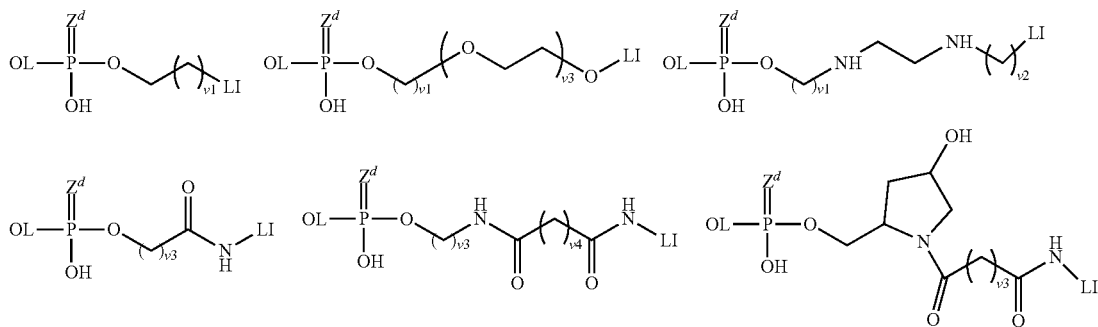

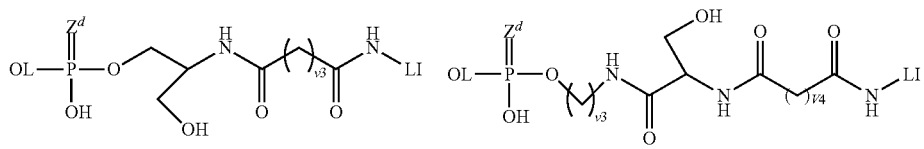

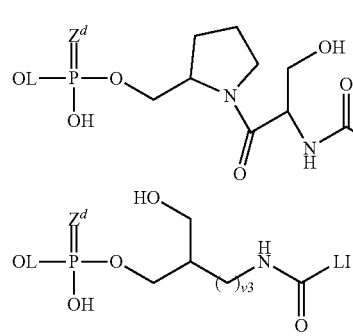
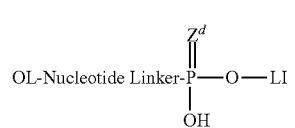
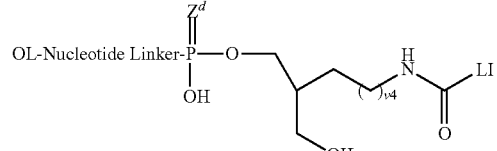
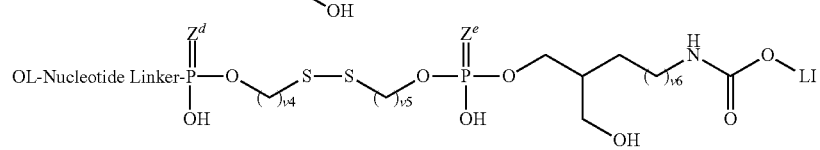
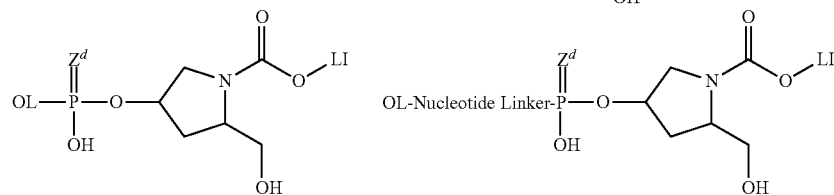
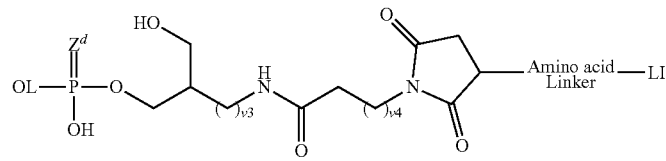

wherein
OL means that it binds to an oligonucleotide having suppressing activity of the target gene expression,
LI means that it binds to the lipid,
$Z^d$ and $Z^e$ are each independently O or S.
v1 or v2 are each independently an integer of 0 to 10, preferably each independently an integer of 0 to 5, and more preferably each independently an integer of 0 to 3.
v3 to v6 are each independently an integer of 1 to 4, preferably each independently an integer of 1 to 3, and more preferably each independently 2 or 3.
"Nucleotide Linker" and "Amino acid Linker" has the same meaning as above.

Examples of "a linker" or the preparation methods are disclosed in the above Patent Document 6, Patent Document 10 or the like.

"Lipid" and linker are synthesized as a compound comprising a lipid and a part of a linker, the compound is supported on a resin and introduced to an oligonucleotide to obtain "a complex" of the present invention as the following Example 1. When an oligonucleotide in the complex of the present invention is a double-stranded oligonucleotide, after that, the other oligonucleotide is hybridized to obtain "a complex" of the present invention. Examples of "A compound comprising a lipid and a part of a linker" include the compounds described in the following Example 1.

For "a complex" of the present invention, the 3'-end or the 5'-end without binding a lipid of an oligonucleotide, or a linker can be further modified. To be capable of tracking of the oligonucleotide, to improve pharmacokinetics or pharmacodynamics of the oligonucleotide, or to enhance the stability or binding affinity of the oligonucleotide, the well-known modified group in this field can be used. Examples include a protecting group of a hydroxyl group, reporter molecule, cholesterol, phospholipid, pigment and fluorescent molecule.

Furthermore, for "a complex" of the present invention, the 3'-end or the 5'-end without binding a lipid of an oligonucleotide may comprise a phosphate ester. The "phosphate ester" means a phosphate group at the end comprising phosphate ester or modified phosphate ester. Although the phosphate ester moiety may be at the either end, a preferred embodiment is at the 5'-end nucleoside. Examples include a group of the formula: —O—P(=O)(OH)OH and the modified group. That is, one or more of O or OH is optionally substituted with H; O; OR'; S; N(R'), wherein R' is H, amino-protecting group, or substituted or unsubstituted alkyl; or alkyl. The 5'-end or the 3'-end may each independently comprise substituted or unsubstituted 1 to 3 phosphate moiety.

The present invention encompasses a pharmaceutical composition in the complex of the present invention or a compound specifically described in the following Examples, which is the complex of the present invention.

As the following examples, a pharmaceutical composition of the present invention has any or all of the following excellent characteristics:
a) Enhancement of suppressing activity of the target gene expression of a nucleic acid medicine in the complex of the present invention
b) High metabolic stability.
c) Weak CYP enzyme (e.g., CYP1A2, CYP2C9, CYP2C19, CYP2D6 and CYP3A4) inhibition.
d) Good pharmacokinetics such as a high bioavailability and moderate clearance.
e) No mutagenicity.
f) Low cardiovascular risk.
g) High solubility.
h) Low acute toxicity risk.

In an oligonucleotide in the complex of the present invention, a nucleoside(s) or an internucleoside linkage(s) may be modified. An oligonucleotide with an appropriate modification(s) has any or all of the following characteristics compared to an oligonucleotide without a modification(s):
a) High affinity of a nucleic acid medicine comprising the complex of the present invention to the target gene
b) High resistibility to nuclease.
c) Improvement of the drug disposition.
d) High transitivity into tissue.

Any administration method and formulation for a pharmaceutical composition of the present invention can be used if it is a well-known administration method and formulation in this field.

A pharmaceutical composition of the present invention may be administered in a number of ways depending upon whether local or systemic treatment is desired and upon the area to be treated. Examples of an administration method include topical (including ophthalmic, intravaginal, intrarectal, intranasal and transdermal), oral and parenteral. Examples of parenteral administration include intravenous injection or drip, subdermal, intraperitoneal or intramuscular injection, lung administration by aspiration or inhalation, intrathecal administration and intraventricular administration. A preferred embodiment is intravenous injection or subcutaneous administration.

When a pharmaceutical composition of the present invention is topically administered, a formulation such as a transdermal patch, ointment, lotion, cream, gel, drop, suppository, spray, liquid and powder can be used.

Examples of the composition for oral administration include powder, granule, suspension or solution dissolved in water or non-aqueous vehicle, capsule, powder and tablet.

Examples of the composition for parenteral, intrathecal or intraventricular administration include sterile aqueous solutions which contain buffers, diluents and other suitable additives.

A pharmaceutical composition of the present invention can be obtained by mixing an effective amount with various pharmaceutical additives suitable for the administration form, such as excipients, binders, moistening agents, disintegrants, lubricants and diluents as needed. When the composition is an injection, it together with a suitable carrier can be sterilized to obtain a composition.

Examples of the excipients include lactose, saccharose, glucose, starch, calcium carbonate and crystalline cellulose.

Examples of the binders include methylcellulose, carboxymethylcellulose, hydroxypropylcellulose, gelatin and polyvinylpyrrolidone.

Examples of the disintegrants include carboxymethylcellulose, sodium carboxymethylcellulose, starch, sodium alginate, agar and sodium lauryl sulfate.

Examples of the lubricants include talc, magnesium stearate and macrogol. Cacao oil, macrogol, methylcellulose or the like may be used as base materials of suppositories.

When the composition is prepared as solutions, emulsified injections or suspended injections, solubilizing agents, suspending agents, emulsifiers, stabilizers, preservatives, isotonic agents and the like which are usually used may be added as needed. For oral administration, sweetening agents, flavors or the like may be added.

Dosing of a pharmaceutical composition of the present invention is dependent on severity and responsiveness of the disease state to be treated, with the course of treatment lasting from several days to several months, or until a cure is affected or a diminution of the disease state is achieved. Optimal dosing schedules can be calculated from measurements of drug accumulation in the body. Persons of ordinary skill in the art can easily determine optimal dosages, dosing methodologies and repetition rates. Optimal dosages can be generally calculated based on IC50 or EC50 in vitro or in vivo animal experiments although they change according to relative efficacy of a nucleic acid medicine in the complex of the present invention. Dosages shown as mg/kg are calculated according to the usual method when, for example, a molecular weight of a nucleic acid medicine (derived from the sequences and chemical structures) and the effective dosage such as IC50 (derived from experiments) are provided.

In order to improve suppressing activity of the target gene expression of a nucleic acid medicine, a pharmaceutical composition of the present invention can be used together with an appropriate nucleic acid medicine for the prevention or treatment of various diseases in which the effect of the nucleic acid medicine is expected.

In this description, meaning of each abbreviation is as follows:
CPG: Controlled Pore Glass
DIEA: N, N-diisopropylethylamine
DMAP: 4-dimethylaminopyridine
DMEM: Dulbecco's Modified Eagle's Medium
DMF: N, N-dimethylformamide
DMSO: dimethyl sulfoxide
DMTr: dimethoxytrityl
Fmoc: 9-fluorenylmethyloxycarbonyl
HBTU: O-benzotriazole-N, N, N', N'-tetramethyluronium-hexafluoro-phosphate
NMP: N-methylpyrrolidone
PBS: phosphate buffered saline
TBS: tert-butyldimethylsilyl
TBAF: tetrabutylammonium fluoride
TFA: trifluoroacetic acid
THF: tetrahydrofuran

EXAMPLES

The present invention will be described in more detail with reference to, but not limited to, the following Examples, Reference Examples and Test Examples.

NMR analysis of each compound obtained in Examples was performed by 300 MHz or 400 MHz using $CD_3OD$, $CDCl_3$ or DMSO-d6.

UPLC analysis was performed under the following conditions.

1) ODS Acid Analysis
Mobile phases: [A] is 0.1% aqueous formic acid solution, and [B] is acetonitrile solution containing 0.1% formic acid
Gradient: linear gradient of 5%-100% Solvent [B] for 3.5 minutes was performed, and 100% Solvent [B] was maintained for 0.5 minute.
Column: ACQUITY UPLC (Registered Trademark) BEH C18 (1.7 μm, i.d. 2.1×50 mm) (Waters)
Flow rate: 0.8 mL/min
PDA detection wavelength: 254 nm (Detection range 210-500 nm)

2) ODS Base Analysis
Mobile phases: [A] is 10 mM aqueous ammonium carbonate solution, and [B] is acetonitrile
Gradient: linear gradient of 5%-100% Solvent [B] for 3.5 minutes was performed, and 100% Solvent [B] was maintained for 0.5 minute.
Column: ACQUITY UPLC (Registered Trademark) BEH C18 (1.7 μm, i.d. 2.1×50 mm) (Waters)
Flow rate: 0.8 mL/min
PDA detection wavelength: 254 nm (Detection range 210-500 nm)

3) C4 Base Analysis
Mobile phases: [A] is 10 mM aqueous ammonium carbonate solution and [B] is acetonitrile
Gradient: linear gradient of 60%-100% Solvent [B] for 3.5 minutes was performed, and 100% Solvent [B] was maintained for 0.5 minute.
Column: Xbridge Protein BEH C4 (3.5 μm, i.d. 2.1×50 mm) (Waters)
Flow rate: 0.8 mL/min
PDA detection wavelength: 254 nm (Detection range 210-500 nm)

Example 1 Synthesis of the Complex of the Present Invention

A) Synthesis of Lipids
1) Synthesis of 5-n'

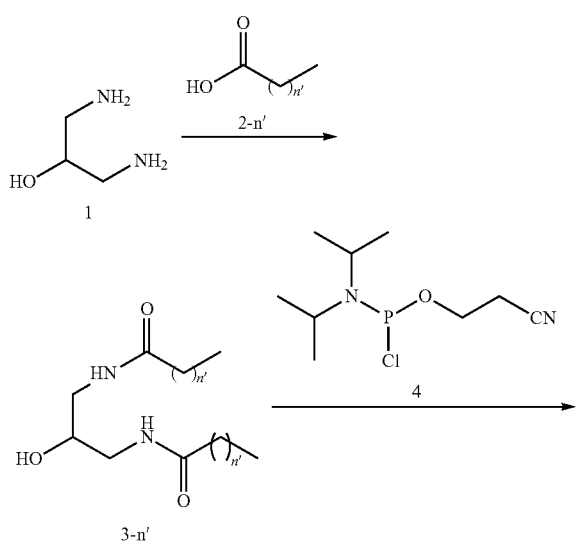

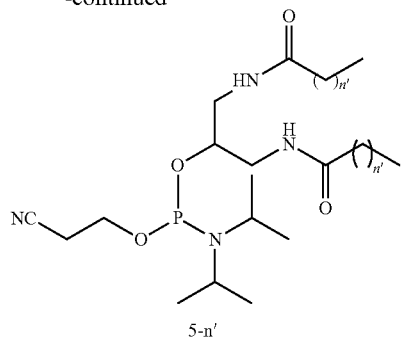

wherein n' is an integer of 5 to 29.

1-1) Synthesis of Compound 5-12
Step 1

Compound 2-12 (5.07 g, 22.19 mmol, Tokyo Chemical Industry Co., Ltd.) was dissolved in DMF (51.8 mL) and dichloromethane (28.6 mL). DIEA (5.81 mL, 33.3 mmol) and HBTU (9.26 g, 24.4 mmol) were added thereto, and the mixture was vigorously stirred at room temperature for 30 minutes. To the resulting white suspended solution, Compound 1 (1.0 g, 11.1 mmol) was added at room temperature, and the mixture was vigorously stirred. Then, the mixture was heated to 40° C., and then stirred for two hours. To the reaction mixture was added aqueous saturated sodium bicarbonate solution (10 mL) to stop the reaction. The resulting white solid was collected by filtration. The resulting solid was washed with water (50 mL), acetonitrile (50 mL) and dichloromethane (50 mL) to obtain Compound 3-12 (4.8 g, 9.4 mmol) as white solid.

$^1$H-NMR ($CDCl_3$):6.20 (2H, brs), 3.96 (1H, d, J=4.0 Hz), 3.75 (1H, m), 3.40 (2H, dd, J=4.0, 12.0 Hz), 3.25 (2H, dd, J=4.0, 12.0 Hz), 2.22 (4H, t, J=12.0 Hz), 1.62 (4H, d, J=8.0 Hz), 1.29-1.25 (40H, m), 0.90-0.86 (6, m)

ESI-MS (m/z): 512 (M+1).

Step 2

Compound 3-12 (5.10 g, 9.98 mmol) was suspended in dichloromethane (257 mL), and DIEA (6.97 mL, 39.9 mmol) was added thereto. Then, Compound 4 (4.46 mL, 20.0 mmol) was added at room temperature, and the mixture was heated under reflux for two hours. After cooling to room temperature, the reaction mixture was transferred to a separatory funnel, and the organic layer was washed twice with aqueous saturated sodium bicarbonate solution (100 mL), twice with water (100 mL), and once with brine (100 mL). After the resulting organic layer was dried over magnesium sulfate, the solvent was distilled off under reduced pressure. The resulting brown oil, Compound 5-12 (4.80 g, 6.75 mmol) was obtained as a crude product. Formation of the compound was determined based on introduction of trivalent phosphorus by $^{31}$P-NMR.

$^{31}$P-NMR($CDCl_3$)δ:148.2 (s)

2) Synthesis of Compound 8

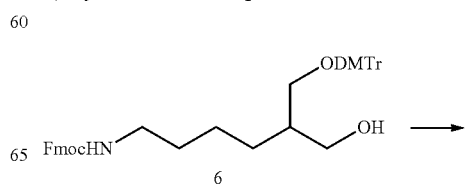

-continued

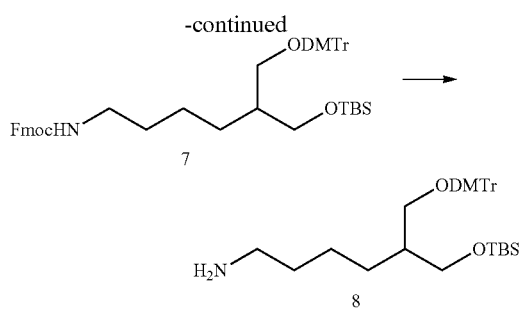

To Compound 6 (see US2014/0142253, 292 mg, 0.435 mmol) in DMF solution (2.0 mL), imidazole (71 mg, 1.044 mmol) and t-butylchlorodimethylsilane (79 mg, 0.522 mmol) were added, and the mixture was stirred at room temperature for 16 hours. The reaction mixture was diluted with water and extracted with cyclopentyl methyl ether. The organic layer was washed with water and brine, and then dried over sodium sulfate. The solvent was distilled off under reduced pressure to obtain the crude product of Compound 7 (352 mg).

To the crude product of Compound 7 (352 mg) in dichloromethane solution (2.4 mL), diethylamine (0.6 mL, 5.74 mmol) was added, and the mixture was stirred at room temperature for 16 hours. After ethanol was added to the reaction mixture, the solvent was distilled off under reduced pressure. The residue was coevaporated twice with ethanol, and the resulting crude product was purified by amino silica gel column chromatography (chloroform) to obtain Compound 8 (190 mg, 78%) as colorless oil.

$^1$H-NMR (CDCl$_3$) δ: 7.45-7.43 (2H, m), 7.32 (4H, d, J=8.8 Hz), 7.29-7.25 (2H, m), 7.22-7.18 (1H, m), 6.81 (4H, d, J=8.8 Hz), 3.79 (6H, s), 3.68-3.61 (2H, m), 3.08-3.02 (2H, m), 2.63 (2H, t, J=7.2 Hz), 1.75-1.69 (1H, m), 1.41-1.30 (6H, m), 1.27-1.15 (2H, m), 0.84 (9H, s), 0.01 (6H, s).

3) Synthesis of Compound 13-n'

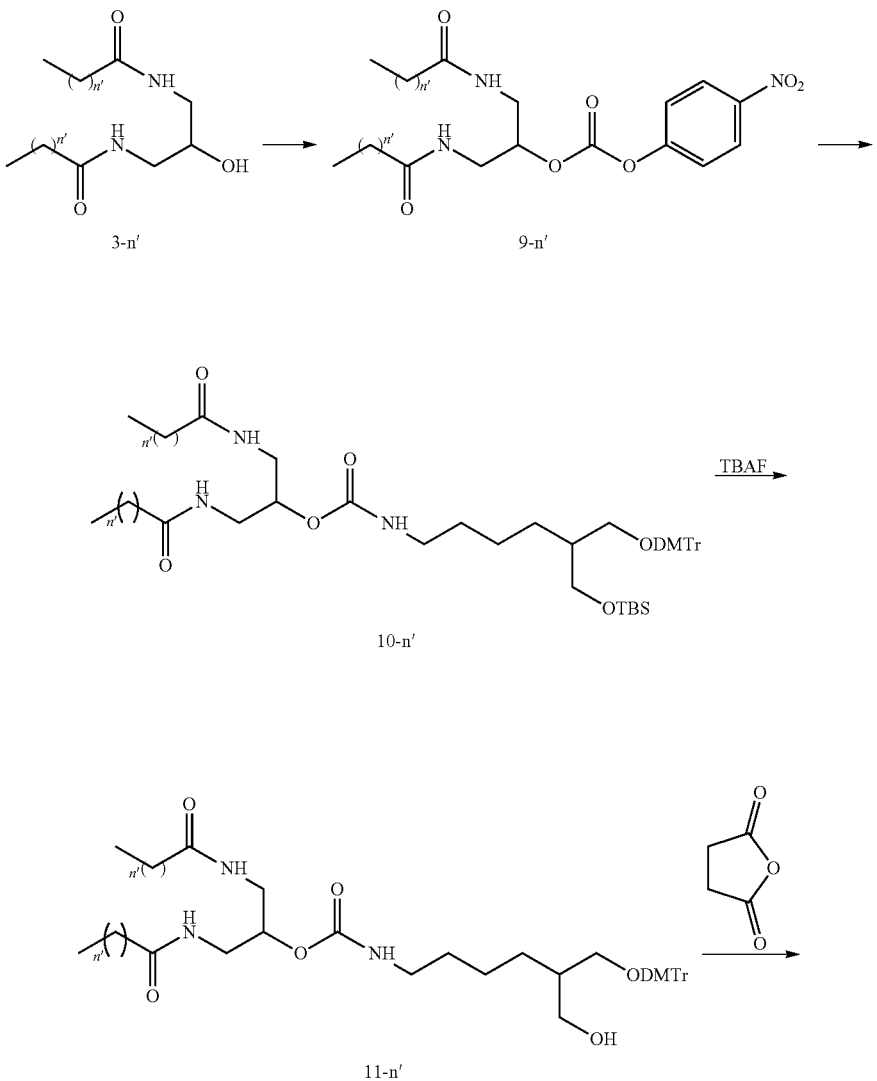

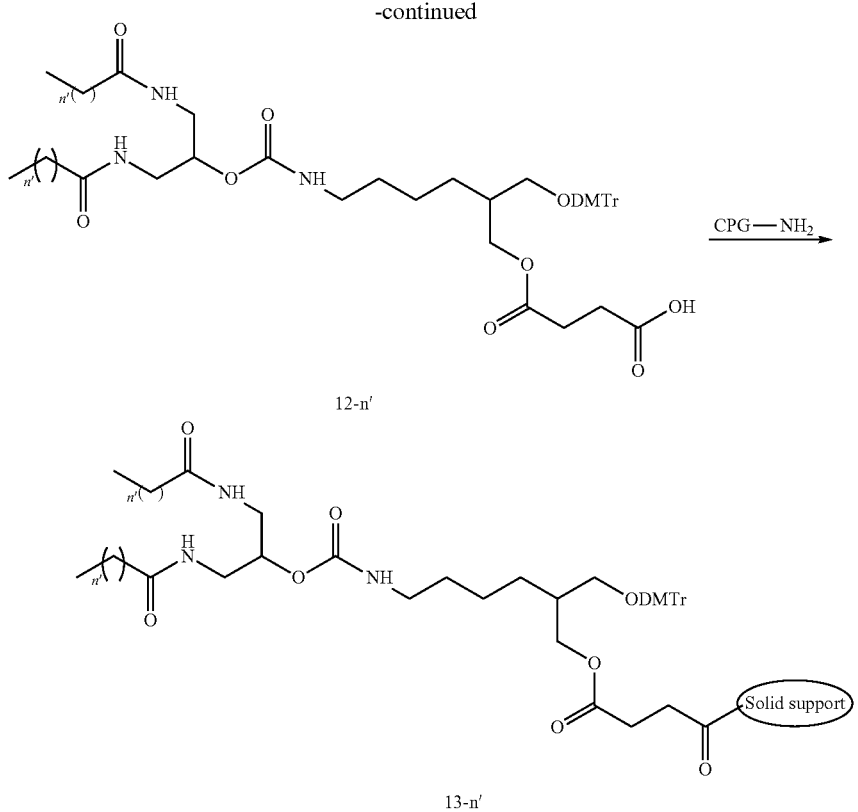

12-n'

13-n' wherein n' is an integer of 5 to 29.

3-1) Synthesis of Compound 13-6

Step 1

To Compound 3-6 (1.0 g, 2.92 mmol) in THF (20 mL)-chloroform (20 mL) solution, DIEA (1.53 mL, 8.76 mmol), bis(nitrophenyl) carbonate (1.33 g, 4.38 mmol) and DMAP (178 mg, 1.46 mmol) were added, and the mixture was stirred at 60° C. for one hour. The reaction mixture was filtered. After the mother liquid was distilled off under reduced pressure, the resulting crude product was purified by silica gel column chromatography (hexane:ethyl acetate=60:40→20:80) to obtain Compound 9-6 (982 mg, 66%) as a white solid.

$^1$H-NMR (CDCl$_3$) δ: 8.32-8.26 (2H, m), 7.42 (2H, dt, J=9.9, 2.5 Hz), 6.36 (2H, t, J=6.4 Hz), 4.80 (1H, ddd, J=10.7, 5.6, 3.3 Hz), 3.65-3.50 (4H, m), 2.26 (4H, t, J=7.6 Hz), 1.69-1.62 (4H, m), 1.28 (16H, dt, J=19.1, 4.7 Hz), 0.87 (6H, t, J=6.8 Hz).

Step 2

To Compound 8 (500 mg, 0.89 mmol) in dichloromethane solution (10.0 mL), Compound 9-6 (450 mg, 0.89 mmol) was added, and the mixture was stirred at room temperature for two hours. The reaction mixture was concentrated under reduced pressure and purified by amino silica gel column chromatography (hexane:ethyl acetate=65:35→10:90) to obtain Compound 10-6 (625 mg, 76%) as colorless oil.

$^1$H-NMR (CDCl$_3$) δ: 7.42 (2H, d, J=7.4 Hz), 7.31 (4H, t, J=6.2 Hz), 7.26 (3H, t, J=3.9 Hz), 7.19 (1H, t, J=7.2 Hz), 6.82 (4H, t, J=6.0 Hz), 6.25 (2H, t, J=5.8 Hz), 4.70 (2H, dd, J=10.3, 5.3 Hz), 3.79 (6H, d, J=4.4 Hz), 3.62 (2H, dd, J=10.1, 5.1 Hz), 3.51 (2H, dd, J=13.3, 6.4 Hz), 3.32-3.26 (2H, m), 3.08 (4H, dt, J=20.2, 6.6 Hz), 2.19 (4H, t, J=7.7 Hz), 1.70 (1H, t, J=5.7 Hz), 1.61 (8H, t, J=9.3 Hz), 1.42 (2H, t, J=7.3 Hz), 1.26 (20H, tt, J=26.0, 10.5 Hz), 0.88 (6H, dd, J=12.0, 5.3 Hz), 0.83 (9H, s).

Step 3

To Compound 10-6 (625 mg, 0.67 mmol) in THF solution (10 mL), TBAF (1M THF solution, 1.34 mL, 1.34 mmol) was added, and the mixture was stirred at room temperature for 24 hours. The reaction mixture was concentrated under reduced pressure, and the resulting crude product was purified by diol silica gel column chromatography (hexane:ethyl acetate=50:50→10:90) to obtain Compound 11-6 (541 mg, 99%) as colorless liquid.

$^1$H-NMR (CDCl$_3$) δ: 7.41 (2H, t, J=4.3 Hz), 7.26 (9H, ddt, J=31.6, 12.0, 4.9 Hz), 6.83 (4H, d, J=8.8 Hz), 6.38 (2H, q, J=6.1 Hz), 4.88 (1H, t, J=5.6 Hz), 4.67 (1H, t, J=5.0 Hz), 3.79 (6H, t, J=7.5 Hz), 3.69-3.61 (2H, m), 3.50-3.44 (2H, m), 3.30 (3H, tt, J=20.6, 6.5 Hz), 3.15-3.06 (3H, m), 2.63 (1H, s), 2.21-2.17 (4H, m), 1.78 (1H, s), 1.62 (4H, t, J=6.9 Hz), 1.43 (2H, t, J=5.4 Hz), 1.30 (20H, dt, J=29.2, 11.0 Hz), 0.87 (6H, t, J=6.9 Hz).

Step 4

To Compound 11-6 (541 mg, 0.66 mmol) in dichloromethane solution (2 mL), DIEA (0.35 mL, 1.98 mmol), DMAP (8.0 mg, 0.066 mmol) and succinic anhydride (132 mg, 1.32 mmol) were added, and the mixture was stirred at room temperature for four hours. The reaction mixture was concentrated under reduced pressure, and the resulting crude product was purified by silica gel column chromatography (chloroform:methanol=40:1→10:1) to obtain Compound 12-6 (591 mg, 97%) as colorless liquid.

$^1$H-NMR (CDCl$_3$) δ: 7.41 (2H, d, J=7.5 Hz), 7.31-7.25 (8H, m), 7.20 (1H, t, J=7.2 Hz), 6.82 (4H, d, J=8.5 Hz), 6.62 (1H, t, J=6.3 Hz), 6.48 (1H, t, J=6.5 Hz), 5.91 (1H, t, J=5.5 Hz), 4.71 (1H, t, J=5.3 Hz), 4.42 (1H, dd, J=11.0, 3.2 Hz), 4.14 (1H, dd, J=10.9, 5.9 Hz), 3.79 (6H, s), 3.40 (4H, tt, J=20.4, 7.0 Hz), 3.08 (4H, dq, J=33.3, 8.0 Hz), 2.69-2.49 (4H, m), 2.20 (4H, dd, J=15.6, 8.2 Hz), 1.95 (1H, s), 1.61 (4H, d, J=7.0 Hz), 1.27 (22H, d, J=5.0 Hz), 0.87 (6H, dd, J=6.8, 5.1 Hz).

Step 5

To Compound 12-6 (312 mg, 0.34 mmol) in a mixture of acetonitrile/dichloromethane (4:1, 25 mL), DIEA (0.30 mL, 1.70 mmol) and HBTU (142 mg, 0.37 mmol) were added, and the mixture was shaken at room temperature for 15 minutes. To the reaction mixture, HybridCPG amino form 2000 Å (Prime Synthesis, Inc.) (2.8 g) was added, and the mixture was shaken for 24 hours. After the reaction mixture was filtered, HybridCPG resin was washed three times with acetonitrile and three times with diethyl ether and dried under reduced pressure. To the dried HybridCPG, a mixture of THF/acetic anhydride/pyridine (8:1:1, 30 mL) was added, and the mixture was shaken for three hours. After the reaction mixture was filtered, HybridCPG resin was washed twice with pyridine, twice with isopropanol and twice with diethyl ether, and dried under reduced pressure. The supported amount of Compound 12-6 was calculated by colorimetric assay of the DMTr cation, and Compound 13-6 whose supported amount is 114 μmol/g was obtained.

3-2) the Following Compounds were Synthesized in a Similar Method to 3-1). Compound 13-8 whose supported amount of Compound 12-8 is 107 μmol/g Compound 13-10 whose supported amount of Compound 12-10 is 69 μmol/g Compound 13-12 whose supported amount of Compound 12-12 is 31 μmol/g Compound 13-14 whose supported amount of Compound 12-14 is 40 μmol/g Compound 13-18 whose supported amount of Compound 12-18 is 15 μmol/g Compound 13-20 whose supported amount of Compound 12-20 is 48 μmol/g Compound 13-22 whose supported amount of Compound 12-22 is 47 μmol/g 4) Synthesis of Compound 14-n'

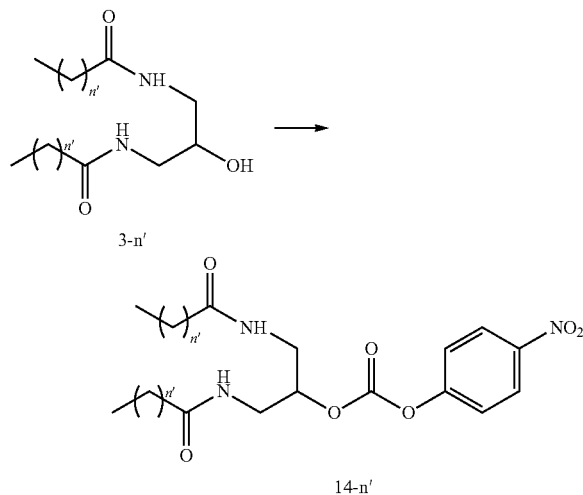

wherein n' is an integer of 5 to 29.

4-1) Synthesis of Compound 14-16

To Compound 3-16 (3.0 g, 4.81 mmol) in THF solution (80 mL), pyridine (0.78 mL, 9.63 mmol), 4-nitrophenyl chloroformate (1.94 g, 9.63 mmol) and DMAP (59 mg, 0.481 mmol) were added, the mixture was stirred at 70° C. for three hours. The reaction mixture was filtered. After the mother liquid was distilled off under reduced pressure, and the resulting crude product was purified by silica gel column chromatography (hexane:ethyl acetate=50:50) to obtain Compound 14-16 (1 g, 26%) as a white solid.

$^1$H-NMR (CDCl$_3$) δ: 8.29 (2H, dt, J=9.7, 2.6 Hz), 7.43 (2H, dt, J=9.9, 2.7 Hz), 6.28 (2H, t, J=6.4 Hz), 4.80-4.77 (1H, m), 3.62 (2H, ddd, J=14.5, 7.0,), 3.51 (2H, dt, J=14.5, 6.3 Hz), 2.25 (4H, t, J=7.7 Hz), 1.65 (4H, td, J=12.4, 5.3 Hz), 1.36-1.20 (56H, m), 0.88 (6H, t, J=6.8 Hz).

5) Synthesis of Compound 18

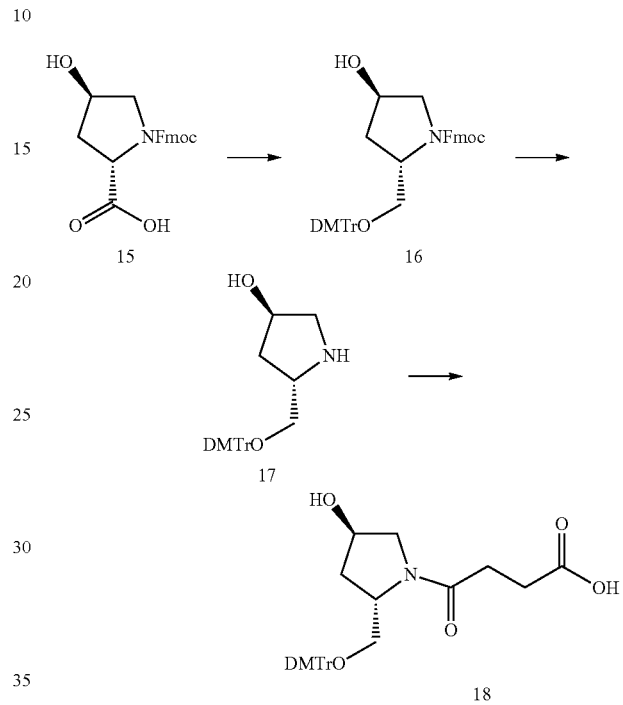

Compound 17 was synthesized from Compound 15 according to the methods described in Nucleic Acids Research, 42, 8796-8807 (2014).

To Compound 17 (3.00 g, 7.15 mmol) in dichloromethane solution (15 ml), triethylamine (1.98 ml, 14.3 mmol, 2.0 eq.), succinic anhydride (751 mg, 7.51 mmol, 1.05 eq.) were added at room temperature, and the mixture was stirred at room temperature for one hour. The reaction mixture was concentrated under reduced pressure. The resulting residue was purified by silica gel column chromatography (SiO$_2$:120 g, chloroform:methanol:triethylamine=95:5:1→75:25:1) to obtain Compound 18 (3.37 g, Yield 91%) as colorless powder. By 1H-NMR, it was observed a mixture of rotamers, which is 63:37.

ESI-MS (m/z): 530 (M+H). HPLC Peak RT=1.86 min.

$^1$H-NMR (CDCl$_3$) δ: (Major) 7.39-7.33 (2H, m), 7.30-7.22 (6H, m), 7.22-7.16 (1H, m), 6.85-6.77 (4H, m), 4.50 (1H, brs), 4.41 (1H, m), 3.88 (1H, d, J=11.0 Hz), 3.775 (6H, s), 3.65 (1H, dd, J=11.0, 4.0 Hz), 3.43 (1H, dd, J=9.2, 4.5 Hz), 3.14 (1H, dd, J=9.2, 2.7 Hz), 2.85-1.97 (6H, m). (Minor) 7.39-7.33 (2H, m), 7.30-7.22 (6H, m), 7.22-7.16 (1H, m), 6.85-6.77 (4H, m), 4.41 (1H, m), 4.31 (1H, brs), 4.11 (1H, d, J=12.3 Hz), 3.783 (6H, s), 3.25 (1H, dd, J=12.3, 3.5 Hz), 3.18 (1H, dd, J=9.5, 4.8 Hz), 3.10 (1H, dd, J=9.5, 4.8 Hz), 2.85-1.97 (6H, m).

6) Synthesis of Compound 27-n'

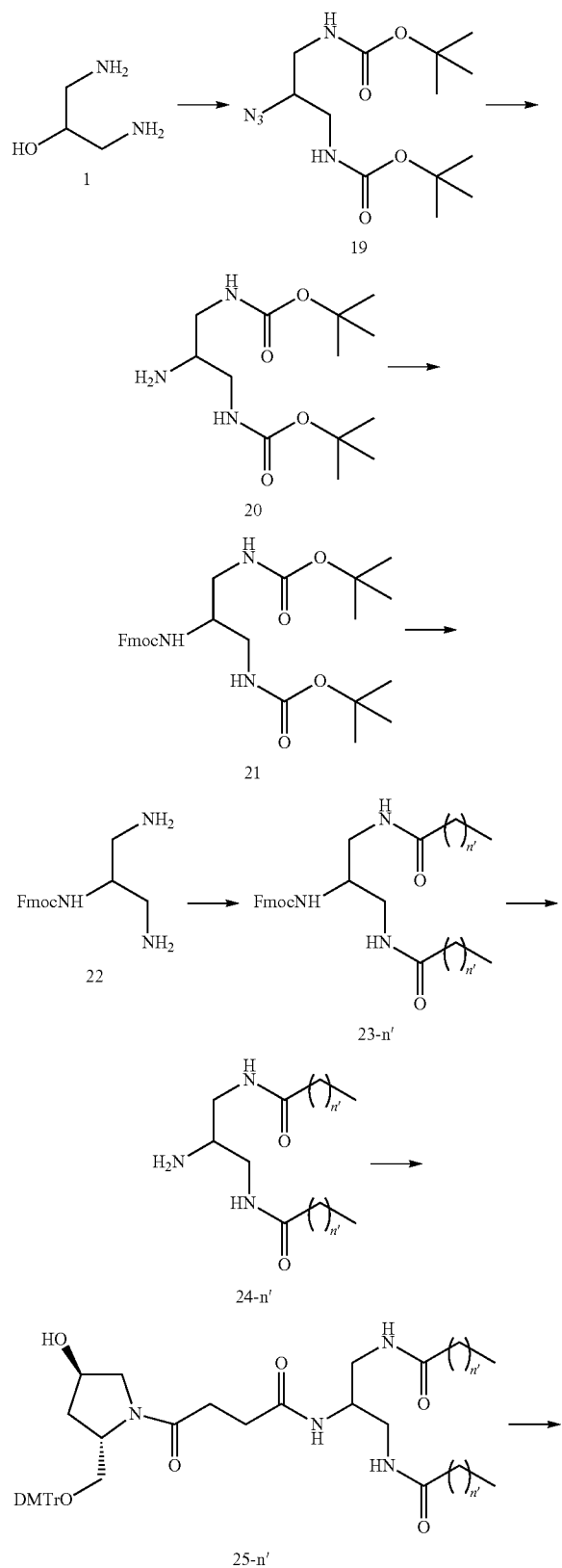

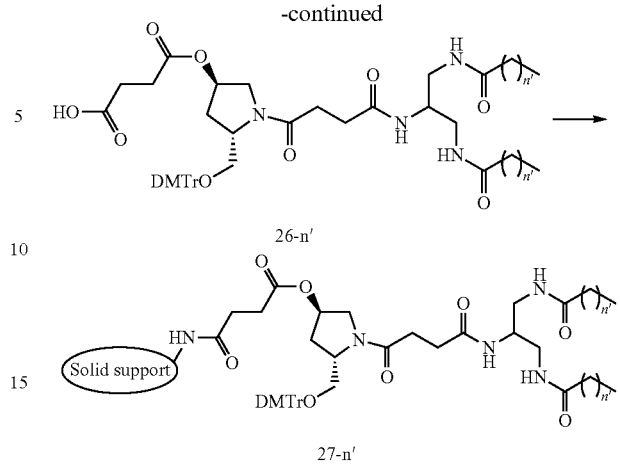

wherein n' is an integer of 5 to 29.

6-1) Synthesis of Compound 27-12

Step 1

Compound 19 was synthesized from Compound 1 according to the methods described in Journal of Medicinal Chemistry, 48, 7781 (2005).

Step 2

To Compound 19 (3.00 g, 7.15 mmol) in a mixture of THF-water (9:1) (30 ml), triphenylphosphine (1.98 ml, 14.3 mmol, 2.0 eq.) was added at room temperature, and the mixture was stirred at room temperature for one hour. The temperature was raised up to 70° C., and the mixture was stirred for four hours. After cooling to room temperature, the reaction mixture was concentrated under reduced pressure to the crude product of obtain Compound 20 as colorless oil.

Step 3

To Compound 20 (7.15 mmol) in dichloromethane (30 ml), triethylamine (2.10 ml, 15.1 mmol, 1.2 eq.) and Fmoc-Cl (3.59 g, 13.9 mmol, 1.1 eq.) were added at room temperature, and the mixture was stirred at room temperature for one hour. The reaction mixture was diluted with chloroform, washed with brine, and then dried over magnesium sulfate. The solvent was distilled off under reduced pressure. The resulting solid was washed with n-hexane and a little of chloroform, and then purified by silica gel column chromatography ($SiO_2$:120 g, n-hexane:ethyl acetate=75: 25-0:100) to obtain Compound 21 (4.18 g, Yield from Compound 19: 65%) as colorless foam.

ESI-MS (m/z): 512 (M+H). HPLC Peak RT=2.71 min.

$^1$H-NMR ($CDCl_3$):7.80 (2H, d, J=7.5 Hz), 7.60 (2H, d, J=7.5 Hz), 7.40 (2H, dd, J=7.5, 7.5 Hz), 7.30 (2H, dd, J=7.5, 7.5 Hz), 6.02 (1H, brs), 5.21 (2H, brs), 4.46-4.27 (2H, m), 4.21 (1H, m), 3.59 (1H, m), 3.45-3.29 (2H, m), 3.27-3.13 (2H, m), 1.46 (18H, s).

Step 4

To Compound 21 (1.5 g, 2.93 mmol), TFA (10 ml) was added, and the mixture was stirred at room temperature for one hour. The mixture was concentrated under reduced pressure to obtain the crude product of Compound 22.

ESI-MS (m/z): 312 (M+H). HPLC Peak RT=1.06 min.

Step 5

To Compound 22 in dichloromethane (15 ml), triethylamine (2.43 ml, 17.59 mmol) and myristoyl chloride (1.59 g, 6.45 mmol) was added at room temperature, and the mixture was stirred at room temperature overnight. The resulting white precipitate was collected by filtration, washed with dichloromethane, water and n-hexane, and then dried under reduced pressure to obtain Compound 23-12 (2.45 g) as a solid.

$^1$H-NMR (CDCl$_3$)δ:12.32 (1H, s), 7.76 (2H, d, J=7.3 Hz), 7.60 (2H, d, J=7.3 Hz), 7.35 (4H, dt, J=33.7, 7.3 Hz), 6.56 (1H, s), 6.40 (1H, s), 4.32-4.19 (2H, m), 3.60 (2H, s), 3.20-3.09 (4H, m), 2.23 (4H, t, J=7.1 Hz), 1.64 (4H, s), 1.37-1.25 (40H, m), 0.88 (6H, t, J=6.8 Hz).

Step 6

To Compound 23-12 (1.9 g, 2.60 mmol) in DMF (15 ml), piperidine (0.290 ml, 2.93 mmol) was added, and the mixture was stirred at 80° C. for 20 minutes. After cooling to room temperature, the resulting precipitate was collected by filtration, washed with n-hexane, and dried under reduced pressure to obtain Compound 24-12 (742 mg, Yield 50%) as a solid.

$^1$H-NMR (CDCl$_3$)δ:6.43 (1H, s), 3.43 (2H, t, J=8.2 Hz), 3.03 (4H, m), 2.22 (4H, t, J=7.6 Hz), 1.73 (4H, m), 1.38-1.25 (40H, m), 0.88 (6H, t, J=6.7 Hz).

Step 7

To Compound 18 (585 mg, 1.13 mmol) in DMF (5 mL), DIEA (1.20 ml, 1.79 mmol) and HBTU (677 mg, 1.79 mmol) were added at room temperature, and the mixture was stirred at room temperature for 10 minutes. The mixture was added to Compound 24-12 (700 mg, 1.37 mmol) in dichloromethane (30 mL) at 45° C., and then the mixture was stirred for 30 minutes at 45° C. Since the insoluble material was confirmed, it was completely dissolved by adding DMF (1.5 mL). After the solvent of the reaction mixture was distilled off under reduced pressure, the reaction mixture was washed with aqueous saturated sodium bicarbonate solution, and then dried over magnesium sulfate. The solvent was distilled off under reduced pressure. The resulting residue was dissolved in ethyl acetate, and n-hexane was added thereto at 80° C. The target product was precipitated and collected by filtration to obtain Compound 25-12 (1.31 g, Yield 88%) as a solid. The resulting product was used for the next reaction without further purification.

Step 8

To Compound 25-12 (1.0 g, 0.919 mmol) in dichloromethane (20 ml), triethylamine (0.510 ml, 3.68 mmol, 4 eq.), succinic anhydride (184 mg, 1.839 mmol, 2 eq.) and dimethylamino pyridine (1 mg) were added in order at room temperature. After the mixture was stirred at room temperature for two hours, triethylamine (0.255 ml) and succinic anhydride (90 mg) was added thereto because the starting material was remained, and the mixture was stirred at room temperature overnight. The reaction mixture was concentrated under reduced pressure. The resulting residue was purified by silica gel column chromatography (SiO$_2$: 30 g, chloroform:methanol:triethylamine=100:0:1→90:10:1) to obtain Compound 26-12 (261 mg, Yield 35%) as a solid.

ESI-MS (m/z): 1110 (M−H). HPLC Peak RT=3.08 min.

Step 9

Compound 27-12 whose supported amount of Compound 26-12 is 31.2 μmol/g was synthesized in a similar method to Step 5 of 3-1).

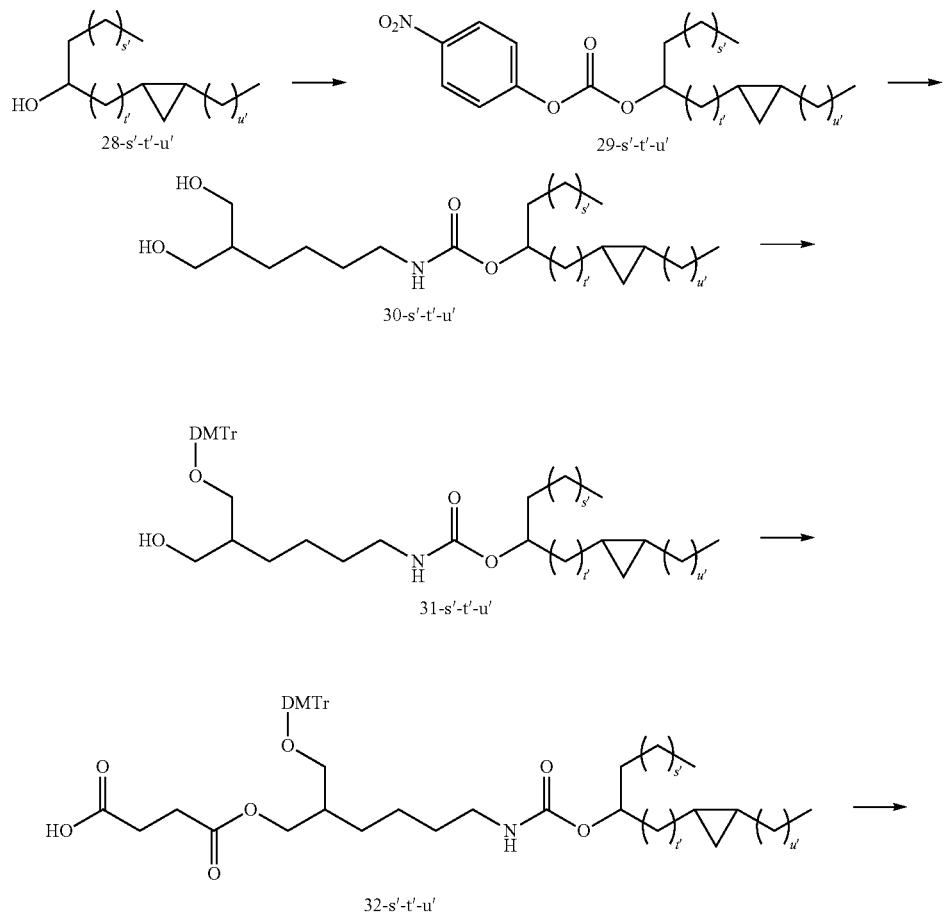

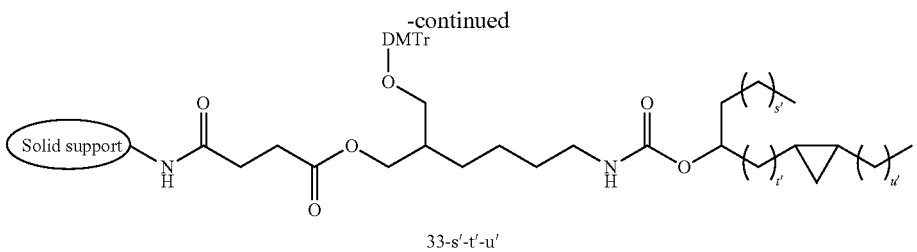

33-s'-t'-u' wherein s', t' and are each independently an integer of 3 to 20.

7-1) Synthesis of Compound 33-7-7-7

Step 1

Compound 28-7-7-7 was synthesized according to the methods described in Journal of Controlled Release, 220, 44-50 (2015).

Step 2

To Compound 28-7-7-7 (1 g, 2.45 mmol) in THF (50 mL), bis(4-nitrophenyl) carbonate (2.23 g, 7.34 mmol) and DMAP (897 mg, 7.34 mmol) were added, and the mixture was stirred at 65° C. for two hours. The reaction mixture was distilled off under reduced pressure, and the resulting crude product was purified by silica gel column chromatography (hexane:ethyl acetate=100:10) to obtain Compound 29-7-7-7 (932 mg, 66%) as colorless solid.

ESI-MS (m/z): 591 (M+H+H2O). HPLC Peak RT=2.49 min.

Step 3

To Compound 29-7-7-7 (644 mg, 1.12 mmol) in dichloromethane (6.4 mL), 6-amino-2-hydroxymethyl hexane-1-ol (500 mg, 0.89 mmol) in DMF (6.4 mL) and DIEA (0.39 mL, 2.24 mmol) were added, and the mixture was stirred at 40° C. for two hours. After water added to the reaction mixture to stop the reaction, the reaction mixture was transferred to a separatory funnel. The organic layer was washed twice with water and once with brine. After the resulting organic layer was dried over magnesium sulfate, the solvent was distilled off under reduced pressure. The resulting crude product was purified by silica gel column chromatography (hexane:ethyl acetate=50:50) to obtain Compound 30-7-7-7 (424 mg, 65%) as colorless oil.

ESI-MS (m/z): 583 (M+H). HPLC Peak RT=2.06 min.

Step 4

To Compound 30-7-7-7 (424 mg, 0.729 mmol) in pyridine (6.4 mL), DMTrCl (272 mg, 0.802 mmol) was added, and the mixture was stirred at room temperature for 16 hours. The reaction mixture was concentrated under reduced pressure, and then purified by diol silica gel column chromatography (hexane:ethyl acetate=3:1) to obtain Compound 31-7-7-7 (510 mg, 51%) as colorless oil.

ESI-MS (m/z): 883 (M−H). HPLC Peak RT=2.60 min

Step 5

To Compound 31-7-7-7 (510 mg, 0.58 mmol) in dichloromethane (6.4 mL), DMAP (137 mg, 1.12 mmol), succinic anhydride (337 mg, 3.37 mmol) and DIEA (0.59 mL, 3.37 mmol) were added, and the mixture was stirred at room temperature for 3 days. After the reaction mixture was concentrated under reduced pressure, the resulting crude product was purified by silica gel column chromatography (chloroform:methanol=20:1) to obtain Compound 32-7-7-7 (945 mg) as colorless liquid.

ESI-MS (m/z): 983 (M−H). HPLC Peak RT=1.97 min

Step 6

Compound 33-7-7-7 whose supported amount of Compound 32-7-7-7 is 16 µmol/g was synthesized in a similar method to Step 5 of 3-1).

8) Synthesis of Compound 42

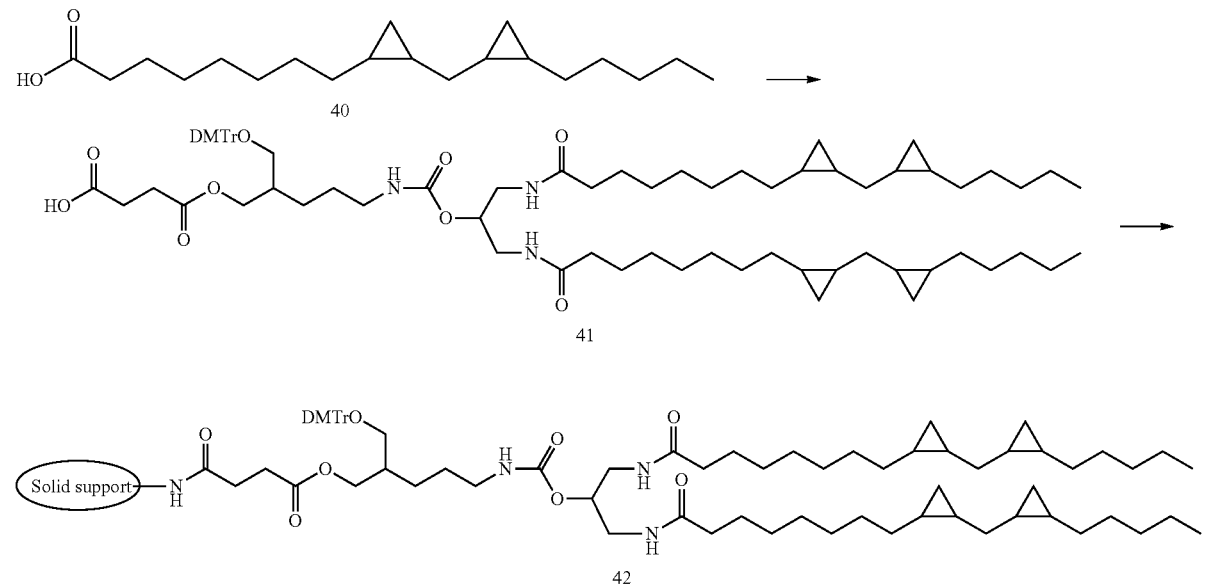

Step 1

Compound 41 was synthesized from Compound 40 described in Bioorganic & Medicinal Chemistry Letters, 13(6), 1037-1040; 2003 in a similar method to Step 1 of 1-1) and Steps 1 to 4 of 3-1).

$^1$H-NMR (CDCl$_3$) δ: 7.42-7.18 (m, 5H), 6.81 (m, 2H), 6.55 (brs, 1H), 6.39 (brs, 1H), 5.91 (brs, 1H), 4.72 (m, 1H), 4.43 (m, 1H), 4.15 (m, 1H), 3.79 (s, 6H), 3.45-3.37 (m, 4H), 3.05 (m, 4H), 2.58-2.52 (m, 4H), 2.19 (m, 4H), 1.95 (brs, 1H), 1.60-1.14 (m, 32H), 0.88 (m, 4H), 0.78-0.61 (m, 8H), 0.28 (m, 4H).

Step 2

Compound 42 whose supported amount of Compound 41 is 92 μmol/g was synthesized in a similar method to Step 5 of 3-1).

9) Synthesis of Compound 48-n'

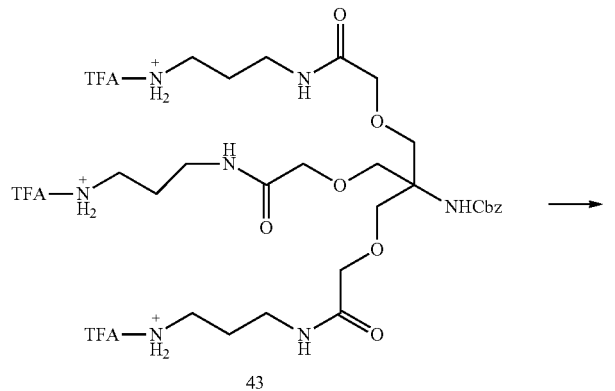

43

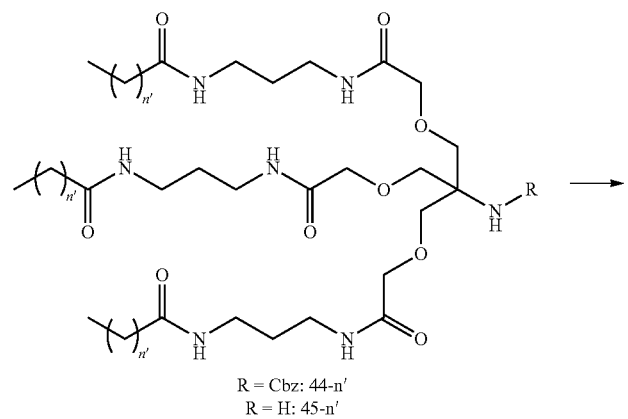

R = Cbz: 44-n'
R = H: 45-n'

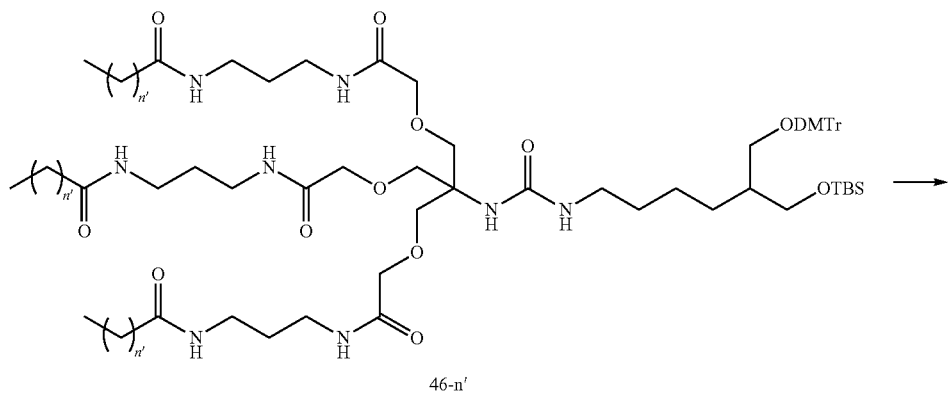

46-n'

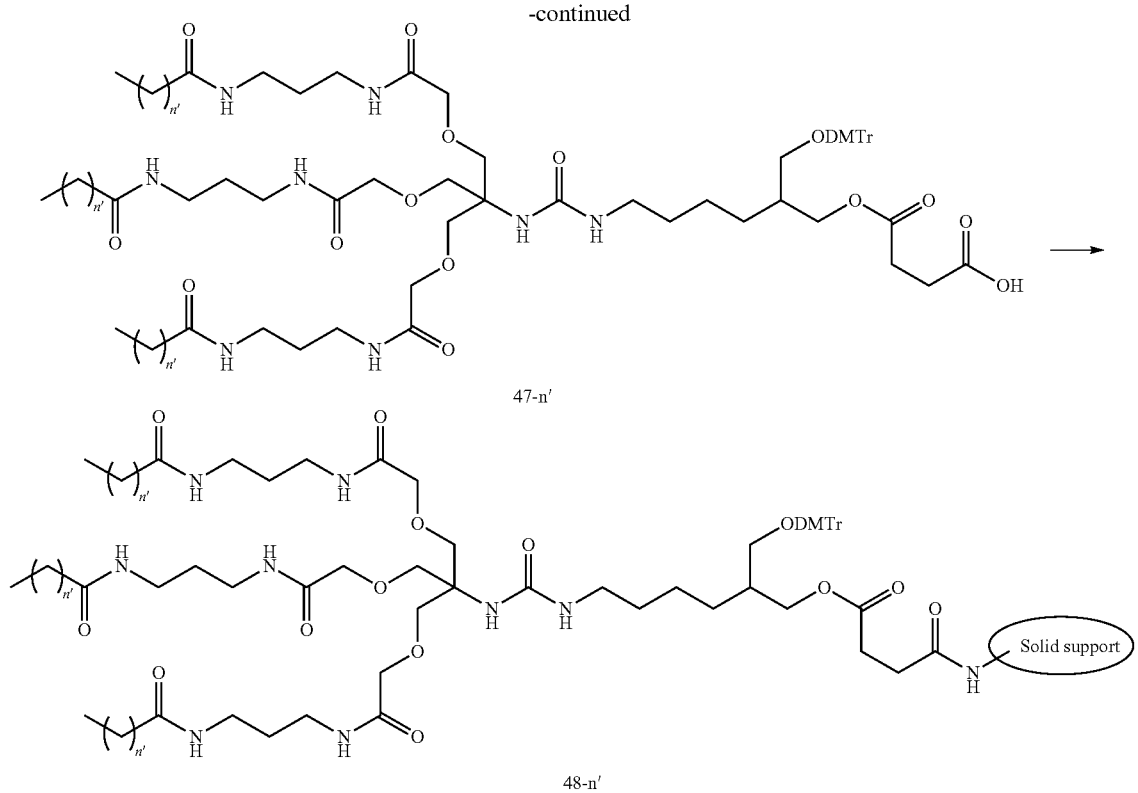

wherein n' is an integer of 5 to 29.

9-1) Synthesis of Compound 48-8

Step 1

Decanoic acid (1.16 g, 6.75 mmol, Tokyo Chemical Industry Co., Ltd.) was dissolved in DMF (14 mL) and dichloromethane (14 mL). DIEA (3.14 mL, 18 mmol) and HBTU (2.82 g, 7.43 mmol) were added thereto, and the mixture was vigorously stirred at room temperature for one hour. To the resulting brown solution, Compound 43 (see Chemistry-A European Journal (2010), 16, (15), 4519-4532, S4519, 2.0 g, 2.25 mmol) was added at room temperature, and the mixture was stirred at room temperature for 24 hours. The reaction mixture was concentrated under reduced pressure. The residue was treated with acetonitrile containing 25% water, and the resulting solid was collected by filtration. The resulting solid was washed three times with water and three times with acetonitrile containing 25% water to obtain Compound 44-8 (2.19 g, 2.07 mmol) as a white solid.

Step 2

Compound 44-8 (0.5 g, 0.471 mmol) was dissolved in ethanol (6 mL), and palladium hydroxide (221 mg, Pd 20%, hydrous) was added thereto. The mixture was vigorously stirred under hydrogen atmosphere at room temperature for two hours. After substituting with nitrogen, the insoluble material was filtered through a Celite. The filtrate was concentrated under reduced pressure, and acetonitrile was added to the residue. The resulting white solid was collected by filtration to obtain Compound 45-8 (0.400 g, 0.471 mmol) as a white foamy solid.

$^1$H-NMR (CDCl$_3$)δ:6.44 (brs, 2H), 3.71 (m, 6H), 3.37 (m, 6H), 3.27 (m, 12H), 2.45 (m, 6H), 2.17 (m, 6H), 1.63 (m, 6H), 1.25 (m, 36H), 0.88 (t, 9H, J=6.8 Hz).

Step 3

Under nitrogen atmosphere, to Compound 45-8 (0.4 g, 0.432 mmol) in DMF (1.7 mL)-dichloromethane (1.4 mL)-chloroform (1.0 mL), bis-(p-nitrophenyl) carbonate (0.131 g, 0.432 mmol) and DIEA (0.226 mL, 1.30 mmol) were added, and the mixture was stirred at room temperature for 12 hours. Next, Compound 8 (0.243 g, 0.432 mmol) obtained in 2) was added thereto, and the mixture was stirred at room temperature for six hours. The reaction mixture was diluted with ethyl acetate. The organic layer was washed three times with water, twice with 0.2 M aqueous potassium hydrogen carbonate solution, and with brine, and dried over anhydrous magnesium sulfate. After filtering off the solid, the filtrate was concentrated under reduced pressure. The residue was purified by silica gel column chromatography (chloroform:acetone=1:0→9:1) to obtain Compound 46-8 (0.375 g, 0.247 mmol) as a white solid.

$^1$H-NMR (CDCl$_3$)δ:7.40 (m, 2H), 7.30-7.26 (m, 13H), 7.09 (m, 3H), 5.82 (brs, 1H), 5.51 (brm, 1H), 3.78 (s, 6H), 3.68-3.65 (m, 13H), 3.25 (m, 12H), 3.03 (m, 2H), 2.44 (m, 6H), 2.17 (m, 6H), 1.63-1.60 (m, 6H), 1.27-1.25 (m, 28H), 0.89-0.72 (m, 18H).

Step 4

Compound 47-8 was synthesized from Compound 46-8 in a similar method to Steps 3 and 4 of 3-1).

$^1$H-NMR (CDCl$_3$)δ:7.41-7.20 (m, 5H), 6.82 (m, 4H), 6.61 (brs, 3H), 3.79 (s, 6H), 3.69-3.62 (m, 12H), 3.25 (m, 12H), 3.02 (m, 6H), 2.60 (m, 6H), 2.42 (m, 6H), 2.17 (m, 6H), 1.60 (m, 12H), 1.27 (m, 20H), 0.88 (m, 9H).

Step 5

Compound 48-8 whose supported amount of Compound 47-8 is 68.6 μmol/g was synthesized in a similar method to Step 5 of 3-1).

9-2) Synthesis of Compound 48-12
The following compounds were synthesized in a similar method to 9-1). Compound 47-12
$^{1}$H-NMR (CDCl$_3$) δ: 7.40-7.26 (m, 5H), 6.81 (m, 4H), 6.56 (brs, 3H), 3.79 (s, 6H), 3.69-3.62 (m, 12H), 3.25 (m, 12H), 3.07 (m, 8H), 2.58 (m, 4H), 2.44 (m, 6H), 2.17 (m, 6H), 1.60 (m, 12H), 1.27-1.22 (m, 60H), 0.88 (m, 9H).
Compound 48-12 whose supported amount of Compound 47-12 is 70.0 μmol/g
10) Synthesis of Compound 55-m'-n'
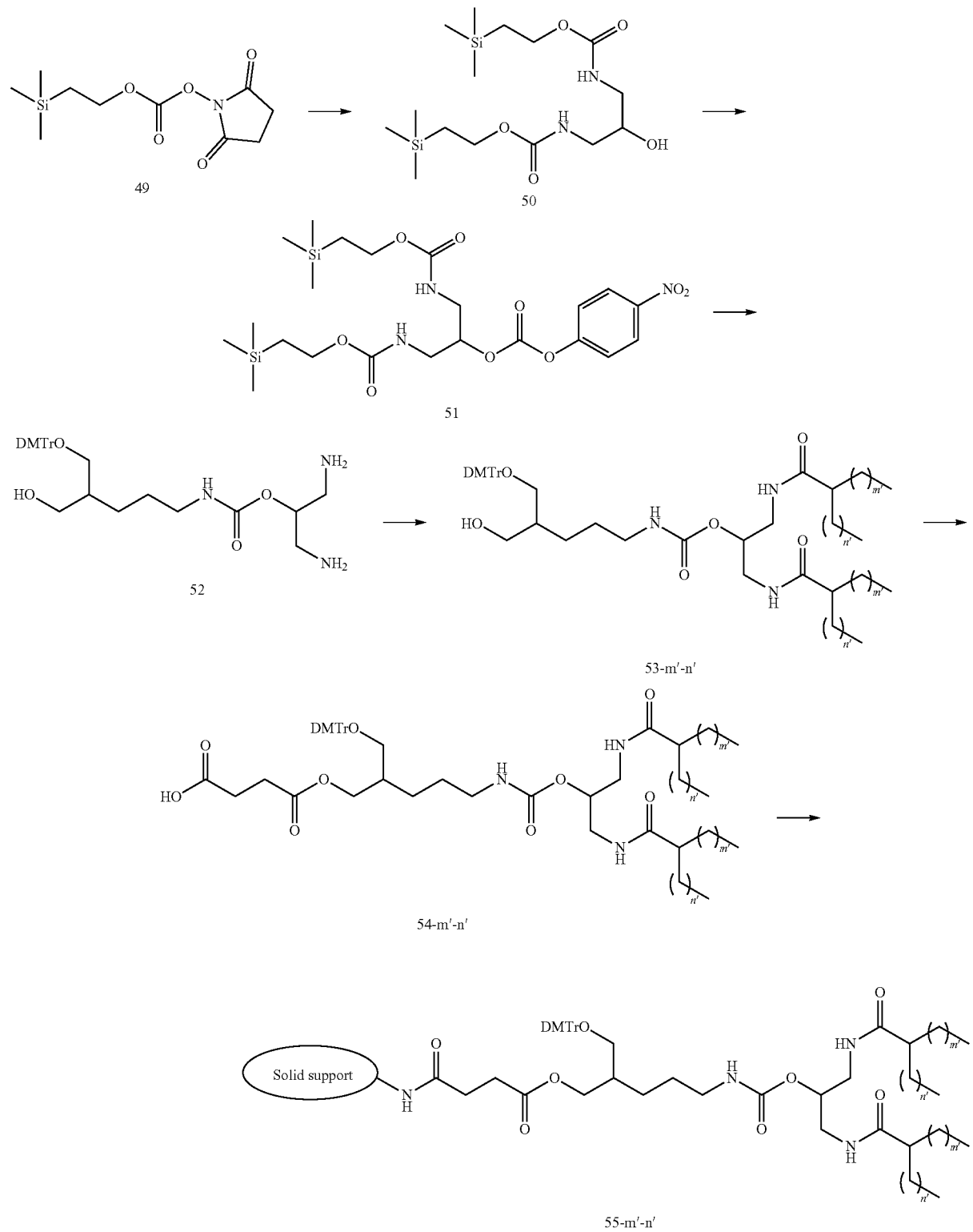

wherein m' and n' are each independently an integer of 5 to 29.

10-1) Synthesis of Compound 55-5-7

Step 1

Compound 49 (20 g, 77 mmol, Tokyo Chemical Industry Co., Ltd.) was dissolved in dichloromethane (5 mL), and DIEA (13.5 mL, 77 mmol) was added thereto at 0° C. The temperature was raised to room temperature. Then, the mixture was stirred at room temperature overnight. The reaction mixture was concentrated under reduced pressure, and the residue was purified by silica gel column chromatography (hexane:ethyl acetate=7:3-4:6) to obtain Compound 50 (22.5 g, 59.4 mmol) as colorless oil.

$^1$H-NMR (CDCl$_3$):5.18 (brs, 2H), 4.11 (m, 4H), 3.74 (m, 1H), 3.45 (s, 1H), 3.39 (m, 1H), 3.29-3.20 (m, 4H), 0.93 (t, 4H, J=8.4 Hz), 0.00 (s, 18H).

LC/MS: [M+] m/z: 380

Step 2

Under nitrogen atmosphere, to Compound 50 (3.79 g, 10 mmol) in THF (33 mL), bis-(p-nitrophenyl) carbonate (3.04 g, 10 mmol) and DIEA (1.75 mL, 10 mmol) and DMAP (1.2 g, 10 mmol) were added, and the mixture was stirred at room temperature for 12 hours. The reaction mixture was concentrated under reduced pressure, and the residue was purified by silica gel column chromatography (hexane:ethyl acetate=4:1→1:1) to obtain Compound 51 (4.43 g, 8.14 mmol) as colorless oil.

$^1$H-NMR (CDCl$_3$):8.26 (d, 2H, J=9.2 Hz), 7.38 (d, 2H, J=9.2 Hz), 5.20 (brs, 2H), 4.77 (brs, 1H), 4.13 (t, 2H, J=8.8 Hz), 3.51-3.46 (m, 4H), 0.93 (m, 4H), 0.00 (m, 18H).

LC/MS: [M+] m/z: 545

Step 3

Compound 52 was synthesized from Compound 51 in a similar method to Steps 2 and 3 of 3-2).

$^1$H-NMR (CDCl$_3$):7.41-7.20 (m, 5H), 6.82 (m, 4H), 3.79 (s, 6H), 3.72-3.62 (m, 4H), 3.22-3.01 (m, 6H), 1.29 (m, 6H).

Step 4

To 2-hexyldecanoic acid (110 mg, 0.428 mmol) in dichloromethane (2 mL)-DMF (2.5 mL), DIEA (0.102 mL, 0.583 mmol) and HBTU (0.162 g, 0.428 mmol) were added, and the mixture was vigorously stirred at room temperature for 30 minutes. To the resulting brown solution, Compound 52 (0.110 g, 0.194 mmol) was added at room temperature, and the mixture was stirred at room temperature for 24 hours. The reaction mixture was concentrated under reduced pressure. The residue was diluted with ethyl acetate. The organic layer was washed three times with water, and then dried over anhydrous magnesium sulfate. After filtering off the solid, the filtrate was concentrated under reduced pressure. The residue was purified by amino silica gel column chromatography (n-hexane:ethyl acetate=1:0→1:1) to obtain Compound 53-5-7 (90 mg, 0.086 mmol) as white amorphous.

$^1$H-NMR (CDCl$_3$):7.42-7.19 (m, 5H), 6.83 (m, 4H), 4.81 (brm, 1H), 4.65 (brs, 1H), 3.79 (s, 6H), 3.67 (m, 2H), 3.46-3.39 (m, 3H), 3.25 (m, 1H), 3.11 (m, 3H), 2.05 (m, 2H), 1.78 (m, 1H), 1.55-1.24 (m, 48H), 0.84 (m, 12H).

Step 5

Compound 54-5-7 was synthesized from Compound 53-5-7 in a similar method to Step 4 of 3-1).

$^1$H-NMR (CDCl$_3$)δ:7.42-7.19 (m, 5H), 6.83 (m, 4H), 6.65 (brs, 1H), 6.52 (brs, 1H), 5.86 (brs, 1H), 4.65 (m, 1H), 4.38 (brs, 1H), 4.13 (m, 1H), 3.79 (s, 6H), 3.41 (m, 4H), 3.02 (m, 4H), 2.55 (m, 4H), 2.05 (m, 2H), 1.78 (m, 1H), 1.55-1.24 (m, 48H), 0.84 (m, 12H).

LC/MS: [M−] m/z: 1142

Step 6

Compound 55-5-7 whose supported amount of Compound 54-5-7 is 70.0 μmol/g was synthesized in a similar method to Step 5 of 3-1).

11) Synthesis of Compound 59

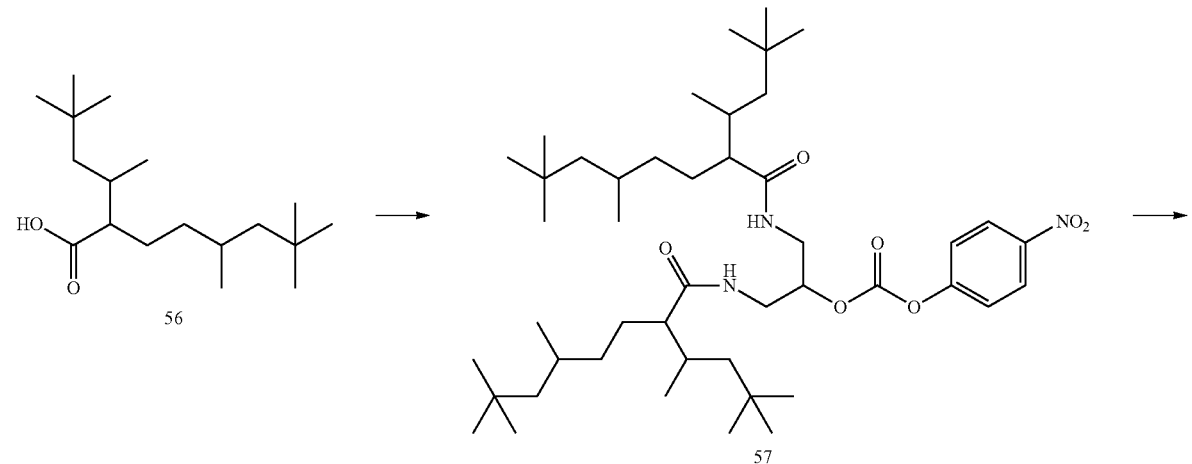

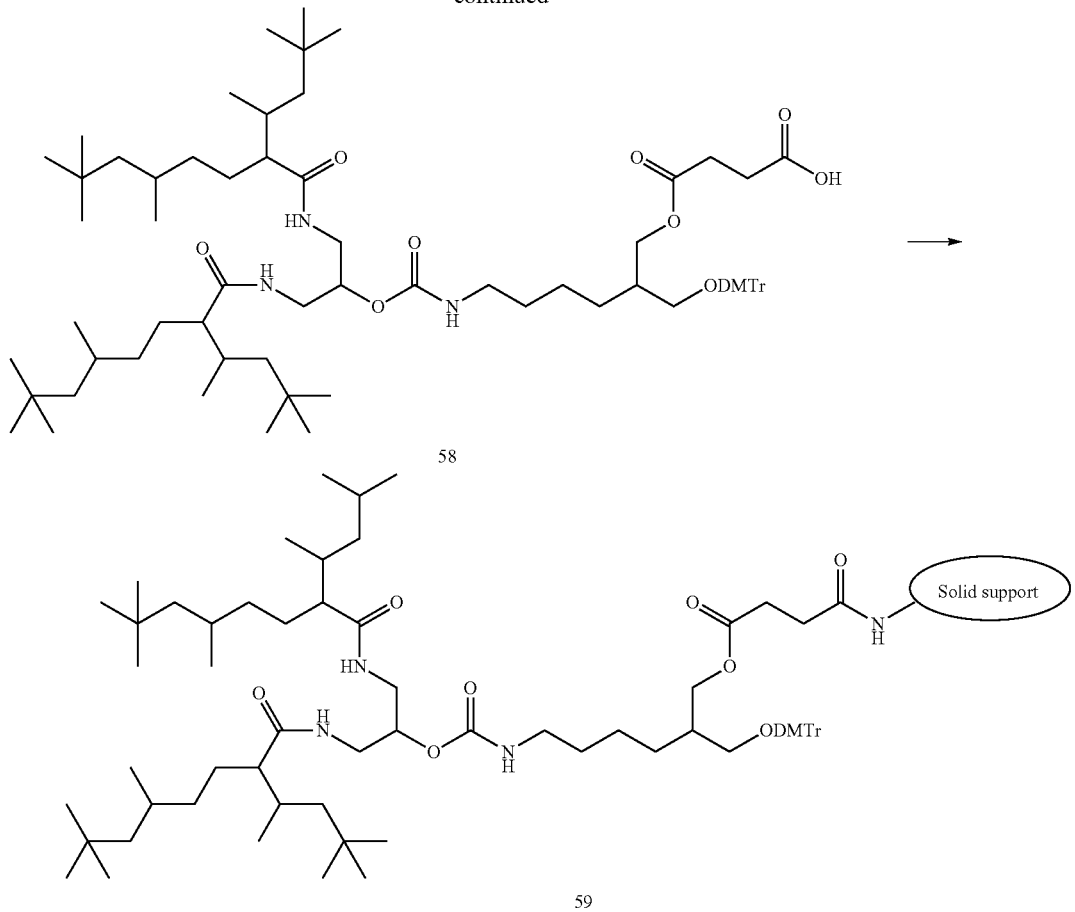

Step 1

Compound 57 was synthesized from Compound 56 (6.94 g, 24.4 mmol, Tokyo Chemical Industry Co., Ltd.) in a similar method to Step 1 of 3-1).

$^1$H-NMR (CDCl$_3$)δ:8.30 (d, 2H, J=9.2 Hz), 7.45 (m, 2H), 6.32 (brs, 2H), 4.75 (brs, 1H), 4.55 (brs, 1H), 3.51 (m, 6H), 1.87 (m, 1H), 1.70 (m, 1H), 1.67 (m, 16H), 1.25 (m, 6H), 1.21 (m, 6H), 1.03 (m, 12H), 0.88 (m, 42H).

LC/MS: [M+] m/z: 789

Step 2

Compound 58 was synthesized from Compound 57 in a similar method to Steps 2 to 4 of 3-1).

$^1$H-NMR (CDCl$_3$)δ:7.42-7.18 (m, 6H), 6.80 (d, 4H, J=8.4 Hz), 5.89 (brs, 1H), 4.62 (brs, 1H), 4.38 (brs, 1H), 4.14 (brs, 1H), 3.79 (s, 6H), 3.57-3.34 (m, 4H), 3.05 (m, 6H), 2.66-2.57 (m, 4H), 1.87 (m, 1H), 1.75 (m, 1H), 1.66 (m, 1H), 1.56 (m, 16H), 1.45 (m, 6H), 1.25 (m, 6H), 1.03 (m, 12H), 0.88 (m, 42H). LC/MS: [M−] m/z: 1198

Step 3

Compound 59 whose supported amount of Compound 58 is 53.4 µmol/g was synthesized in a similar method to Step 5 of 3-1).

12) Synthesis of Compound 62

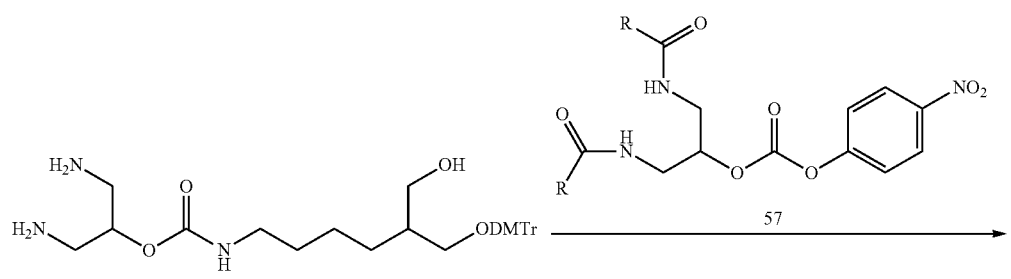

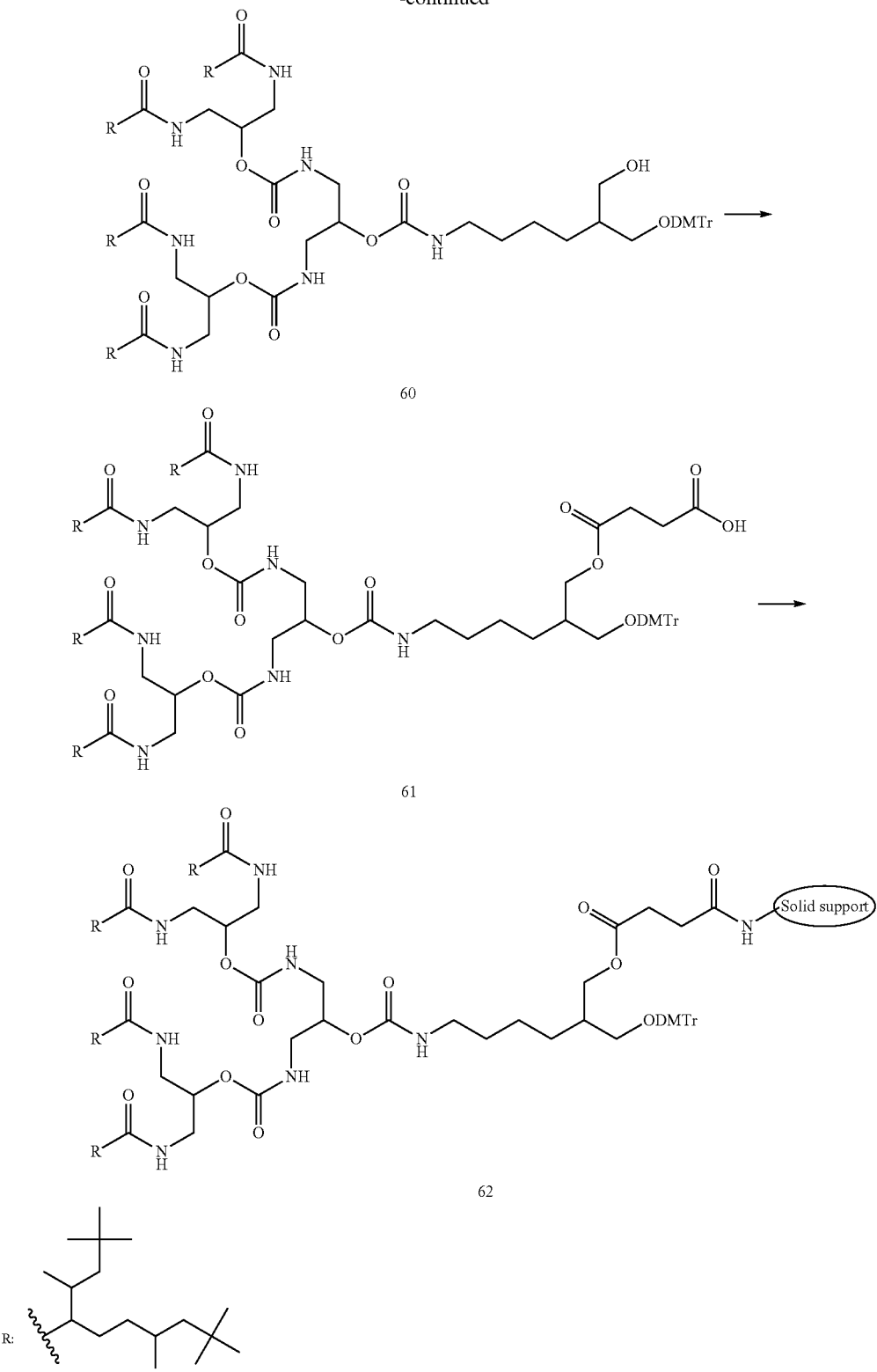

Step 1

Under nitrogen atmosphere, to Compound 52 (307 mg, 0.389 mmol) in THF (3 mL), DIEA (0.102 mL, 0.583 mmol), DMAP (23.8 mg, 0.194 mmol) and Compound 57 (110 mg, 0.194 mmol) obtained from Step 1 of 11) were added, and the mixture was stirred at 55° C. for five hours. Then, the reaction mixture was allowed to stand at room temperature overnight. The reaction mixture was diluted with ethyl acetate. The organic layer was washed three times with water, and dried over anhydrous magnesium sulfate.

After filtering off the solid, the filtrate was concentrated under reduced pressure. The residue was purified by silica gel column chromatography (hexane:ethyl acetate=1:0→1:1) to obtain Compound 60 (100 mg, 0.054 mmol) as white amorphous.

LC/MS: [M+3H]3+m/z: 622

Step 2

Compound 61 was synthesized from Compound 60 in a similar method to Step 4 of 3-1).

LC/MS: [M+2H]2+m/z: 983

Step 3

Compound 62 whose supported amount of Compound 61 is 47.7 μmol/g was synthesized in a similar method to Step 5 of 3-1).

13) Synthesis of Compound 65-n'

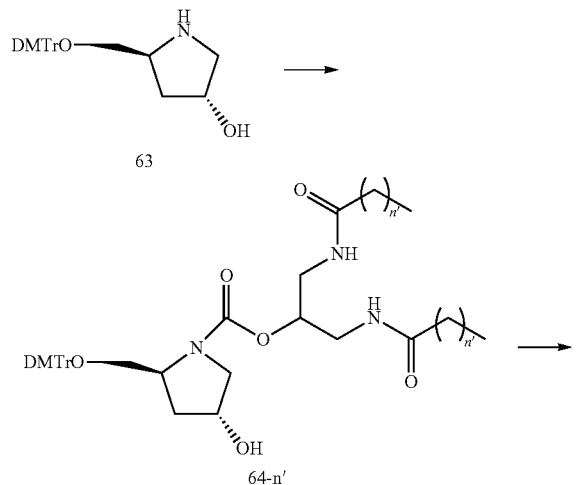

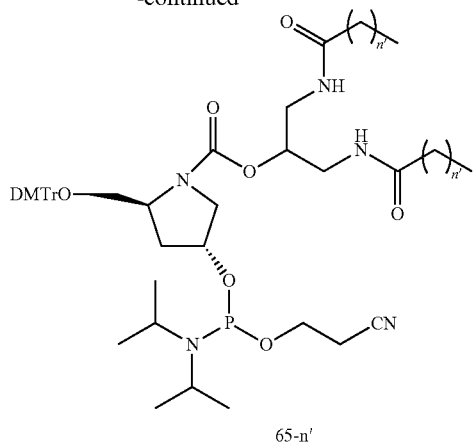

wherein n' is an integer of 5 to 29.

13-1) Synthesis of Compound 65-12

Step 1

Under nitrogen atmosphere, to Compound 63 (see Nucleic Acids Research, Volume 42, Issue 13, 29 Jul. 2014, Pages 8796-8807, 0.621 g, 1.48 mmol) in dichloromethane (29 mL), DMAP (181 mg, 1.48 mmol), DIEA (0.258 mL, 1.48 mmol) and Compound 9-12 (1.0 g, 1.48 mmol) obtained in a similar way of Step 1 of 3-1) were added, and the mixture was heated under reflux for four hours. The reaction mixture was concentrated under reduced pressure, and the residue was purified by silica gel column chromatography (chloroform:methanol=1:0→9:1) to obtain Compound 64-12 (1.0 g, 1.05 mmol) as colorless oil.

LC/MS: [M+H] m/z: 955

Step 2

Compound 65-12 was synthesized from Compound 64-12 in a similar method to Step 2 of 1-1).

$^{31}$P-NMR(CDCl$_{33}$)δ:147.9, 147.6, 147.4, 146.3

14) Synthesis of Compound 69-n'

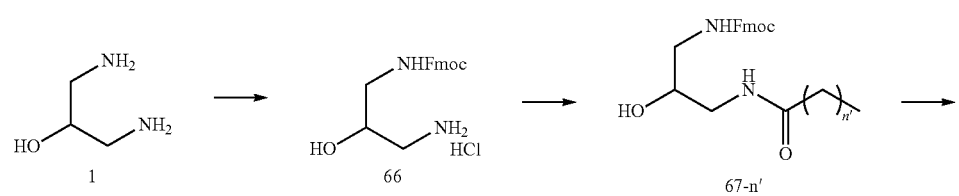

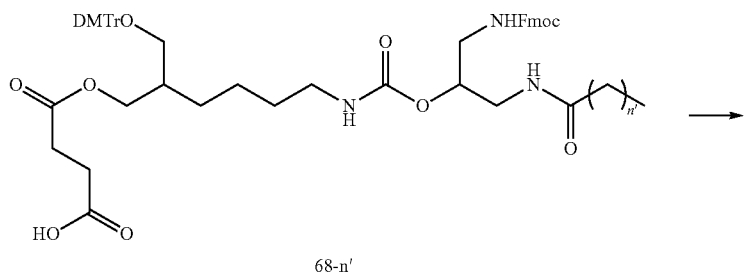

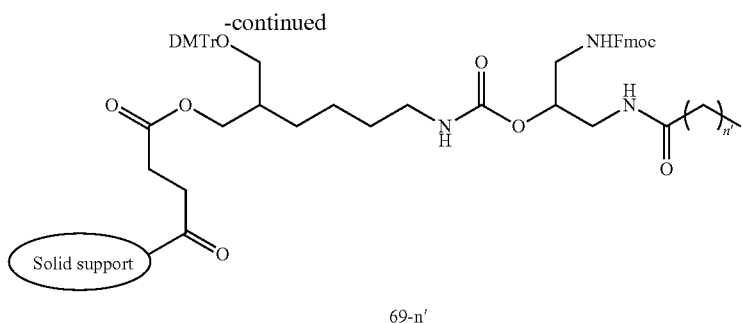

69-n' wherein n' is an integer of 5 to 29.

14-1) Synthesis of Compound 69-14

Step 1

To a suspension of 9-fluorenylmethyl-N-hydroxysuccinimide (4.00 g, 11.87 mmol, Watanabe Chemical Industries, Ltd.) in methanol (40.0 mL), Compound 1 (1.07 g, 11.87 mmol) in methanol (10.0 mL) was added at room temperature, and the mixture was stirred for 1.5 hours. Pyridine hydrochloride (3.02 g, 26.1 mmol) was added to the reaction mixture. The mixture was stirred for 10 minutes, and then filtered. The filtrate was concentrated, and the resulting crude product was purified by silica gel column chromatography (chloroform:methanol=90:10→75:25) to obtain Compound 66 (1.53 g, 37%) as white solid.

$^1$H-NMR (DMSO-D6) δ: 7.90 (2l, d, J=7.5 Hz), 7.82 (2l, s), 7.70 (2l, d, J=7.4 Hz), 7.44-7.41 (3H, m), 7.34 (2H, t, J=7.4 Hz), 5.53 (1H, d, J=5.0 Hz), 4.32 (2H, d, J=7.0 Hz), 4.22 (1H, t, J=6.7 Hz), 3.71 (1H, s), 3.12-3.06 (1H, m), 3.03-2.96 (1H, m), 2.87 (1H, dd, J=12.9, 2.6 Hz), 2.60 (1H, dd, J=12.9, 9.2 Hz).

ESI-MS (m/z): 313 (M+1).

Step 2

Palmitic acid (300 mg, 1.17 mmol) was dissolved in DMF (6.0 mL) and dichloromethane (2.0 mL). DIEA (0.31 mL, 1.76 mmol) and HBTU (489 mg, 1.29 mmol) were added thereto, and the mixture was vigorously stirred at room temperature for 30 minutes. To the resulting cloudy solution, Compound 66 (409 mg, 1.17 mmol) was added at room temperature for three days. Aqueous saturated sodium bicarbonate solution (8.0 mL) and water (2.0 mL) were added to the reaction mixture to stop the reaction, and then white solid was collected by filtration. The resulting solid was washed with water (40 mL) to obtain Compound 67-14 (719 mg, quant.) as white solid.

$^1$H-NMR (DMSO-D6) δ: 7.89 (2H, d, J=7.4 Hz), 7.77 (1H, t, J=5.6 Hz), 7.70 (2H, d, J=7.4 Hz), 7.41 (2H, t, J=7.3 Hz), 7.33 (2H, t, J=7.3 Hz), 7.22 (1H, t, J=5.8 Hz), 4.95 (1H, s), 4.28-4.19 (3H, m), 3.51 (2H, t, J=5.6 Hz), 3.14-3.08 (2H, m), 3.02-2.89 (4H, m), 2.07 (2H, t, J=7.5 Hz), 1.47 (2H, s), 1.22 (19H, s), 0.94 (2H, d, J=6.5 Hz), 0.85 (3H, t, J=6.8 Hz).

ESI-MS (m/z): 552 (M+1).

Step 3

Compound 68-14 was synthesized from Compound 67-14 in a similar method to Steps 1 to 4 of 3-1).

ESI-MS (m/z): 1125 (M−H). HPLC Peak RT=1.09 min

Step 4

Compound 69-14 whose supported amount of Compound 68-14 is 108 μmol/g was synthesized in a similar method to Step 5 of 3-1).

15) Synthesis of Compound 74-k-n'

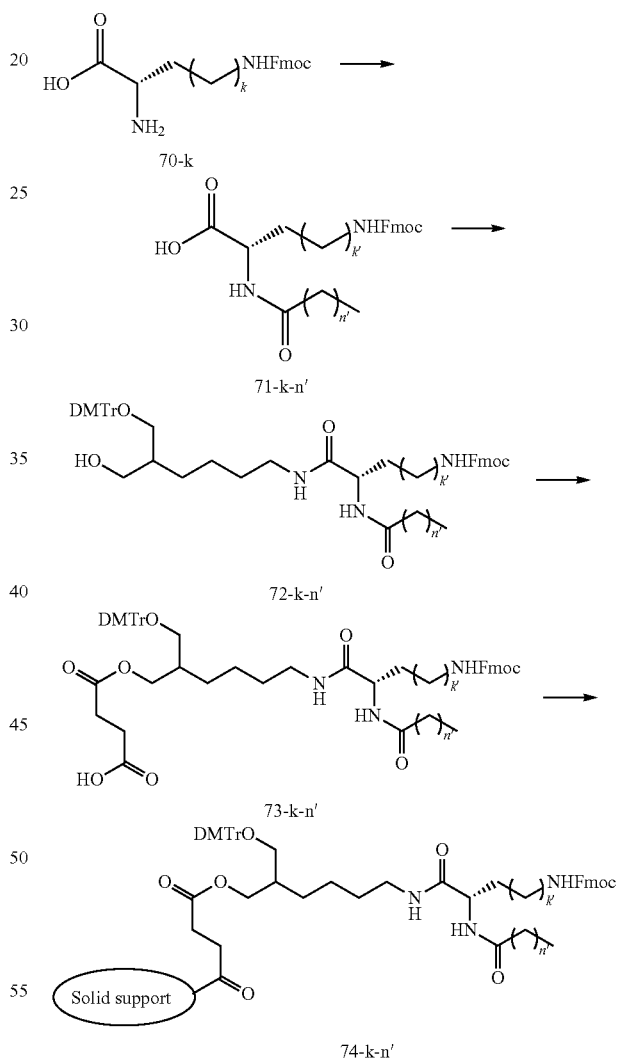

wherein k is an integer of 0 to 4, and n' is an integer of 5 to 29.

15-1) Synthesis of Compound 74-3-14

Step 1

Palmitic acid (209 mg, 0.81 mmol) was dissolved in DMF (6.0 mL). HBTU (309 mg, 0.81 mmol) was added thereto, and the mixture was stirred at room temperature for 10 minutes. To the reaction mixture, Compound 70-3 (300 mg, 0.81 mmol, Watanabe Chemical Industries, Ltd) and DIEA (0.14 mL, 0.81 mmol) were added, and the mixture was stirred at 50° C. for 5 minutes. Then, the mixture was stirred at room temperature for three hours. To the reaction mixture, 2 M hydrochloric acid was added, and the mixture was extracted with ethyl acetate. The organic layer was washed with brine, and dried over sodium sulfate. The solvent was distilled off under the reduced pressure, and the resulting crude product was purified by silica gel column chromatography (chloroform:methanol=100:0→90:10) to obtain Compound 71-3-14 (491 mg, 99%) as a white solid.

$^1$H-NMR (CDCl$_3$) δ: 7.76 (2H, d, J=7.4 Hz), 7.58 (2H, d, J=6.9 Hz), 7.39 (2H, t, J=7.3 Hz), 7.30 (2H, t, J=7.4 Hz), 6.43 (1H, d, J=7.3 Hz), 5.08 (1H, s), 4.58-4.18 (5H, m), 3.19-3.06 (3H, m), 2.21 (2H, t, J=7.6 Hz), 1.90-1.24 (30H, m), 0.87 (3H, t, J=6.5 Hz).

ESI-MS (m/z): 608 (M+1).

Step 2

Compound 71-3-14 (240 mg, 0.40 mmol) was suspended in acetonitrile (2.5 mL) and dichloromethane (5.0 mL). DIEA (0.21 mL, 1.19 mmol) and HBTU (165 mg, 0.44 mmol) were added thereto, and the mixture was stirred at room temperature for 15 minutes. 6-amino-2-((bis(4-methoxyphenyl) (phenyl) methoxy) methyl) hexane-1-ol (178 mg, 0.40 mmol), which synthesized with reference to US2009/259030, in acetonitrile (2.5 mL) was added to the reaction mixture, and the mixture was stirred at room temperature for three hours. Saturated sodium bicarbonate solution was added to the reaction mixture and the mixture was extracted with ethyl acetate. The organic layer was washed with water and brine and dried over sodium sulfate. The solvent was distilled off under reduced pressure, and the resulting crude product was purified by silica gel column chromatography (hexane:ethyl acetate=70:30→10:90) to obtain Compound 72-3-14 (146 mg, 36%) as a white solid.

$^1$H-NMR (CDCl$_3$): 7.76 (2H, d, J=7.5 Hz), 7.58 (2H, d, J=7.5 Hz), 7.39 (4H, t, J=7.4 Hz), 7.32-7.28 (8H, m), 7.20 (1H, t, J=7.3 Hz), 6.82 (4H, d, J=8.8 Hz), 6.21-6.15 (2H, m), 4.96 (1H, d, J=6.1 Hz), 4.42-4.28 (3H, m), 4.20 (1H, t, J=6.8 Hz), 3.78 (6H, s), 3.65-3.60 (2H, m), 3.24-3.18 (4H, m), 3.05 (1H, dd, J=9.1, 7.3 Hz), 2.62 (1H, t, J=5.6 Hz), 2.16 (2H, t, J=7.0 Hz), 1.84-1.76 (2H, m), 1.55-1.23 (38H, m), 0.88 (3H, t, J=6.8 Hz).

ESI-MS (m/z): 1039 (M+1).

Step 3

Compound 73-3-14 was synthesized from Compound 72-3-14 in a similar method to Steps 1 to 4 of 3-1).

ESI-MS (m/z): 1137 (M–H). HPLC Peak RT=1.34 min

Step 4

Compound 74-3-14 whose supported amount of Compound 73-3-14 is 120 μmol/g was synthesized in a similar method to Step 5 of 3-1).

16) Synthesis of Compound 75-n"

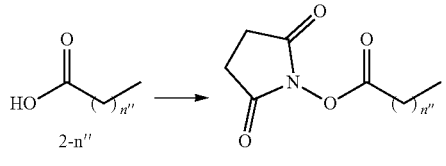

wherein n" is an integer of 2 to 29.

16-1) Synthesis of Compound 75-2

To Compound 2-2 (300 mg, 3.40 mmol) in THF (4.5 mL), N-hydroxysuccinic acid imide (431 mg, 3.75 mmol) was added. Next, N,N'-dicyclohexylcarbodiimide (773 mg, 3.75 mmol) in THF (1.5 mL) was added thereto, and the mixture was stirred at room temperature for two hours. After filtering off the resulting solid, the filtrate was concentrated to obtain Compound 75-2 (476 mg, 75%) as colorless oil.

$^1$H-NMR (CDCl$_3$) δ: 2.84 (4H, s), 2.59 (2H, t, J=7.3 Hz), 1.84-1.74 (2H, m), 1.05 (3H, t, J=7.5 Hz).

ESI-MS (m/z): 186 (M+1).

16-2) The following compounds were synthesized in a similar method to 16-1). Compound 75-6 (803 mg, 77%), white solid $^1$H-NMR (CDCl$_3$): 2.83 (4H, s), 2.60 (2H, t, J=7.5 Hz), 1.78-1.71 (2H, m), 1.42-1.29 (8H, m), 0.88 (3H, t, J=6.5 Hz).

ESI-MS (m/z): 242 (M+1).

Compound 75-10 (232 mg, 52%), white solid $^1$H-NMR (CDCl$_3$): 2.84 (4H, s), 2.60 (2H, t, J=7.5 Hz), 1.78-1.71 (2H, m), 1.42-1.20 (16H, m), 0.88 (3H, t, J=6.8 Hz).

ESI-MS (m/z): 298 (M+1).

Compound 75-12 (402 mg, 56%), white solid $^1$H-NMR (CDCl$_3$) δ: 2.83 (4H, s), 2.60 (2H, t, J=7.6 Hz), 1.78-1.70 (2H, m), 1.40 (2H, t, J=6.8 Hz), 1.26 (18H, s), 0.88 (3H, t, J=6.8 Hz).

Compound 75-16 (256 mg, 62%), white solid $^1$H-NMR (CDCl$_3$): 2.84 (4H, s), 2.60 (2H, t, J=7.5 Hz), 1.78-1.70 (2H, m), 1.44-1.26 (24H, m), 0.88 (3H, t, J=6.8 Hz).

Compound 75-18 (310 mg, 79%), white solid $^1$H-NMR (CDCl$_3$) δ: 2.84 (4H, s), 2.60 (2H, t, J=7.5 Hz), 1.78-1.70 (2H, m), 1.42-1.25 (32H, m), 0.88 (3H, t, J=6.8 Hz).

16-3) The following compounds were synthesized in a similar method to 16-1).

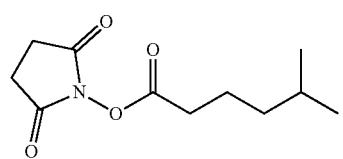

76

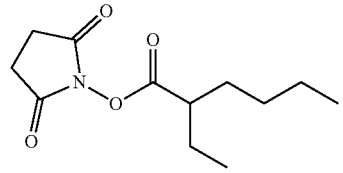

77

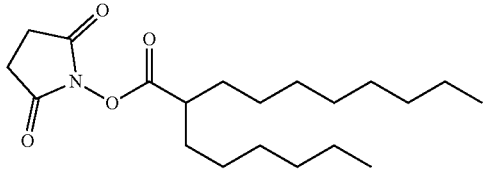

78

-continued

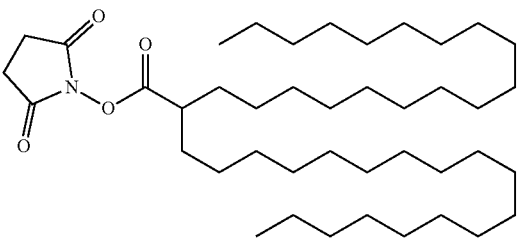
79

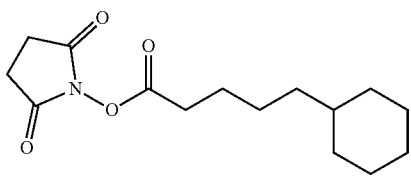
80

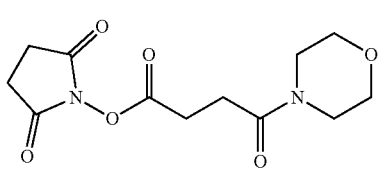
81

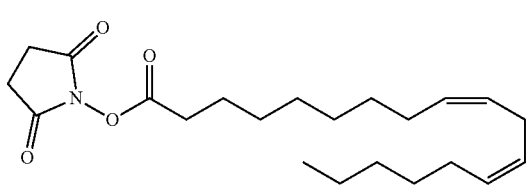
82

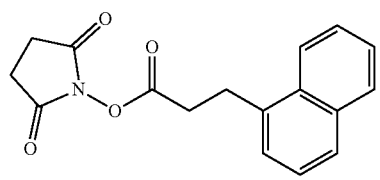
83

Compound 76 (429 mg, 82%), white solid
$^1$H-NMR (CDCl$_3$) δ: 2.84 (4H, s), 2.59 (2H, t, J=7.5 Hz), 1.79-1.71 (2H, m), 1.63-1.53 (1H, m), 1.32-1.26 (2H, m), 0.90 (6H, d, J=6.7 Hz).
ESI-MS (m/z): 228 (M+1).

Compound 77 (302 mg, 60%), colorless oil
$^1$H-NMR (CDCl$_3$): 2.83 (4H, d, J=4.0 Hz), 2.63-2.56 (1H, m), 1.82-1.56 (4H, m), 1.43-1.31 (4H, m), 1.03 (3H, t, J=7.5 Hz), 0.92 (3H, t, J=7.0 Hz).
ESI-MS (m/z): 242 (M+1).

Compound 78 (224 mg, 54%), colorless oil
$^1$H-NMR (CDCl$_3$) δ: 2.83 (4H, d, J=4.8 Hz), 2.68-2.61 (1H, m), 1.78-1.68 (2H, m), 1.63-1.54 (1H, m), 1.43-1.26 (20H, m), 0.89-0.86 (6H, m).

Compound 79 (296 mg, 84%), white solid
$^1$H-NMR (CDCl$_3$): 2.82 (4H, s), 2.68-2.60 (1H, m), 1.74-1.68 (2H, m), 1.61-1.56 (2H, m), 1.40-1.25 (64H, m), 0.88 (6H, t, J=6.5 Hz).

Compound 80 (373 mg, 82%), white solid
$^1$H-NMR (CDCl$_3$): 2.83 (4H, s), 2.60 (2H, t, J=7.5 Hz), 1.76-1.67 (6H, m), 1.45-1.37 (2H, m), 1.26-1.11 (7H, m), 0.90-0.82 (2H, m).
ESI-MS (m/z): 282 (M+1).

Compound 81 (476 mg, quant.), white oil
$^1$H-NMR (CDCl$_3$) δ: 3.68-3.63 (6H, m), 3.49-3.47 (2H, m), 3.01 (2H, t, J=7.1 Hz), 2.87-2.82 (4H, m), 2.74 (2H, t, J=7.1 Hz).
ESI-MS (m/z): 285 (M+1).

Compound 82 (459 mg, quant.), colorless oil
$^1$H-NMR (CDCl$_3$) δ: 5.40-5.33 (4H, m), 2.83 (4H, s), 2.77 (2H, t, J=6.3 Hz), 2.60 (2H, t, J=7.5 Hz), 2.05 (4H, q, J=6.7 Hz), 1.78-1.71 (2H, m), 1.43-1.26 (14H, m), 0.89 (3H, t, J=6.7 Hz).
ESI-MS (m/z): 378 (M+1).

Compound 83 (433 mg, quant.), colorless oil
$^1$H-NMR (CDCl$_3$) δ: 8.01 (1H, d, J=8.3 Hz), 7.88 (1H, d, J=7.9 Hz), 7.77 (1H, d, J=7.7 Hz), 7.58-7.49 (2H, m), 7.45-7.39 (2H, m), 3.53 (2H, t, J=8.0 Hz), 3.06 (2H, t, J=8.0 Hz), 2.86 (4H, s).
ESI-MS (m/z): 298 (M+1).

17) Synthesis of Compound 84

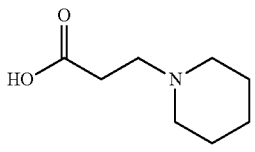

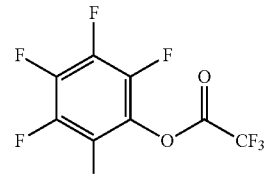
85

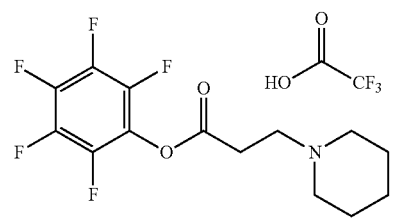
86

To Compound 84 (200 mg, 1.27 mmol, Watanabe Chemical Industries, Ltd) in dichloromethane (4.0 mL), Compound 85 (0.22 mL, 1.27 mmol, Wako Pure Chemical Industries, Ltd.) was added, and the mixture was stirred at room temperature for six hours. The reaction mixture was concentrated to obtain the crude product of Compound 86 (563 mg) as colorless oil.

ESI-MS (m/z): 324 (M+H). HPLC Peak RT=1.29 min

18) Synthesis of Compound 88

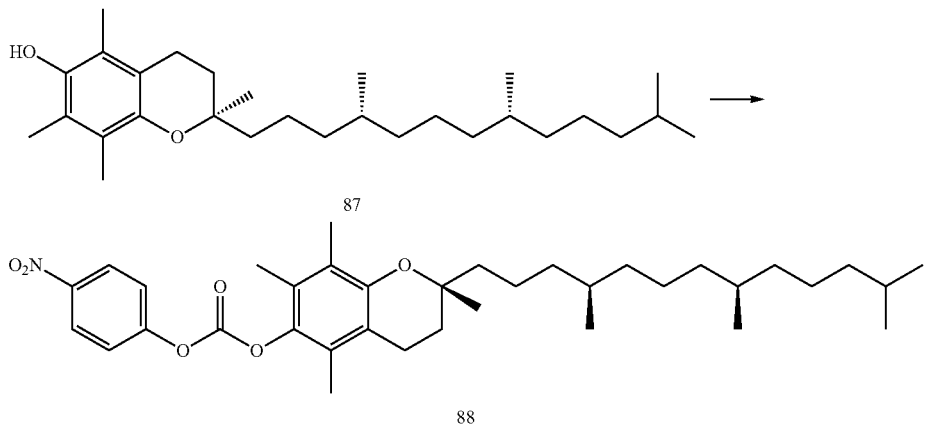

To Compound 87 (800 mg, 1.86 mmol) in dichloromethane (5.0 mL), bis(4-nitrophenyl)carbonate (848 mg, 2.79 mmol) and triethylamine (0.39 mL, 2.79 mmol) were added, and the mixture was stirred at room temperature for 24 hours. After the solvent was distilled off, the resulting crude product was purified by silica gel column chromatography (hexane: ethyl acetate=100:0→90:10) to obtain Compound 88 (1.21 g, quant.) as yellow oil.

$^1$H-NMR (CDCl$_3$): 8.31 (2H, d, J=9.2 Hz), 7.48 (2H, d, J=9.2 Hz), 2.62 (2H, t, J=6.7 Hz), 2.16 (3H, s), 2.12 (6H, s), 1.87-1.74 (2H, m), 1.60-1.05 (24H, m), 0.87-0.83 (12H, m).

ESI-MS (m/z): 596 (M+1).

19) Synthesis of Compound 90-k-n'

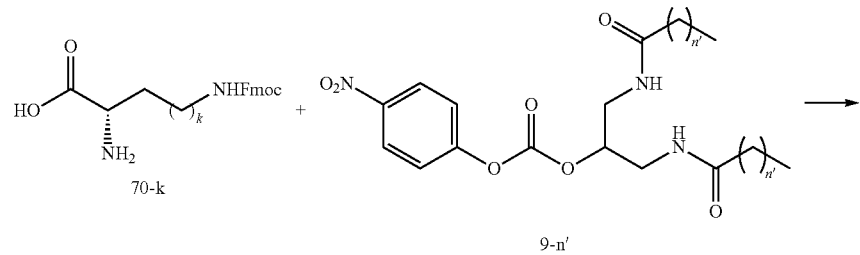

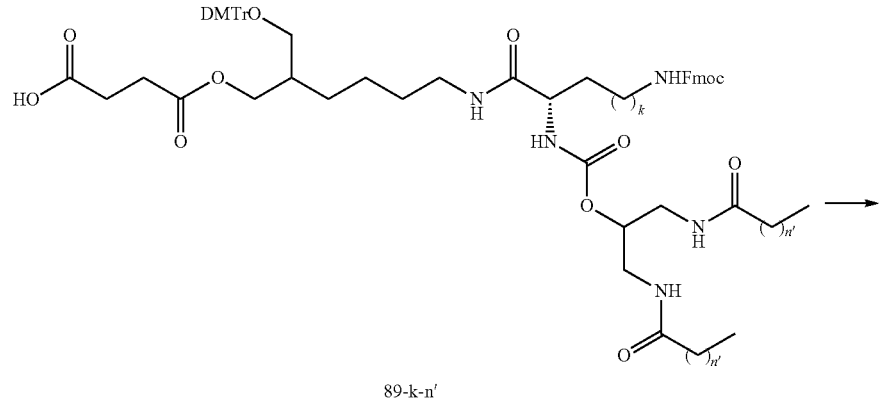

-continued

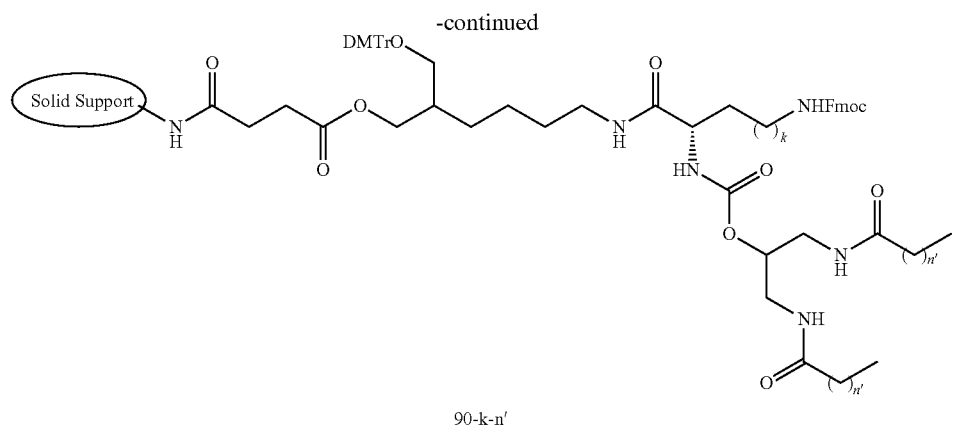

90-k-n' wherein k is an integer of 0 to 4, n' is an integer of 5 to 29.

19-1) Synthesis of Compound 90-3-12

Step 1

Compound 89-3-12 was synthesized from Compound 70-3 and Compound 9-12 in a similar method to Steps 1 to 3 of 15-1).

LC/MS: Rt=2.48 min [M−] m/z: 1435

Step 2

Compound 90-3-12 whose supported amount of Compound 89-3-12 is 68 μmol/g was synthesized in a similar method to Step 5 of 3-1).

20) Synthesis of Compound 95-k-n'

20-1) Synthesis of Compound 95-3-12

Step 1

Compound 92-3-12 was synthesized from Compound 91-3 in a similar method to Step 1 of 15-1) as pale red solid (1.11 g).

$^1$H-NMR (CDCl$_3$) δ: 6.16 (1H, d, J=7.7 Hz), 5.64 (1H, m), 4.58 (1H, td, J=8.1, 4.6 Hz), 3.74 (3H, s), 3.27-3.23 (2H, m), 2.23-2.16 (4H, m), 1.86-1.82 (2H, m), 1.74-1.28 (48H, m), 0.88 (6H, t, J=6.8 Hz).

Step 2

Compound 92-3-12 (1.17 g) was dissolved in THF (12 mL). 2 M sodium hydroxide solution (2 mL) was added thereto, and the mixture was stirred overnight. The precipitate produced by adding acetonitrile (40 mL) was collected

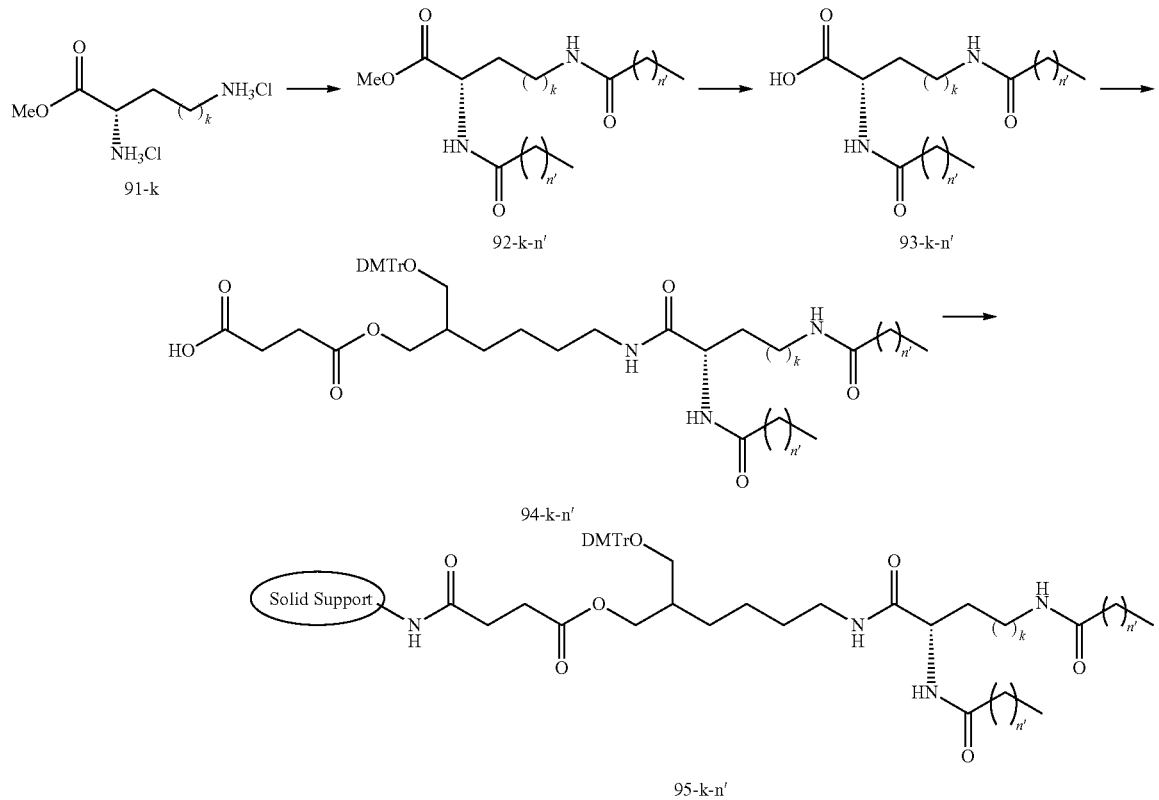

wherein k is an integer of 0 to 4, and n' is an integer of 5 to 29.

by filtration to obtain the crude solid. Then, it was dissolved in ethyl acetate (50 mL), and the organic layer was washed with 1 M hydrochloric acid solution (40 mL). The organic layer was washed with water, dehydrated in brine, dried over anhydrous sodium sulfate, filtered, and concentrated under reduced pressure to obtain Compound 93-3-12 as a colorless solid (199 mg) (Yield: 18%).

$^1$H-NMR (CDCl$_3$) δ: 6.82 (1H, d, J=7.0 Hz), 5.81 (1H, t, J=6.0 Hz), 4.51 (1H, td, J=7.4, 4.6 Hz), 3.37 (1H, td, J=13.8, 6.9 Hz), 3.18 (1H, dt, J=19.4, 5.7 Hz), 2.33-2.25 (2H, m), 2.19 (2H, t, J=7.7 Hz), 1.95-1.77 (2H, m), 1.63-1.25 (49H, m), 0.88 (6H, t, J=6.8 Hz).

Step 3

Compound 94-3-12 was synthesized from Compound 93-3-12 in a similar method to Step 1 of 3-1).

m/z 1097.84[M−H]

Step 4

Compound 95-3-12 whose supported amount of Compound 94-3-12 is 84 µmol/g was synthesized in a similar method to Step 5 of 3-1).

20-2) The following compounds were synthesized in a similar method to 20-1).

Compound 94-3-14

1H-NMR (CDCl$_3$) δ: 7.35-6.82 (13H), 6.47 (1H, m), 6.20 (1H, t, 6 Hz), 6.02 (1H, t, 6 Hz), 4.51 (1H, q, J=7.5 Hz), 4.42 (1H, dd, J=8.1, 3.6 Hz), 4.18 (1H, d, J=5.6 Hz), 4.09 (1H, dd, J=11.0, 4.3 Hz), 3.77 (6H, s), 3.42-2.97 (8H, m), 2.72-1.74 (12H, m), 1.60-1.15 (58H, m), 0.88 (6H, t, J=6.8 Hz).

Compound 95-3-14 whose supported amount of Compound 94-3-14 is 60 µmol/g Compound 94-3-16

1H-NMR (CDCl$_3$) δ: 8.02-6.81 (13H), 6.40 (1H, dd, J=8.9, 4.4 Hz), 6.18 (1H, t, J=6.4 Hz), 5.97 (1H, t, J=6.5 Hz), 4.53 (1H, dd, J=15.9, 7.4 Hz), 4.44 (1H, d, J=11, 4 Hz), 4.20-4.15 (11H, m), 4.09 (1H, dd, J=11.1, 4.0 Hz), 3.79 (6H, s), 3.45-3.00 (8H, m), 2.78-2.42 (4H, m), 2.20 (4H, m), 2.04-1.24 (62H, m), 0.88 (6H, t, J=6.8 Hz).

Compound 95-3-16 whose supported amount of Compound 94-3-16 is 65 µmol/g Compound 94-2-14 m/z 1138.74 [M−H]

Compound 95-2-14 whose supported amount of Compound 94-2-14 is 77 µmol/g

21) Synthesis of Compound 97

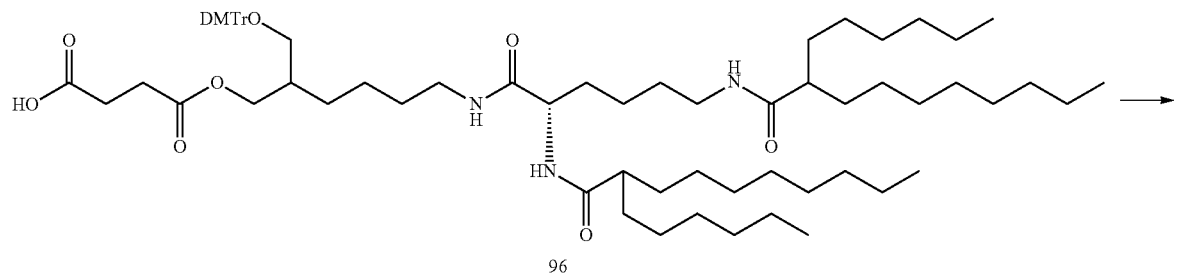

96

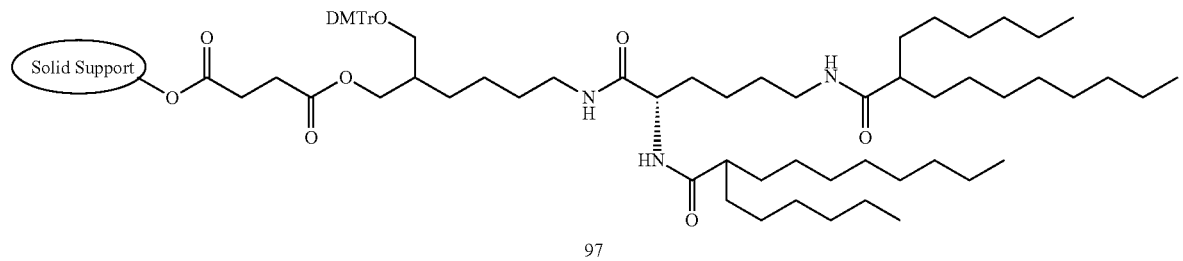

97

Step 1

Compound 96 was synthesized from Compound 78 in a similar method to Steps 1 to 3 of 20-1).

m/z 1153.04[M−H]

Step 2

Compound 97 whose supported amount of Compound 96 is 52 µmol/g was synthesized in a similar method to Step 5 of 3-1).

22) Synthesis of Compound 100-j-n'

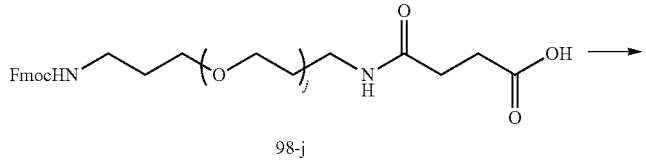

98-j

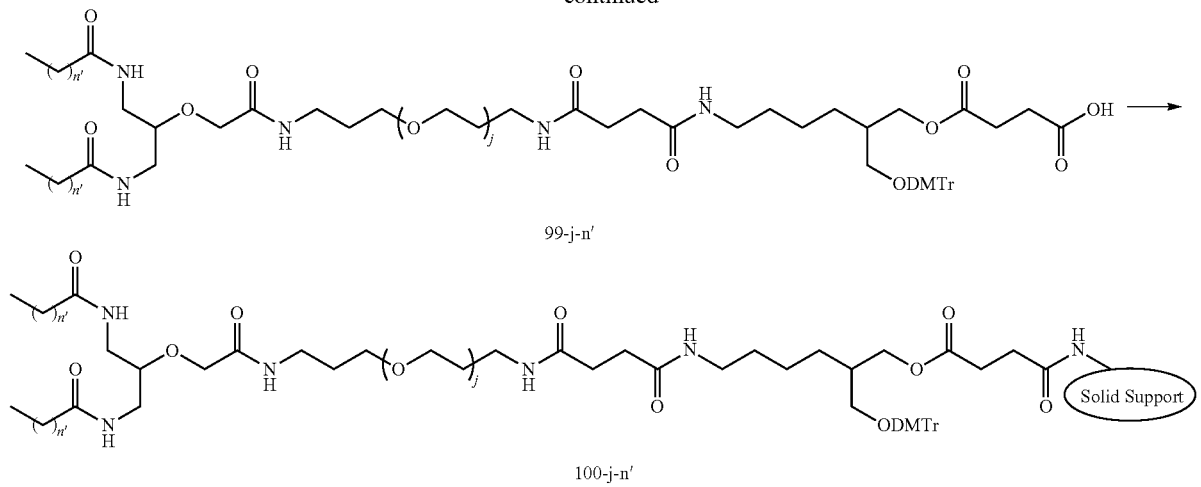

99-j-n′

100-j-n′ wherein j is an integer of 1 to 3, and n' is an integer of 5 to 29.

22-1) Synthesis of Compound 100-3-18

Step 1

Compound 99-3-18 was synthesized from Compound 98-3 in a similar method to Steps 1 to 3 of 15-1).

1H-NMR (CDCl$_3$) δ: 7.42 (2H, d, J=7.4 Hz), 7.30 (5H, d, J=8.7 Hz), 7.19 (1H, t, J=7.2 Hz), 6.81 (5H, d, J=8.7 Hz), 6.74 (1H, t, J=5.8 Hz), 6.26 (1H, t, J=5.9 Hz), 5.55 (1H, t, J=5.9 Hz), 4.72-4.67 (1H, m), 3.79 (6H, s), 3.58-3.49 (17H, m), 3.32-3.27 (6H, m), 3.14 (2H, q, J=6.5 Hz), 3.04 (2H, d, J=5.4 Hz), 2.49-2.46 (4H, m), 2.20 (5H, t, J=7.5 Hz), 1.76-1.72 (4H, m), 1.65-1.62 (10H, m), 1.42-1.41 (3H, m), 1.25 (68H, s), 0.88 (6H, t, J=6.6 Hz).

Step 2

Compound 100-3-18 whose supported amount of Compound 99-3-18 is 56 μmol/g was synthesized in a similar method to Step 5 of 3-1).

23) Synthesis of Compound 101 and 102

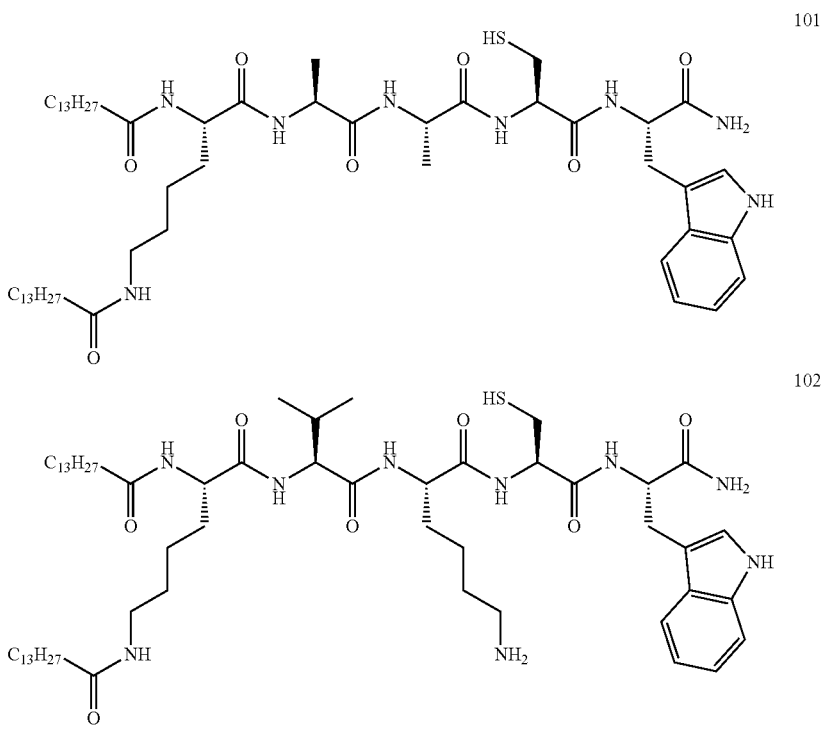

With the resin (Fmoc-NH-SAL resin, 100 μmol, Watanabe Chemical Industries, Ltd) settled in the column with filter, deprotection reaction (20% piperidine 2 mL/100 μmol resin) and condensation reaction (300 μmol protected amino acids, 300 μmol HBTU, 300 μmol 1-hydroxybenzotriazole monohydrate, 600 μmol DIEA, DMF/NMP (1:1) 2 mL/100 μmol resin) were repeated to extend peptide chains.

For synthesis of N terminal region of peptide, after peptide elongation and deprotection reaction as the above with Fmoc-Lys(Fmoc)-OH (Watanabe Chemical Industries, Ltd), myristic acid was condensed with the peptide on the resin (300 μmol myristic acid, 300 μmol HBTU, 600 μmol DIEA, chloroform/NMP (1:1) 2 mL/100 μmol resin) to synthesize a lipidated peptide. Cleavage solution (TFA 92.5%, H$_2$O 2.5%, TIS 2.5%, DODT 2.5%, 2 mL/100 μmol resin) was added to the synthesis column, reacted at room temperature for one hour, and filtered. The solvent (acetonitrile or water) was added to the filtrate and the precipitate was collected. The precipitate was dissolved in DMSO, and purified by reversed phase (YMC Pack C4, 150×10 mm I.D., Flow rate: 3-5 mL/min, 10 mM TEAA-acetonitrile, isocratic elution (Washed with 50% acetonitrile, and then eluted with 95% acetonitrile), Detection 260 nm, 280 nm). The collected fraction was condensed and lyophilized to obtain the lipid-peptide (e.g., Compound 101 or Compound 102) as white solid. Compound 101 [M+H]+, calc. 997.68824, obs. 997.4476 Compound 102 [M+H]+, calc. 1082.77739, obs. 1082.7048

24) Synthesis of Compound 103

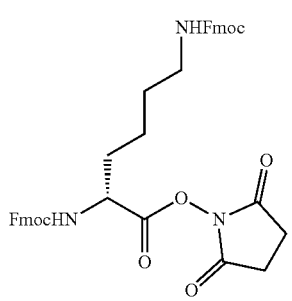

Compound 103 was synthesized from Fmoc-D-Lys (Fmoc)-OH (Watanabe Chemical Industries, Ltd) in a similar method to 16-1).

ESI-MS, [M+H]+ calc. 688.26534, obs. 688.4007

24) Synthesis of Compound 105-n'

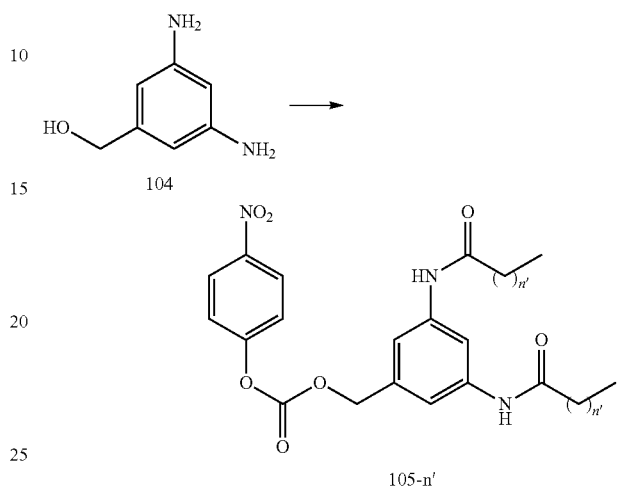

wherein n' is an integer of 5 to 29.

24-1) Synthesis of Compound 105-14

Compound 105-14 was synthesized from Compound 104 in a similar method to Step 1 of 1-1) and Step 1 of 3-1)

ESI-MS (m/z): 779 (M−H).

25) Synthesis of Compound 112

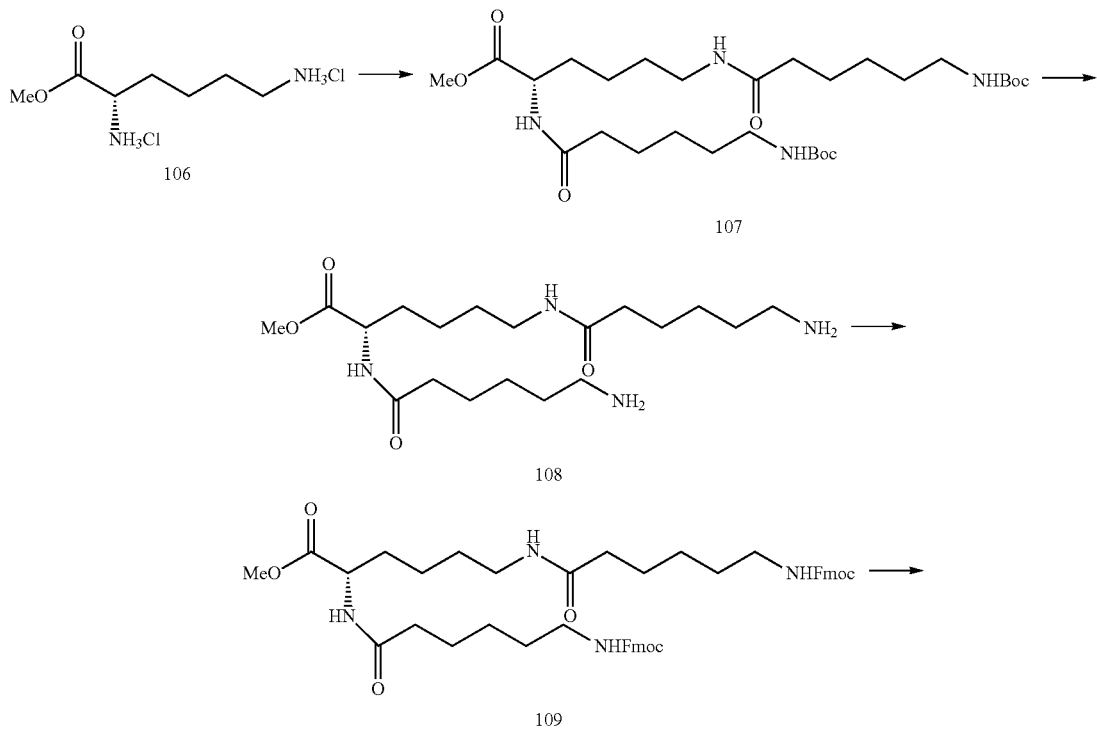

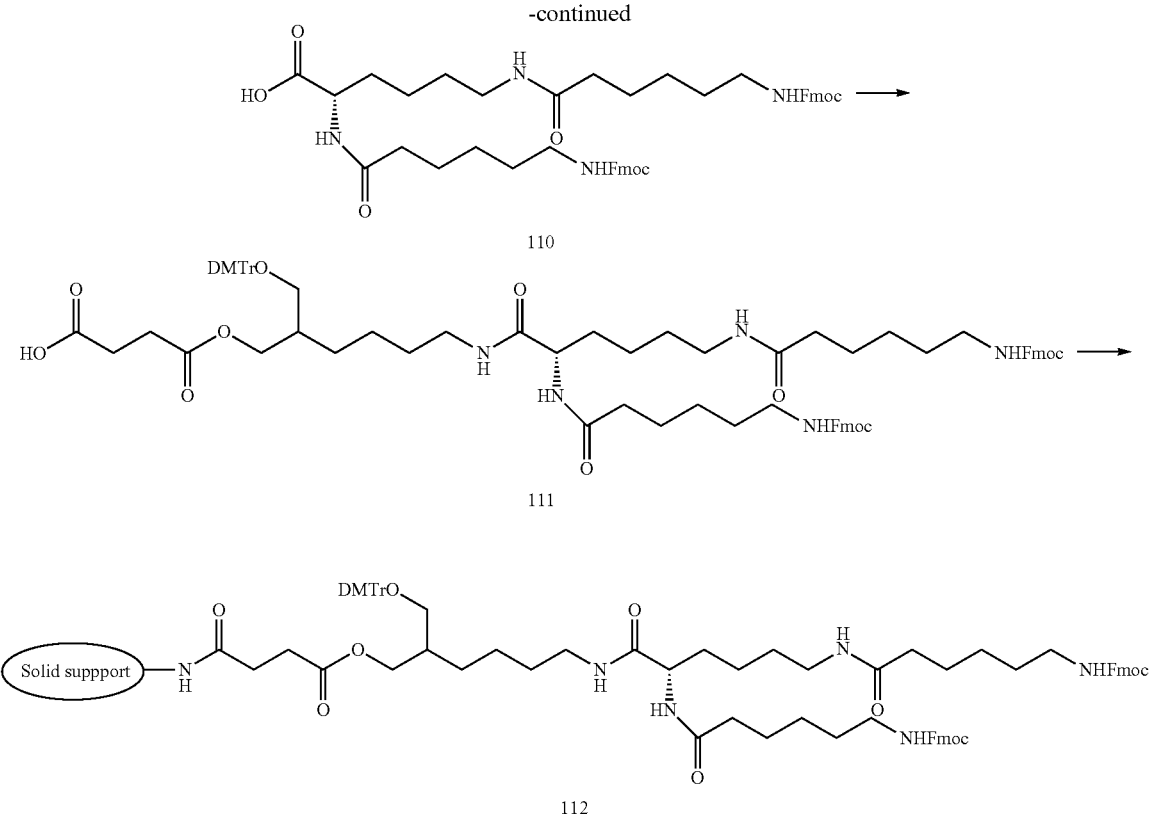

Step 1

6-N-Boc-caproic acid (1.0 g, Sigma-Aldrich) was dissolved in DMF (20 mL). DIEA (2.3 mL) and HBTU (1.8 g) were added thereto, and the mixture was stirred at room temperature for 15 minutes. Compound 106 (0.45 g, Tokyo Chemical Industry Co., Ltd.) was added thereto, and the mixture was stirred at room temperature overnight. The reaction mixture was poured into saturated sodium bicarbonate solution (50 mL), and extracted with ethyl acetate (100 mL). The organic layer was concentrated under reduced pressure and the residue was purified by flash chromatography (silica gel, A solvent: chloroform/B solvent: 25% methanol chloroform, gradient: 0→5% B solvent for 15 minutes) to obtain Compound 107 as brown oil (1.12 g)(Yield 44%).

m/z 585.19[M−H]− (ES Negative mode), Theoretical value 586.394[M]

Step 2

Compound 107 (1.12 g) was dissolved in dichloromethane (5.6 mL). TFA (5.6 mL) was added thereto, and the mixture was stirred at room temperature for 30 minutes. Then, the mixture was coevaporated with toluene twice to remove TFA and dried to obtain Compound 108 as orange oil (1.9 g).

m/z 387.44[M+H]+ (ES Positive mode), Theoretical value 386.289[M]

Step 3

Compound 108 (1.9 g) was dissolved in 1,4-dioxane/water (1:1, 14.6 mL), and sodium hydrogen carbonate (1.58 g) was added thereto. 9-fluorenylmethyl chloroformate (1.08 g) was added to the mixture and the mixture was stirred under heating. Sodium hydrogen carbonate (0.79 g) was added thereto, and the mixture was cooled to room temperature. The solid was collected by filtration. The solid was redissolved in ethyl acetate, n-hexane was added thereto. The precipitated solid was collected by filtration and dried to obtain Compound 109 (1.93 g) as a white solid.

m/z 831.46[M+H]+ (ES Positive mode), Theoretical value 830.425[M]

Step 4

Compound 109 (0.50 g) was suspended in dichloromethane (5 mL), and N,N-dimethylaniline (0.61 mL) and aluminium (III) chloride (0.40 g) were added thereto. The mixture was stirred under reflux for one hour, and the reaction was stopped by adding dropwise 1 M hydrochloric acid (20 mL). The mixture was extracted with ethyl acetate (2×30 mL), and the resulting organic layer was washed with water (2×30 mL). Then, it was dehydrated in brine, concentrated to dryness, and purified by flash chromatography (Silica type, A solvent chloroform/B solvent 25% methanol chloroform, gradient: 0→50% B solvent for 12 minutes) to obtain Compound 110 as colorless solid (32 mg) (Yield 7%).

m/z 815.32[M−H]− (ES Negative mode), Theoretical value: 816.410[M]

Step 5

Compound 111 was synthesized from Compound 110 in a similar method to Step 4 of 3-1).

m/z 1248.38[M+H]+ (ES Positive mode), Theoretical value: 1247.656[M]

Step 6

Compound 112 whose supported amount of Compound 111 is 45 μmol/g was synthesized in a similar method to Step 5 of 3-1).

26) Synthesis of Compound 120

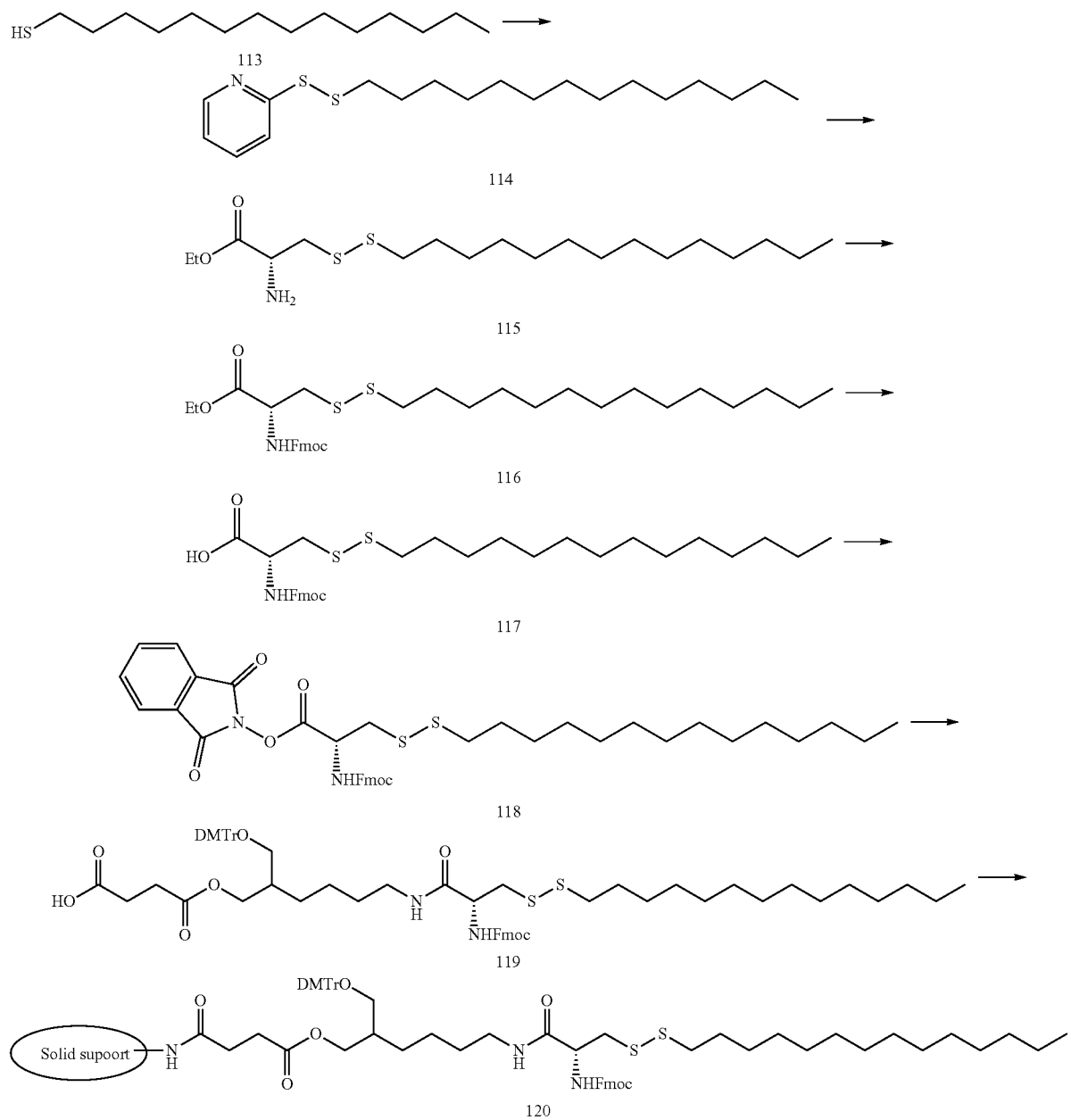

Step 1

Compound 113 (2 g, Sigma-Aldrich) was dissolved in methanol (20 mL), and 1,2-di(pyridine-2-yl)disulphane (1.91 g) was added thereto. The mixture was stirred at room temperature for one day. The reaction was stopped by adding dropwise to 1 M hydrochloric acid solution (50 mL), and the mixture was extracted with ethyl acetate (2×50 mL). The resulting organic layer was concentrated to obtain Compound 114 as yellow oil (2.44 g)(Yield 83%).

m/z 340.38[M+H]+ (ES Positive mode), Theoretical value 339.205[M]

Step 2

Compound 114 (1.22 g) was dissolved in methanol (2 mL). Ethyl L-cysteine hydrochloride (0.53 g) was added thereto, and the mixture was stirred at room temperature overnight. After adding acetonitrile (5 mL), the precipitated solid was collected by filtration. The solid was washed with acetonitrile and dried to obtain Compound 115 as colorless solid (0.98 g) (Yield 72%).

m/z 378.96[M+H]+(ES Positive mode), Theoretical value 377.242[M]

Step 3

Compound 115 (400 mg) was dissolved in 1,4-dioxane (4 mL), tetrahydrofuran (4 mL) and water (1 mL). Sodium hydrogen carbonate (222 mg), DIEA (462 µL) and 9-fluorenylmethyl chloroformate (174 mg) were added thereto, and the mixture was stirred at room temperature for three hours. 9-fluorenylmethyl chloroformate (80 mg) was added, and the mixture was stirred at room temperature for one hour to complete the reaction. After addition of water (50 mL), the mixture was extracted with ethyl acetate (50 mL), and the resulting organic layer was washed with brine. The organic layer was concentrated under reduced pressure and purified by flash chromatography (silica type, A solvent: n-hexane/B solvent: ethyl acetate, gradient: 0→20% B solvent for 20 minutes) to obtain Compound 116 as colorless amorphous (534 mg) (Yield 84%).

m/z 599.64[M+H]+(ES Positive mode), Theoretical value: 599.310[M]

Step 4

Compound 116 (534 mg) was dissolved in tetrahydrofuran (5.3 mL). 1 M aqueous sodium hydroxide solution (2 mL) was added thereto, and the mixture was stirred at room temperature overnight. 1 M aqueous hydrochloric acid solution (40 mL) and ethyl acetate (40 mL) were added to the reaction mixture, and the resulting organic layer was separated and washed twice with water. The organic layer was washed with brine, concentrated under reduced pressure, and purified by flash chromatography (silica type, A solvent: chloroform/B solvent: 25% methanol chloroform, gradient: 0→20% B solvent for 15 minutes) to obtain the target Compound 117 as colorless oil (30 mg)(Isolated yield: 6%).

m/z 572.34[M+H]+(ES Positive mode), Theoretical value: 571.279[M]

Step 5

Compound 118 was synthesized from Compound 117 in a similar method to Step 1 of 16-1).

m/z 572.34[M+H]+(ES Positive mode), Theoretical value: 571.279[M]

Step 6

Compound 119 was synthesized from Compound 118 in a similar method to Step 4 of 3-1).

m/z 1024.34[M+Na]+ (ES Positive mode), Theoretical value: 1024.52[M+Na]+

Step 7

Compound 120 whose supported amount of Compound 119 is 32 μmol/g was synthesized in a similar method to Step 5 of 3-1).

27) About the Other Compounds

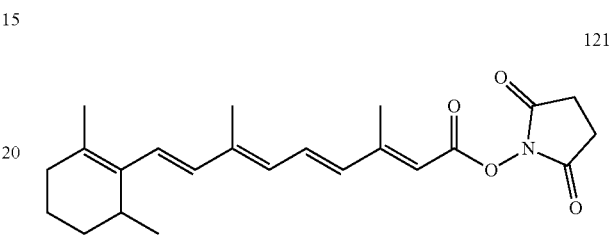

121

Compound 121 was synthesized according to the methods described in U.S. Pat. No. 6,153,737.

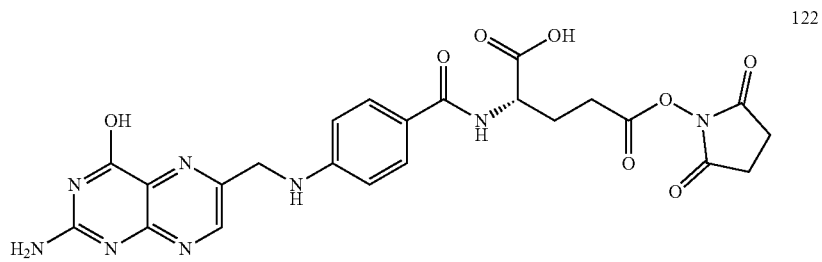 [SMILES: Nc1nc(O)c2nc(CNc3ccc(C(=O)N[C@@H](CCC(=O)ON4C(=O)CCC4=O)C(=O)O)cc3)cnc2n1]

122

Compound 122 was synthesized according to the methods described in Non-Patent Document Journal of the American Chemical Society, 2008, 130, 11467-11476.

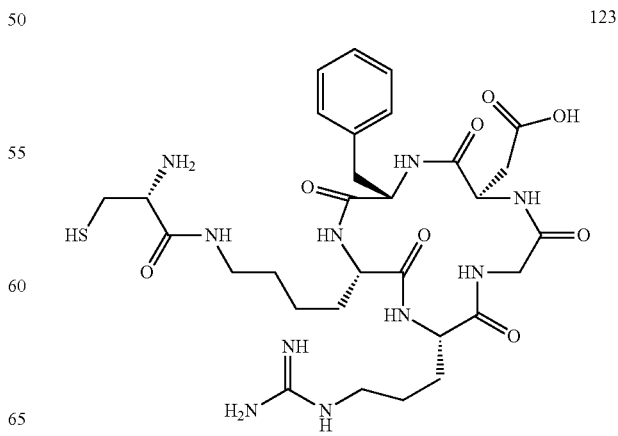

123

Compound 123 was purchased from Sigma-Aldrich.

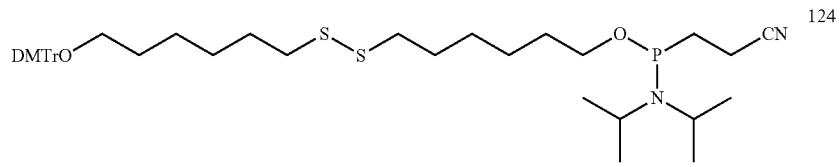

Compound 124 was purchased from Link-Technologies Ltd.

B) Synthesis of Oligonucleotides

Oligonucleotides used in examples of this description were synthesized using phosphoramidite method by AKTA Oligopilot10 (GE Healthcare), NS-8-I (Dainippon Seiki co., ltd.) or NS-8-II (Dainippon Seiki co., ltd.). A monomer was prepared in 0.1 M acetonitrile solution using the amidite derived from the above amidite synthesis. The coupling time was 32 seconds to 10 minutes, and 8 to 10 equivalents of the amidite unit were used to condense with one monomer. 0.02 M Oxidizer (Sigma-Aldrich) and iodine/pyridine/water/=12.7/9/1 (w/v/v) were used for PO oxidation. 50 mM DDTT ((dimethylamino-methylidyne) amino-3H-1,2,4-dithiazoline-3-thion) in acetonitrile/3-picoline 1/1(v/v) or 1/4(v/v) and acetonitrile/pyridine 1/4 (v/v) solution were used for PS oxidation. ETT activator (5-ethylthio)-1H-tetrazole) (Sigma-Aldrich) was used as an activator, CapA and CapB (Sigma-Aldrich) was used as a capping reagent. Deb (3 w/v % TCA CH$_2$C12 solution) (Wako Pure Chemical Industries, Ltd.) or Deb (3 w/v % Dichloroacetic acid, Toluene Solution) was used as a detritylation reagent.

NA-6, NA-7, NA-21 and NA-23 were derived by consigning synthesis and purification of oligonucleotides to GeneDesign Inc.

C) Synthesis of Lipid Conjugated Oligonucleotides

1) Synthesis-1 from a Synthesized Amidite Unit

With a synthesized amidite (e.g., Compound 5-n') synthesized in the above A), the target lipid conjugated oligonucleotides were synthesized in a similar way as the above B).

2) Synthesis-2 from a Synthesized Amidite Unit

A stirrer, Molecular Sieves 4A 1/16 and the amidite synthesized in the above A) (e.g., Compound 5-n'. 10 to 100 equivalents of an oligonucleotide) were put in a microwave tube (2-5 ml, 10-20 ml) made by Biotage, and the solution was adjusted to 0.2 M with chloroform (added 2-methyl-2-butane as a stabilizer). After drying for five hours, oligonucleotides supported to solid phase (CPG resin or polystyrene resin) and 0.25 M ETT activator, which is ((5-ethylthio)-1H-tetrazole) in dichloromethane, (the same amount of chloroform) were added, sealed and heated at 40° C. for 10 minutes to one hour. After cooling to room temperature, the reaction mixture was diluted twice with chloroform, and the resin was collected by filtration. The resulting resin was used in PS oxidization in NS-8-I (Dainippon Seiki co., ltd.) or NS-8-II (Dainippon Seiki co., ltd.). Then the dried resin was subject to deprotection of the following D) to synthesize the target lipid conjugated oligonucleotide.

3) Synthesis from Lipid-Supported Resin

Using a lipid-supported resin synthesized in the above A) (e.g., Compound 13-n', Compound 27-n' and Compound 33-s'-t'-u'), the target lipid conjugated oligonucleotides were synthesized in a similar method to the above B).

4) Synthesis from an Activator

A single-stranded oligonucleotide comprising an amino linker (e.g., NA-23 or NA-24) was put in a microfuge tube (1.5 ml), DMSO (addition of 0.5% DIEA) and sodium bicarbonate solution (0.2 M NaHCO$_3$) were added as 1:5 to prepare in 1 mM. The compound synthesized in the above A) (e.g., Compound 14-n'. 2 to 10 equivalents of an oligonucleotide as DMSO solution) was added thereto and the mixture was allowed to stand from a room temperature to 70° C. for two hours to synthesize the target lipid conjugated oligonucleotide.

5) Synthesis from Lipid Conjugated Amino Acid

A single-stranded oligonucleotide comprising an amino linker (e.g., NA-23, NA-24) (1.2 μmol) and 6-maleimido-hexanoic acid N-hydroxysuccinimide ester (26 μmol) were mixed and reacted under the presence of 0.1% DIEA in DMSO (1 mL) at room temperature for two to four hours. The reaction mixture was ultrafiltered, and then lyophilizated to obtain white solid.

The resulting white solid and a compound synthesized in the above A) (e.g., Compound 100 or Compound 101. 2 to 50 equivalents of an oligonucleotide) were dissolved in 4 mL of the solvent (DMSO/acetonitrile (1:1) or DMSO) and reacted at room temperature to synthesize the target lipid conjugated oligonucleotide.

6) Synthesis from Lipid-Peptide

To a single-stranded oligonucleotide comprising an amino linker (e.g., NA-23 or NA-24) in 25 mM phosphate buffer solution (pH 7.4), 10 equivalents of NHS-PEG4-Maleimide (ThermoFisher Scientific) was added and the mixture was stirred at room temperature for five hours. The excess NHS-PEG4-Maleimide was removed from the reaction mixture with Ultrafiltration kit (molecular weight cut off: 3,000). Then, a compound synthesized in the above A) (e.g., Compound 123. 3 to 10 equivalents of an oligonucleotide) was added and reacted at 40° C. for one hour to synthesize the target lipid conjugated oligonucleotide.

D) Cleavage/Deprotection

1) Cleavage from the Resin, and Phosphate Deprotection and Base Deprotection

For cutting out DNA oligonucleotide, 28% ammonia water/40% methylamine solution/EtOH=4/4/1(v/v) was used and the solution was shaken at room temperature for four hours. 1 ml, 5 ml or 10 ml of ammonia solution was used for 1 μmol, 5 μmol or 10 μmol synthesis, respectively, for cutting out reaction. After the resin was washed with 50% ethanol water, the filtrate was concentrated under reduced pressure to about 1 to 5 mL.

2) Fmoc and Phosphate Deprotection on the Resin

After completion of synthesis of 5) of C), the resin was washed with 20% piperidine in DMF solution.

E) Purification

Oligonucleotides without a lipid were purified by reversed phase HPLC in Condition 1.
Condition for Reversed Phase HPLC
Condition 1
Mobile Phases
Buffer A: 100 mM TEAA (triethylammonium acetate, pH 7.0) aqueous solution or 100 mM AcONa aqueous solution (pH5.4)
Buffer B: acetonitrile
B concentration gradient: 10-30%
(Condition 1-1)
Column: Hydrosphere C18 (YMC co., ltd.) 100×20 mm I.D, S-5 μm, 12 nm
Flow rate: 10 mL/min
Column temperature: room temperature
Detection UV: 260 nm
(Condition 1-2)
Column: Hydrosphere C18 (YMC co., ltd.) 150×10 mm I.D, S-5 μm, 12 nm
Flow rate: 4 mL/min
Column temperature: room temperature
Detection UV: 260 nm Oligonucleotides with a lipid were purified by reversed phase HPLC in Condition 2.
Condition 2
Condition for reversed phase HPLC
According to lipid solubility of the compound, B concentration at the beginning was adjusted from 20% to 50%.
Mobile Phases
Buffer A: 100 mM TEAA (Triethylammonium acetate pH 7.0) aqueous solution or 100 mM AcONa aqueous solution (pH 5.4)
Buffer B: acetonitrile
B concentration gradient: 20-80%
(Condition 2-1)
Column: YMC-Pack C4 (YMC co., ltd.) 100×20 mm I.D, S-5 μm, 12 nm
Flow rate: 10 mL/min
Column temperature: room temperature
Detection UV: 260 nm
(Condition 2-2)
Column: YMC-Pack C4 (YMC co., ltd.) 150×10 mm I.D, S-5 μm, 12 nm
Flow rate: 4 mL/min
Column temperature: room temperature
Detection UV: 260 nm F) Desalting and freeze-drying of the purified oligonucleotide Using VivaSpin20 (MWCO 3000) (Sartorius) and Amicon Ultra-4 Centrifugal Filter Units-3K, ultrafiltration was repeated for the resulting oligonucleotide to remove salt component from the fraction. Then, it was lyophilized to obtain the target oligonucleotide as powder. For the oligonucleotides purified using TEAA solvent, the desalting procedure was carried out after transforming the salt form with 100 mM sodium acetate solution (20 mL).

G) Structural Elucidation of Oligonucleotides

The resulting oligonucleotides were confirmed as the target sequences by matching the found molecular weights determined by UPLC/MS measurement and the calculated molecular weights.
Condition 1 (The oligonucleotides without lipid)
Xevo G2 Tof System (Waters)
Column: Aquity OST C18 (2.1×50 mm) (Waters)
Mobile Phases
Buffer A: 200 mM 1,1,1,3,3,3-hexafluoro-2-propanol/8 mM triethylamine
Buffer B: methanol
B concentration gradient: 10-30% (10 min)
Temperature: 50° C.
Flow rate: 0.2 mL/min
Condition 2 (The oligonucleotides with lipid)
Xevo G2 T of System (Waters)
Column: ACQUITY UPLC Protein BEH C4 Column, 300 Å, 1.7 μm, 2.1 mm×100 mm, 1/pkg (Waters)
Mobile Phases
Buffer A: 200 mM 1,1,1,3,3,3-hexafluoro-2-propanol/8 mM triethylamine
Buffer B: methanol
B concentration gradient: 10-95% (10 min)
Temperature: 50° C.
Flow rate: 0.2 mL/min The synthesized oligonucleotides are shown in Tables 1 to 10.

TABLE 1

| ID (SEQ ID) | 5' end modification | Oligonucleotide (5' → 3') | 3' end modification |
|---|---|---|---|
| NA-1 (1) | | U*u*A*a*A*g*u*u*G*a*G*A*G*a*U*c*A*u*C | *dT^dT |
| NA-2 (2) | | *g*A*u*G*a*U*c*u*c*U*c*A*A*C*u*U*u*A*a | *dT^dT^$M_{27-12}$ |
| NA-3 (2) | | g*A*u*G*a*U*c*u*c*U*c*A*A*C*u*U*u*A*a | *dT^dT*$M_{27-12}$ |
| NA-4 (2) | $L_{5-12}$^ | g*A*u*G*a*U*c*u*c*U*c*A*A*C*u*U*u*A*a | *dT^dT |
| NA-5 (2) | $L_{5-12}$* | g*A*u*G*a*U*c*u*c*U*c*A*A*C*u*U*u*A*a | *dT^dT |
| NA-6 (1) | | U*u*A*a*A*g*u*u*G*a*G*A*G*a^U^c^A^u^C | ^dT^dT |
| NA-7 (1) | | U^u*A^a*A^g*u^u*G^a*G^A*G^a*U^c*A^u*C | ^dT^dT |
| NA-8 (2) | | g*A*u*G*a*U*c*u*c*U*c*A*A*C*u*U*u*A*a | *dT^dT |
| NA-9 (1) | -P(O)(OH)$_2$ | U^u*A*a*A*g*u*u*G*a*G*A*G*a*U*c*A*u*C | ^dT^dT |
| NA-10 (2) | | g^A^u^G^a^U*c*u*c*U*c*A*A*C^u^U^u^A^a | ^$M_{13-6}$ |
| NA-11 (2) | | g^A^u^G^a^U*c*u*c*U*c*A*A*C^u^U^u^A^a | ^$M_{13-8}$ |
| NA-12 (2) | | g^A^u^G^a^U*c*u*c*U*c*A*A*C^u^U^u^A^a | ^$M_{13-10}$ |

TABLE 2

| ID (SEQ ID) | 5' end modification | Oligonucleotide (5' → 3') | 3' end modification |
|---|---|---|---|
| NA-13 (2) | | g^A^u^G^a^U*c*u*c*U*c*A*A*C^u^U^u^A^a | ^$M_{13-12}$ |
| NA-14 (2) | | g^A^u^G^a^U*c*u*c*U*c*A*A*C^u^U^u^A^a | ^$M_{13-14}$ |

TABLE 2-continued

| ID (SEQ ID) | 5' end modification | Oligonucleotide (5' → 3') | 3' end modification |
|---|---|---|---|
| NA-15 (2) | | g^A^u^G^a^U*c*u*c*U*c* A*A*C^u^U^u^A^a | ^M$_{13-16}$ |
| NA-16 (2) | | g^A^u^G^a^U*c*u*c*U*c* A*A*C^u^U^u^A^a | ^M$_{13-18}$ |
| NA-17 (2) | | g^A^u^G^a^U*c*u*c*U*c* A*A*C^u^U^u^A^a | ^M$_{13-20}$ |
| NA-18 (2) | | g^A^u^G^a^U*c*u*c*U*c* A*A*C^u^U^u^A^a | ^M$_{13-22}$ |
| NA-19 (2) | | g^A^u^G^a^U*c*u*c*U*c* A*A*C^u^U^u^A^a | ^M$_{33-7-7-7}$ |
| NA-20 (2) | | g^A^u^G^a^U*c*u*c*U*c* A*A*C^u^U^u^A^a | |
| NA-21 (3) | | rG*rU*rA*rG*rG*rA*rG*rU* rA*rG*rU*rG*rA*rA*rA*rG* rG*rC*rA*rG | |
| NA-22 (4) | L$_{NA-22}$* | rG*rG*rC*rC*rU*rU*rU*rC* rA*rC*rU*rA*rC*rU*rC*rC* rU*rA*rC*rG*rA | |
| NA-23 (4) | L$_{NA-23}$* | rG*rG*rC*rC*rU*rU*rU*rC* rA*rC*rU*rA*rC*rU*rC*rC* rU*rA*rC*rG*rA | |

TABLE 3

| ID (SEQ ID) | 5' end modification | Oligonucleotide (5' → 3') | 3' end modification |
|---|---|---|---|
| NA-24 (2) | | g^A^u^G^a^U*c*u*c*U* c*A*A*C^u^U^u^A^a | ^M$_{NA-24}$ |
| NA-25 (2) | | g^A^u^G^a^U*c*u*c*U* c*A*A*C^u^U^u^A^a | ^Bu*Bu*Bu*Bu* Bu*Bu*M$_{42}$ |
| NA-26 (2) | | g^A^u^G^a^U*c*u*c*U* c*A*A*C^u^U^u^A^a | ^Bu*Bu*Bu*Bu* Bu*Bu*M$_{48-8}$ |
| NA-27 (2) | | g^A^u^G^a^U*c*u*c*U* c*A*A*C^u^U^u^A^a | ^Bu*Bu*Bu*Bu* Bu*Bu*M$_{48-12}$ |
| NA-28 (2) | | g^A^u^G^a^U*c*u*c*U* c*A*A*C^u^U^u^A^a | ^Bu*Bu*Bu*Bu* Bu*Bu*M$_{55-5-7}$ |
| NA-29 (2) | | g^A^u^G^a^U*c*u*c*U* c*A*A*C^u^U^u^A^a | ^M$_{124}$^M$_{13}$a$_{-14}$ |
| NA-30 (2) | | g^A^u^G^a^U*c*u*c*U* c*A*A*C^u^U^u^A^a | *dT*dT*dT*dT* dT*dT*M$_{13-14}$ |
| NA-31 (2) | | g^A^u^G^a^U*c*u*c*U* c*A*A*C^u^U^u^A^a | *dT*dT*dT*dT* dT*dT*M$_{124}$* M$_{13}$a$_{-14}$ |
| NA-32 (2) | | g^A^u^G^a^U*c*u*c*U* c*A*A*C^u^U^u^A^a | ^M$_{48-12}$ |
| NA-33 (2) | | g^A^u^G^a^U*c*u*c*U* c*A*A*C^u^U^u^A^a | ^M$_{13}$b-(a6) |
| NA-34 (2) | | g^A^u^G^a^U*c*u*c*U* c*A*A*C^u^U^u^A^a | ^M$_{13}$b-(a10) |
| NA-35 (2) | | g^A^u^G^a^U*c*u*c*U* c*A*A*C^u^U^u^A^a | ^M$_{13}$b-(a18) |

TABLE 4

| ID (SEQ ID) | 5' end modification | Oligonucleotide (5' → 3') | 3' end modification |
|---|---|---|---|
| NA-36 (2) | | g^A^u^G^a^U*c*u*c*U* c*A*A*C^u^U^u^A^a | ^M$_{13b}$-(b) |
| NA-37 (2) | | g^A^u^G^a^U*c*u*c*U* c*A*A*C^u^U^u^A^a | ^M$_{13b}$-(c) |
| NA-38 (2) | | g^A^u^G^a^U*c*u*c*U* c*A*A*C^u^U^u^A^a | ^M$_{13b}$-(d) |
| NA-39 (2) | | g^A^u^G^a^U*c*u*c*U* c*A*A*C^u^U^u^A^a | *A*A*A*A*A* A*M$_{13-14}$ |
| NA-40 (2) | | g^A^u^G^a^U*c*u*c*U* c*A*A*C^u^U^u^A^a | *a*a*a*a*a* a*M$_{13-14}$ |
| NA-41 (13) | | G^a^U*c*u*c*U*c*A*A* C^u^U^u^A^a | *u*u*u*u*u* u*M$_{13-14}$ |
| NA-42 (2) | | g^A^u^G^a^U*c*u*c*U* c*A*A*C^u^U^u^A^a | *dA*dA*dA*dA* dA*dA*M$_{13-14}$ |
| NA-43 (2) | | g^A^u^G^a^U*c*u*c*U* c*A*A*C^u^U^u^A^a | *dG*dG*dG*dG* dG*dG*M$_{13-14}$ |
| NA-44 (2) | | g^A^u^G^a^U*c*u*c*U* c*A*A*C^u^U^u^A^a | *dC*dC*dC*dC* dC*dC*M$_{13-14}$ |
| NA-45 (2) | | g^A^u^G^a^U*c*u*c*U* c*A*A*C^u^U^u^A^a | ^M$_{112-12}$ |
| NA-46 (2) | | g^A^u^G^a^U*c*u*c*U* c*A*A*C^u^U^u^A^a | ^M$_{100-3-18}$ |

TABLE 5

| ID (SEQ ID) | 5' end modification | Oligonucleotide (5' → 3') | 3' end modification |
|---|---|---|---|
| NA-47 (2) | | g^A^u^G^a^U*c*u*c*U* c*A*A*C^u^U^u^A^a | *Ab*Ab*Ab *M$_{13-14}$ |
| NA-48 (2) | | g^A^u^G^a^U*c*u*c*U* c*A*A*C^u^U^u^A^a | *Ab*Ab*Ab*Ab* Ab*Ab*M$_{13-14}$ |
| NA-49 (2) | | g^A^u^G^a^U*c*u*c*U* c*A*A*C^u^U^u^A^a | *Ab*Ab*Ab*Ab* Ab*Ab*Ab*Ab* Ab*M$_{13-14}$ |
| NA-50 (2) | | g^A^u^G^a^U*c*u*c*U* c*A*A*C^u^U^u^A^a | *rA*rA*rA*rA* rA*rA*M$_{13-14}$ |
| NA-51 (2) | | g^A^u^G^a^U*c*u*c*U* c*A*A*C^u^U^u^A^a | ^M$_{13}$b-(e) |
| NA-52 (2) | | g^A^u^G^a^U*c*u*c*U* c*A*A*C^u^U^u^A^a | ^M$_{13}$b-(f) |
| NA-53 (2) | | g^A^u^G^a^U*c*u*c*U* c*A*A*C^u^U^u^A^a | ^M$_{69-1}$ |
| NA-54 (2) | | g^A^u^G^a^U*c*u*c*U* c*A*A*C^u^U^u^A^a | ^M$_{74-3}$ |
| NA-55 (2) | L$_{65-12}$^ | g^A^u^G^a^U*c*u*c*U* c*A*A*C^u^U^u^A^a | |
| NA-56 (2) | | g^A^u^G^a^U*c*u*c*U* c*A*A*C^u^U^u^A^a | ^M$_{13}$b-(g) |
| NA-57 (2) | | g^A^u^G^a^U*c*u*c*U* c*A*A*C^u^U^u^A^a | *dA*dA*dA*dA* M$_{13-14}$ |

TABLE 5-continued

| ID (SEQ ID) | 5' end modification | Oligonucleotide (5' → 3') | 3' end modification |
|---|---|---|---|
| NA-58 (2) | | g^A^u^G^a^U*c*u*c*U*c*A*A*C^u^U^u^A^a | *dA*dA*dA*dA*M$_{13-14}$ |

TABLE 6

| ID (SEQ ID) | 5' end modification | Oligonucleotide (5' → 3') | 3' end modification |
|---|---|---|---|
| NA-59 (2) | | g^A^u^G^a^U*c*u*c*U*c*A*A*C^u^U^u^A^a | *dA*dA*dA*dA*dA*dA*dA*M$_{13-14}$ |
| NA-60 (2) | | g^A^u^G^a^U*c*u*c*U*c*A*A*C^u^U^u^A^a | *dA*dA*dA*dA*dA*dA*dA*dA*M$_{13-14}$ |
| NA-61 (2) | | g^A^u^G^a^U*c*u*c*U*c*A*A*C^u^U^u^A^a | ^M$_{97}$ |
| NA-62 (2) | | g^A^u^G^a^U*c*u*c*U*c*A*A*C^u^U^u^A^a | ^M$_{112-14}$ |
| NA-63 (2) | | g^A^u^G^a^U*c*u*c*U*c*A*A*C^u^U^u^A^a | ^M$_{112-16}$ |
| NA-64 (2) | | g^A^u^G^a^U*c*u*c*U*c*A*A*C^u^U^u^A^a | *dA*dA*dA*dA*dA*dA*M$_{13-14}$ |
| NA-65 (2) | | g^A^u^G^a^U*c*u*c*U*c*A*A*C^u^U^u^A^a | ^M$_{112}$b-(a2) |
| NA-66 (2) | | g^A^u^G^a^U*c*u*c*U*c*A*A*C^u^U^u^A^a | ^M$_{112}$b-(a6) |
| NA-67 (2) | | g^A^u^G^a^U*c*u*c*U*c*A*A*C^u^U^u^A^a | ^M$_{112}$b-(a10) |
| NA-68 (2) | | g^A^u^G^a^U*c*u*c*U*c*A*A*C^u^U^u^A^a | ^M$_{112}$b-(a12) |
| NA-69 (2) | | g^A^u^G^a^U*c*u*c*U*c*A*A*C^u^U^u^A^a | ^M$_{112}$b-(a18) |
| NA-70 (2) | | g^A^u^G^a^U*c*u*c*U*c*A*A*C^u^U^u^A^a | ^M$_{112}$b-(h) |

TABLE 7

| ID (SEQ ID) | 5' end modification | Oligonucleotide (5' → 3') | 3' end modification |
|---|---|---|---|
| NA-71 (2) | | g^A^u^G^a^U*c*u*c*U*c*A*A*C^u^U^u^A^a | ^M$_{112}$b-(b) |
| NA-72 (2) | | g^A^u^G^a^U*c*u*c*U*c*A*A*C^u^U^u^A^a | ^M$_{112}$b-(c) |
| NA-73 (2) | | g^A^u^G^a^U*c*u*c*U*c*A*A*C^u^U^u^A^a | ^M$_{112}$b-(d) |
| NA-74 (2) | | g^A^u^G^a^U*c*u*c*U*c*A*A*C^u^U^u^A^a | ^M$_{112}$b(i) |
| NA-75 (2) | | g^A^u^G^a^U*c*u*c*U*c*A*A*C^u^U^u^A^a | ^M$_{112}$b-(e) |
| NA-76 (2) | | g^A^u^G^a^U*c*u*c*U*c*A*A*C^u^U^u^A^a | ^M$_{112}$b-(g) |

TABLE 7-continued

| ID (SEQ ID) | 5' end modification | Oligonucleotide (5' → 3') | 3' end modification |
|---|---|---|---|
| NA-77 (2) | | g^A^u^G^a^U*c*u*c*U*c*A*A*C^u^U^u^A^a | ^M$_{90}$a |
| NA-78 (2) | | g^A^u^G^a^U*c*u*c*U*c*A*A*C^u^U^u^A^a | ^M$_{90}$b-(j) |
| NA-79 (2) | | g^A^u^G^a^U*c*u*c*U*c*A*A*C^u^U^u^A^a | ^M$_{90}$b-(k) |
| NA-80 (2) | | g^A^u^G^a^U*c*u*c*U*c*A*A*C^u^U^u^A^a | ^M$_{90}$b-(l) |
| NA-81 (2) | | g^A^u^G^a^U*c*u*c*U*c*A*A*C^u^U^u^A^a | ^dA^dA^dA^dA^dA^dA^M$_{112-12}$ |
| NA-82 (2) | | g^A^u^G^a^U*c*u*c*U*c*A*A*C^u^U^u^A^a | ^dA^dA^dA^dA^dA^dA^M$_{13-14}$ |

TABLE 8

| ID (SEQ ID) | 5' end modification | Oligonucleotide (5' → 3') | 3' end modification |
|---|---|---|---|
| NA-83 (2) | | g^A^u^G^a^U*c*u*c*U*c*A*A*C^u^U^u^A^a | *dA*dA*dA^dA^dA^M$_{13-14}$ |
| NA-84 (2) | | g^A^u^G^a^U*c*u*c*U*c*A*A*C^u^U^u^A^a | *dA*dA*dA*dA^dA^M$_{13-14}$ |
| NA-85 (2) | | g^A^u^G^a^U*c*u*c*U*c*A*A*C^u^U^u^A^a | ^dA^dA^dA^dA*dA*M$_{13-14}$ |
| NA-86 (2) | | g^A^u^G^a^U*c*u*c*U*c*A*A*C^u^U^u^A^a | ^dA^dA^dA*dA*dA*M$_{13-14}$ |
| NA-87 (2) | | g^A^u^G^a^U*c*u*c*U*c*A*A*C^u^U^u^A^a | ^dA^dA^dT*dT*dT*dT*M$_{13-14}$ |
| NA-88 (2) | | g^A^u^G^a^U*c*u*c*U*c*A*A*C^u^U^u^A^a | ^dA^dA^dT*dT*dT*dT*dT*dT*M$_{13-14}$ |
| NA-89 (2) | | g^A^u^G^a^U*c*u*c*U*c*A*A*C^u^U^u^A^a | ^M$_{NA-89}$ |
| NA-90 (2) | | g^A^u^G^a^U*c*u*c*U*c*A*A*C^u^U^u^A^a | ^M$_{105-14}$ |

TABLE 9

| ID (SEQ ID) | 5' end modification | Oligonucleotide (5' → 3') | 3' end modification |
|---|---|---|---|
| NA-91 (2) | L$_{65-12}$^dT^dT^dT^dT^dT^dT^ | g^A^u^G^a^U*c*u*c*U*c*A*A*C^u^U^u^A^a | |

TABLE 10

| ID (SEQ ID) | 5' end modification | Oligonucleotide (5' → 3') | 3' end modification |
|---|---|---|---|
| NA-92 (2) | | g^A^u^G^a^U*c*u*c*U*c*A*A*C^u^U^u^A^a | ^dT^dT^dT^dT^dT^dT^M$_{48-12}$ |
| NA-93 (2) | | g^A^u^G^a^U*c*u*c*U*c*A*A*C^u^U^u^A^a | ^M$_{95-3}$-(m) |

TABLE 10-continued

| ID (SEQ ID) | 5' end modification | Oligonucleotide (5' → 3') | 3' end modification |
|---|---|---|---|
| NA-94 (2) | | g^A^u^G^a^U*c*u*c*U*c*A*A*C^u^U^u^A^a | ^M$_{95-3}$-(n) |
| NA-95 (2) | | g^A^u^G^a^U*c*u*c*U*c*A*A*C^u^U^u^A^a | ^M$_{NA-95}$ |
| NA-96 (2) | | g^A^u^G^a^U*c*u*c*U*c*A*A*C^u^U^u^A^a | *dT*dT*dT*dT*dT*dT*M$_{112-12}$ |
| NA-97 (2) | | g^A^u^G^a^U*c*u*c*U*c*A*A*C^u^U^u^A^a | *dT*dT*dT*dT*dT*dT*M$_{112-14}$ |
| NA-98 (2) | | g^A^u^G^a^U*c*u*c*U*c*A*A*C^u^U^u^A^a | ^M$_{95-3}$-(o) |
| NA-99 (2) | | g^A^u^G^a^U*c*u*c*U*c*A*A*C^u^U^u^A^a | ^dT^dT*dT*dT*dT*dT*M$_{NA-95}$ |
| NA-100 (2) | | g^A^u^G^a^U*c*u*c*U*c*A*A*C^u^U^u^A^a | ^M$_{NA-100}$ |
| NA-101 (2) | | g^A^u^G^a^U*c*u*c*U*c*A*A*C^u^U^u^A^a | ^M$_{NA-101}$ |
| NA-102 (2) | | g^A^u^G^a^U*c*u*c*U*c*A*A*C^u^U^u^A^a | ^M$_{NA-102}$ |
| NA-103 (2) | | g^A^u^G^a^U*c*u*c*U*c*A*A*C^u^U^u^A^a | ^M$_{62}$ |
| NA-104 (2) | | g^A^u^G^a^U*c*u*c*U*c*A*A*C^u^U^u^A^a | ^M$_{120}$ |
| NA-105 (2) | | g^A^u^G^a^U*c*u*c*U*c*A*A*C^u^U^u^A^a | ^M$_{120-6}$ |
| NA-106 (2) | | g^A^u^G^a^U*c*u*c*U*c*A*A*C^u^U^u^A^a | ^M$_{120-12}$ |

In Tables 1 to 10, n (small letter) is 2'-F-RNA, N (capital letter) is 2'-OMe-RNA, rN is RNA, and dN is DNA. ^ is —P(S)OH—, and * is —P(O)OH—.

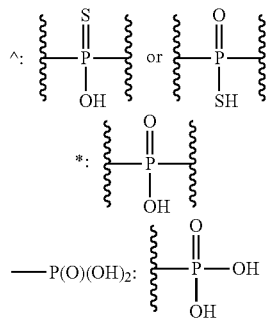

Ab (Abasic) is the following group.

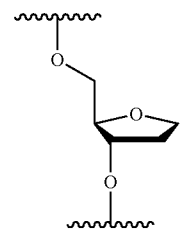

Bu is the following group.

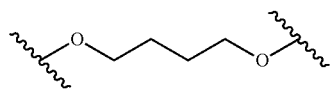 [SMILES: *OCCCCO*]

L means a compound introduced at the 5' end of an oligonucleotide (optionally comprising an oligonucleotide linker), and each compound covalently binds with a substituted or unsubstituted methylene of the 5' end of an oligonucleotide. M means a compound introduced at the 3'-end of an oligonucleotide (optionally comprising an oligonucleotide linker), and each compound covalently binds with a sugar of the 3'-end of an oligonucleotide.

Specifically, $L_{x-n'}$ binds at the 5'-end of an oligonucleotide, which may also include an oligonucleotide linker, as below. In the following formula, OL5' means that the terminal bond of $L_{x-n'}$ binds at 5'-end of an oligonucleotide having suppressing activity of the target gene expression or an oligonucleotide linker via "^(—P(S)OH—)" or "*(—P(O)OH—)" as described in the above tables.

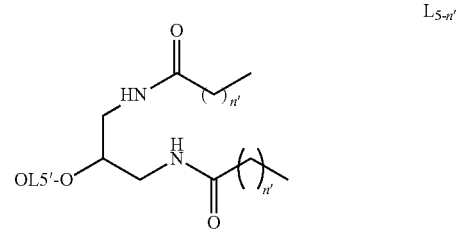

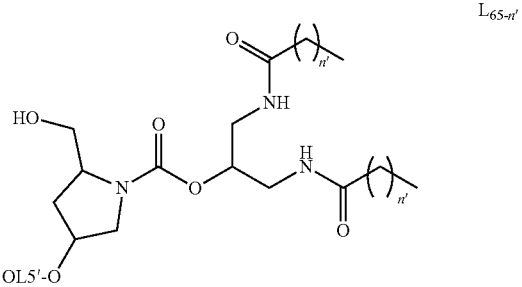

wherein n' is an integer of 5 to 29.

$L_{5-n'}$ is a group derived from Compound 5-n' which is synthesized in the above A), $L_{65-n'}$ is a group derived from Compound 65-n'.

$M_{x-n'}$ binds at 3'-end of an oligonucleotide, which may also include an oligonucleotide linker, as below. In the following formula, OL3' means that the terminal bond of $M_{x-n'}$ binds at 3'-end of an oligonucleotide having suppressing activity of the target gene expression or an oligonucleotide linker via "^(—P(S)OH—)" or "*(—P(O)OH—)" as described in the above tables.

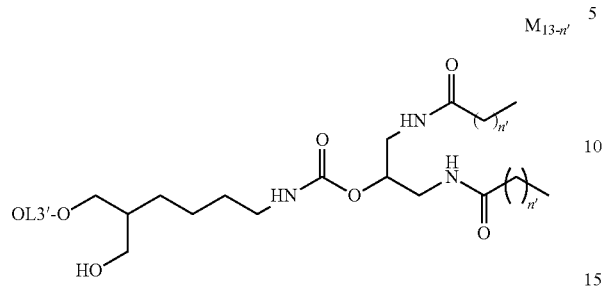

M$_{13-n'}$ wherein n' is an integer of 5 to 29.

M$_{13-n'}$ is a group derived from Compound 13-n' which is synthesized in the above A).

M$_{13a-n'}$ is a group which binds to a group except for an oligonucleotide. For example, it means that M$_{13-n'}$ binds to M$_{124}$ which is a group derived from Compound 124 which is synthesized in the above A).

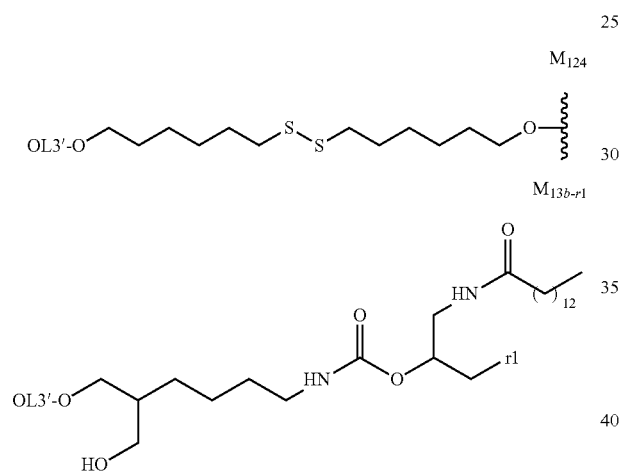

M$_{124}$

M$_{13b-r1}$ wherein r1 is a group selected from the following Substituent (an") to (g).

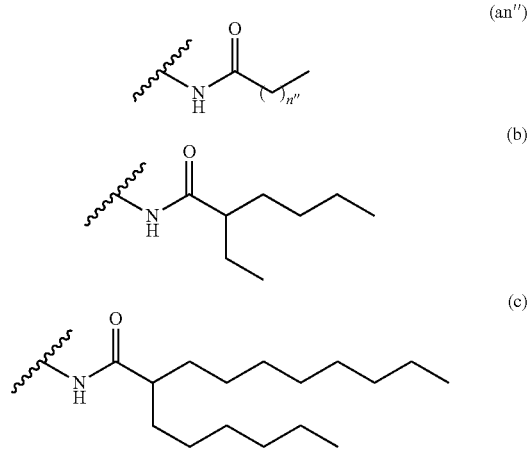

(an")

(b)

(c)

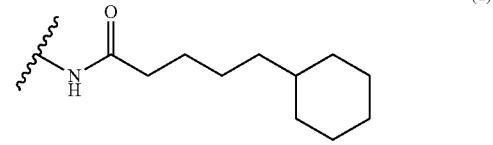

(d)

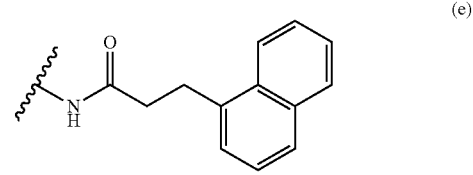

(e)

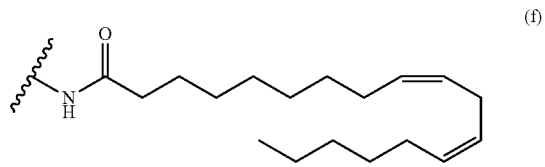

(f)

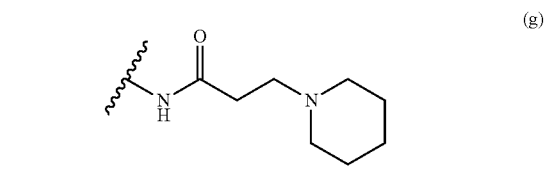

(g)

wherein n" is an integer of 2 to 29.

M$_{13b-r1}$ is a group synthesized in a similar method as Compound 13-n' in the above A) and derived from Compound 75-n" (Substituent (an")), Compound 77 (Substituent (b)), Compound 78 (Substituent (c)), Compound 80 (Substituent (d)), Compound 83 (Substituent (e)), Compound 82 (Substituent (f)) or Compound 86 (Substituent (g)).

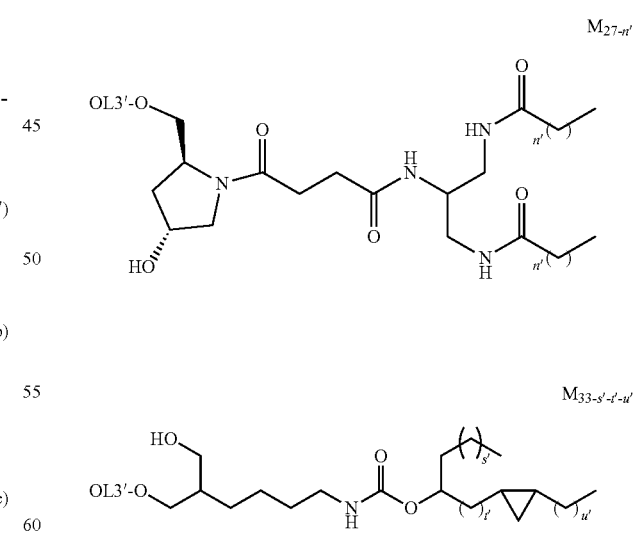

M$_{27-n'}$

M$_{33-s'-t'-u'}$ wherein n' is an integer of 5 to 29, and s', t' and u' are each independently an integer of 3 to 20.

M$_{27-n'}$ is a group derived from Compound 27-n' which is synthesized in the above A), and M$_{33-s'-t'-u'}$ is a group derived from Compound 33-s'-t'-u'.

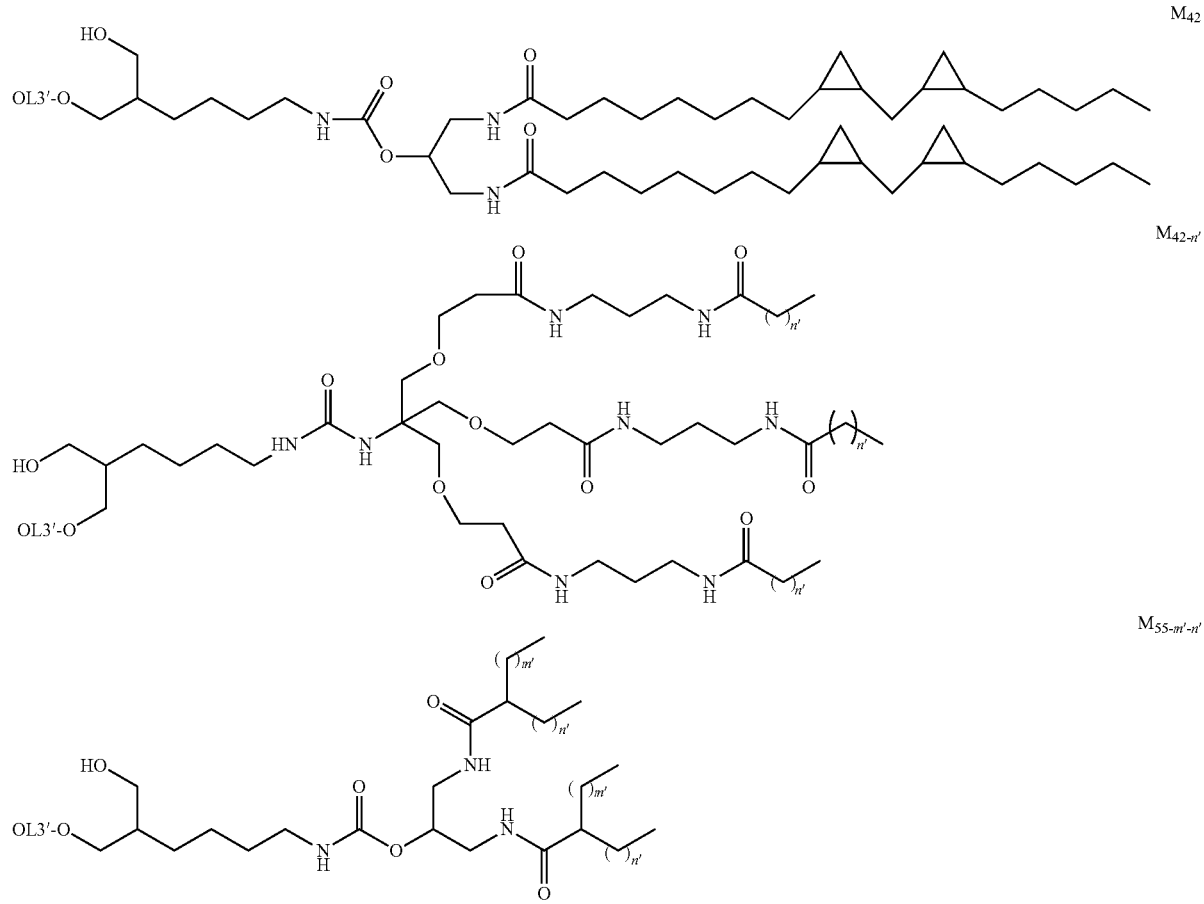

wherein m' and n' are each independently an integer of 5 to 29.

$M_{42}$ is a group derived from Compound 42 which is synthesized in the above A), $M_{48-n'}$ is a group derived from Compound 48-n', and $M_{55-m'-n'}$ is a group derived from Compound 55-m'-n'.

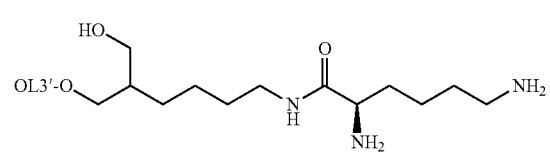

-continued

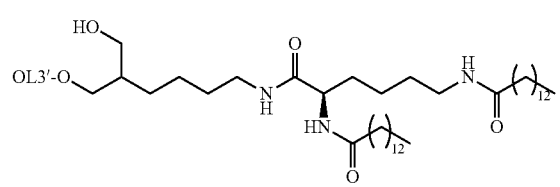

$M_{NA-102}$ is a group derived from the following NA-24 and Compound 103 according to the above 4) of C). $M_{NA-89}$ is a group derived from the NA-102 and Compound 75-12 according to the above 4) of C).

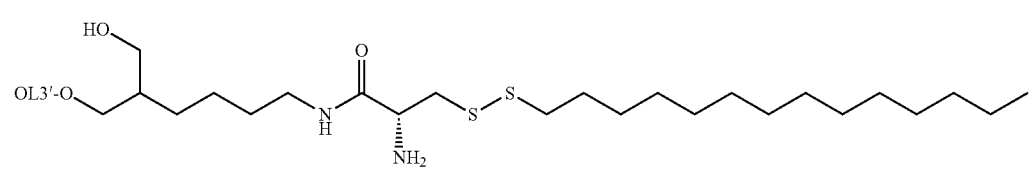

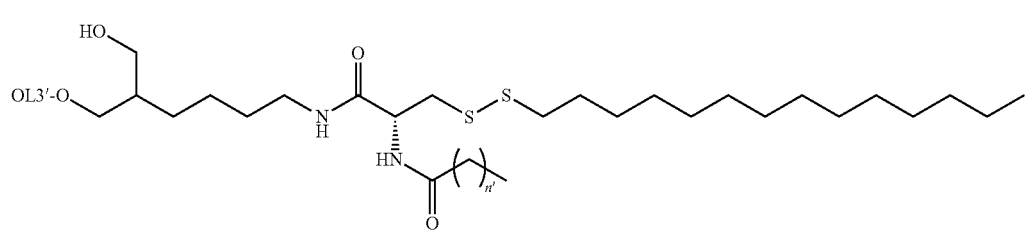

$M_{120-n'}$ wherein n' is an integer of 5 to 29.

$M_{120}$ is a group derived from Compound 120 which is synthesized in the above A), and $M_{120-n'}$ is a group derived from NA-104 and Compound 75-n" according to the above 4) of C).

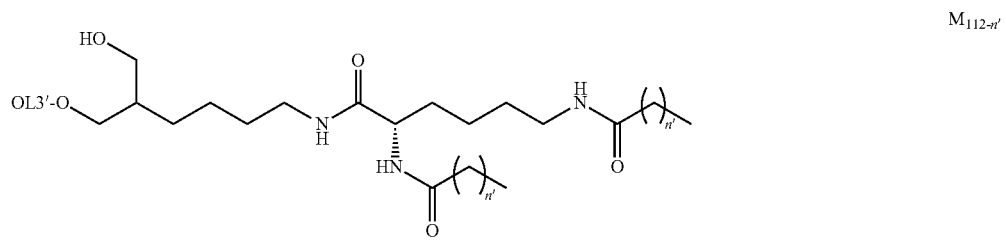

$M_{112-n'}$

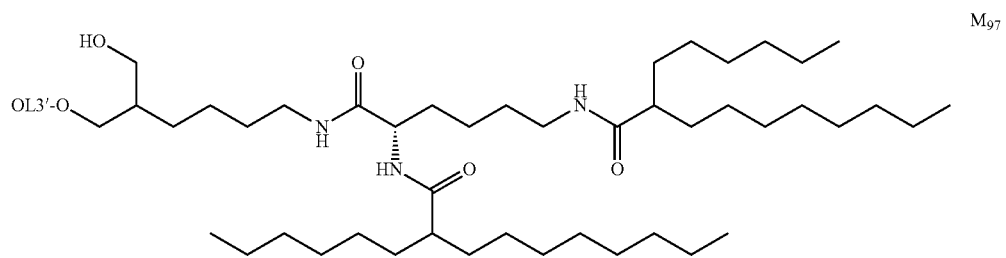

$M_{97}$ wherein n' is integer of 5 to 29.

$M_{112-n'}$ is a group which is synthesized and derived in a similar method as Compound 112 which is synthesized in the above A), and $M_9$ 7 is a group derived from Compound 97.

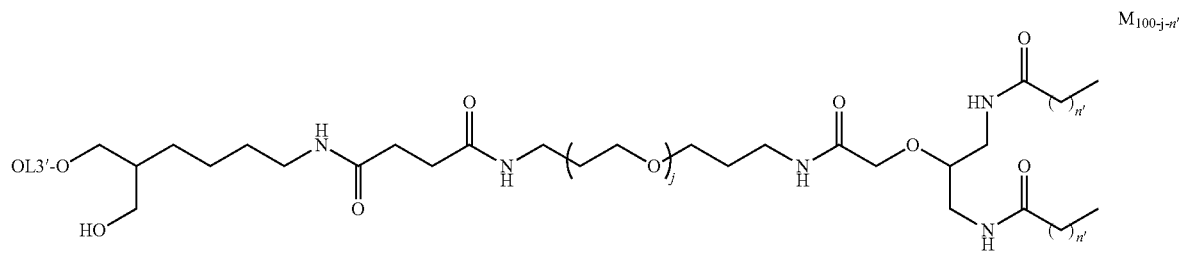

$M_{100-j-n'}$ wherein j is an integer of 1 to 3, and n' is an integer of 5 to 29.

M₁₀₀₋ⱼ₋ₙ' is a group which is synthesized and derived in a similar method as Compound 100-j-n' which is synthesized in the above A).

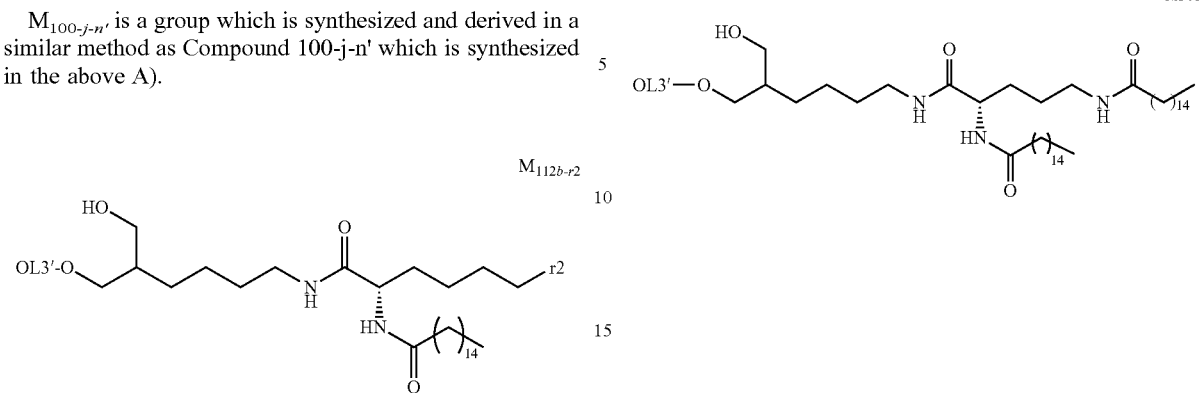

wherein r2 is a group selected from Substituent (an″) to (e), (g) of r1 and the following (h) and (i).

M₁₁₂ᵦ₋ᵣ₂ is a group which is synthesized in a similar method as Compound 112 in the above A) and derived from Compound 75-n″ (Substituent (an″)), Compound 77 (Substituent (b)), Compound 78 (Substituent (c)), Compound 80 (Substituent (d)), Compound 83 (Substituent (e)), Compound 86 (Substituent (g)), Compound 76 (Substituent (h)) or Compound 81 (Substituent (i)).

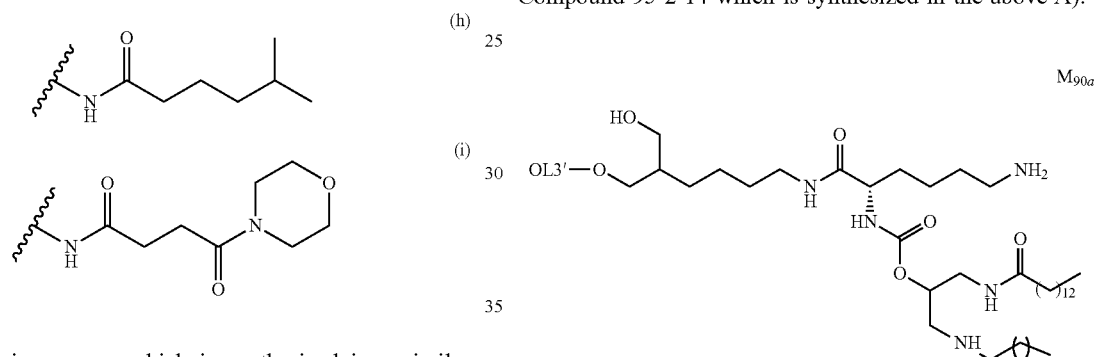

wherein k is an integer of 0 to 4, and n' is an integer of 1 to 4.

M₆₉₋ₙ' is a group derived from Compound 69-n' which is synthesized in the above A), M₇₄₋ₖ is a group derived from Compound 74-k-14, and M_{NA-95} is a group derived from Compound 95-2-14 which is synthesized in the above A).

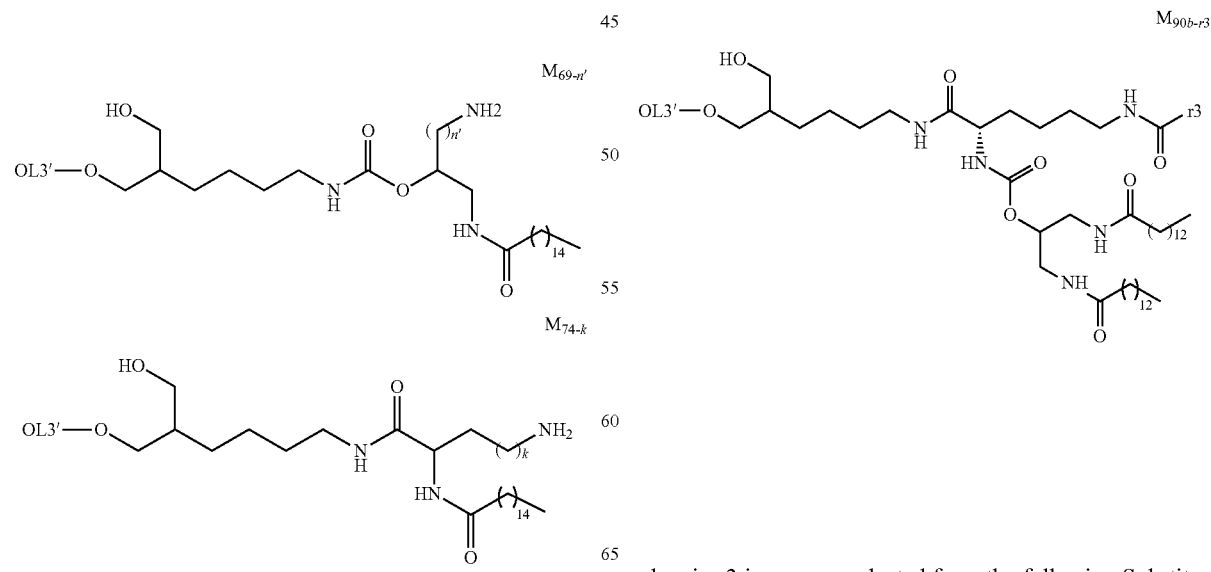

wherein r3 is a group selected from the following Substituent (j) to (l).

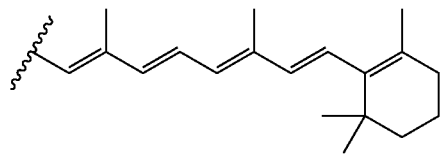

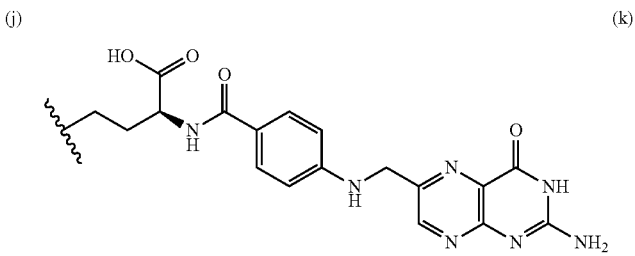

M$_{90a}$ and M$_{90b\text{-}r3}$ are groups derived from Compound 90-k-n' which is synthesized in the above A) and Compound 121 (Substituent (j)), Compound 122 (Substituent (k)) or Compound 123 (Substituent (l)) according to the above 6) of C).

wherein k is an integer of 0 to 4, and r4 is a group selected from the following Substituent (m) to (o).

wherein n' is an integer of 5 to 29.

M$_{105\text{-}n'}$ is a group derived from Compound 105-n' which is synthesized in the above A).

M$_{95\text{-}r4}$ is a group derived from Compound 95-k-14 which is synthesized in the above A) and Compound 88 (Substituent (m)), Compound 3-14 (Substituent (n)) or hexyl isocyanate (Substituent (o)).

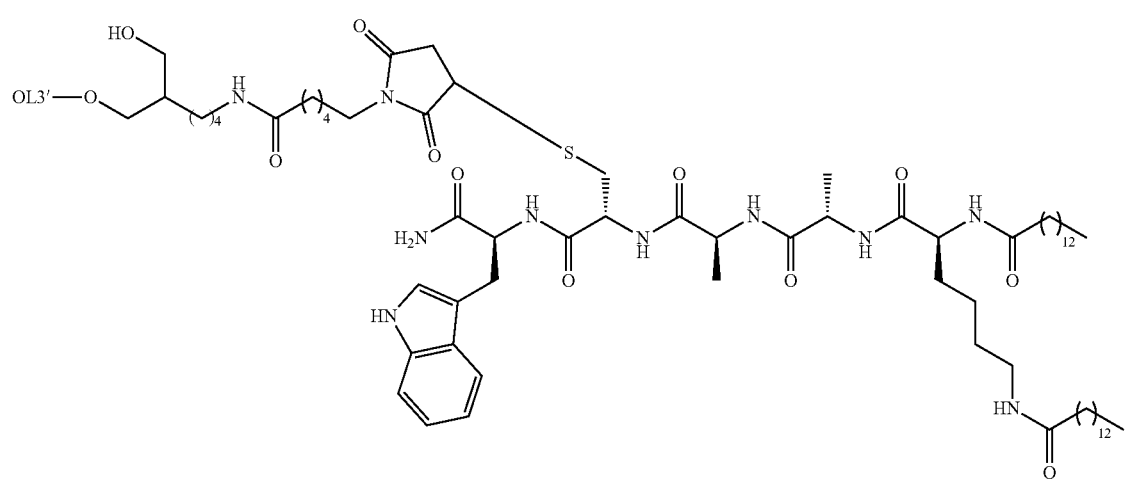
$M_{NA\text{-}100}$
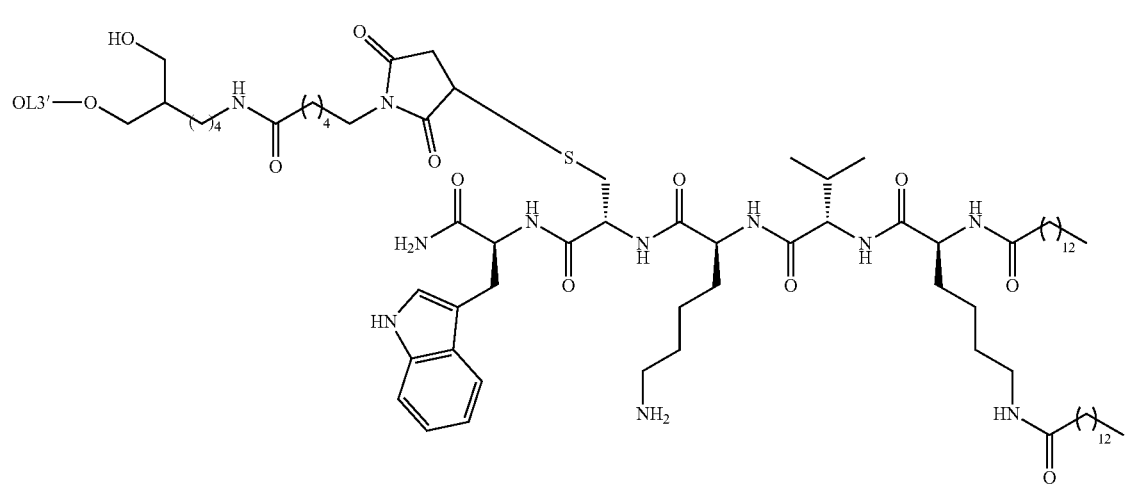
$M_{NA\text{-}101}$
$M_{NA\text{-}100}$ is a group derived from Compound 101 according to the above 5) of C), and $M_{NA\text{-}101}$ is a group derived from Compound 102 according to the above 5) of C).
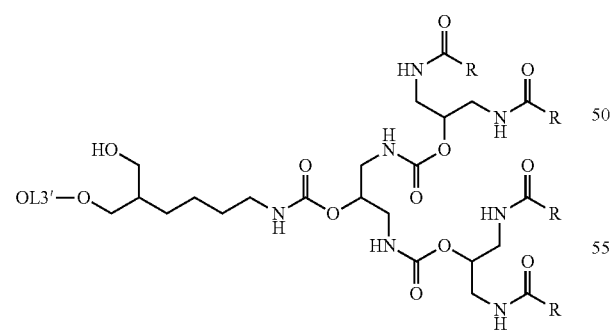
$M_{62}$
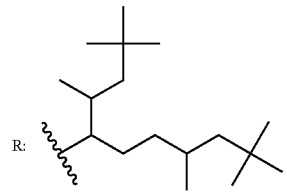
R:

$M_{62}$ is a group derived from Compound 62 which is synthesized in the above A).

Substituents for NA-22 to 24 in the comparative examples binds to an oligonucleotide as below.

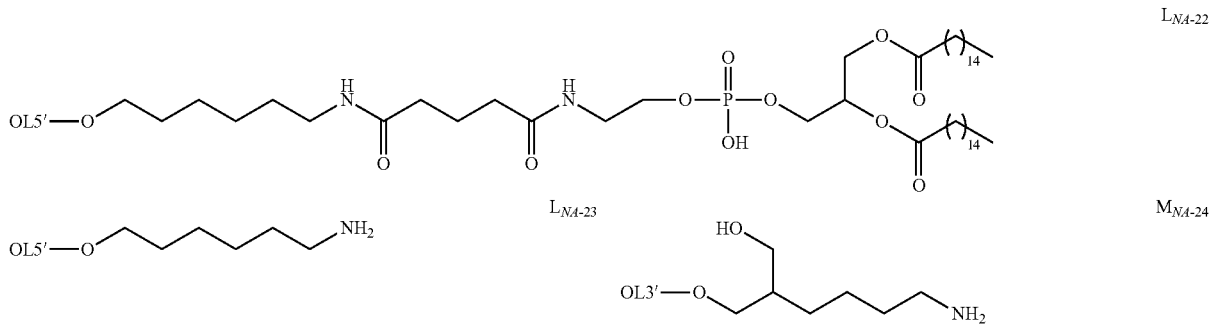

A substituent for $L_{NA-22}$ was synthesized with reference to the description of Patent Document 8.

A substituent for $M_{NA-24}$ was purchased from Link Technology Co., Ltd. Nucleic acid derivatives comprising an amino linker at 3'-end were synthesized by synthesizing an oligonucleotide in a similar method to the above B) with the resin for nucleic acid resin (3'-amino CPG).

The results of purity analysis of the synthesized single-stranded oligonucleotide are shown in Tables 11 to 13.

TABLE 11

| Oligonucleotide | Theoretical Mw [M − H]⁻ | Found Mw [M − H]⁻ |
|---|---|---|
| NA-1 | 6853.31 | 6854 |
| NA-2 | 7525.28 | 7527 |
| NA-3 | 7509.21 | 7510 |
| NA-4 | 7328.07 | 7328 |
| NA-5 | 7312.00 | 7312 |
| NA-8 | 6738.18 | 6739 |
| NA-9 | 6981.50 | 6983 |
| NA-10 | 6868.18 | 6869 |
| NA-11 | 6924.29 | 6925 |
| NA-12 | 6980.40 | 6982 |
| NA-13 | 7036.50 | 7037 |
| NA-14 | 7092.61 | 7094 |
| NA-15 | 7148.72 | 7150 |
| NA-16 | 7204.83 | 7206 |
| NA-17 | 7260.94 | 7262 |
| NA-18 | 7317.04 | 7318 |
| NA-19 | 6934.41 | 6935 |
| NA-20 | 6274.41 | 6276 |
| NA-22 | 7537.19 | 7537 |
| NA-24 | 6499.65 | 6501 |

TABLE 12

| Oligonucleotide | Theoretical Mw [M − H]⁻ | Found Mw [M − H]⁻ |
|---|---|---|
| NA-25 | 8108.26 | 8108 |
| NA-26 | 8405.57 | 8405 |
| NA-27 | 8573.90 | 8575 |
| NA-28 | 8004.11 | 8002 |
| NA-29 | 7437.05 | 7437 |
| NA-30 | 8901.67 | 8902 |
| NA-31 | 9230.09 | 9230 |
| NA-32 | 7663.40 | 7663 |
| NA-33 | 6980.40 | 6981 |
| NA-34 | 7036.50 | 7037 |
| NA-35 | 7148.72 | 7149 |

TABLE 12-continued

| Oligonucleotide | Theoretical Mw [M − H]⁻ | Found Mw [M − H]⁻ |
|---|---|---|
| NA-36 | 6980.40 | 6981 |
| NA-37 | 7092.61 | 7093 |
| NA-38 | 7020.46 | 7021 |
| NA-39 | 9135.92 | 9137 |
| NA-40 | 9063.70 | 9065 |
| NA-41 | 7878.67 | 7879 |
| NA-42 | 8955.76 | 8955 |
| NA-43 | 9051.76 | 9052 |
| NA-44 | 8811.61 | 8812 |
| NA-45 | 7048.51 | 7049 |
| NA-46 | 7507.15 | 7508 |
| NA-47 | 7616.80 | 7618 |
| NA-48 | 8157.10 | 8157 |
| NA-49 | 8697.40 | 8698 |
| NA-50 | 9051.80 | 9052 |
| NA-51 | 7036.42 | 7039 |
| NA-52 | 7116.63 | 7117 |
| NA-53 | 6854.20 | 6855 |
| NA-54 | 6866.25 | 6867 |
| NA-55 | 7005.41 | 7007 |
| NA-56 | 6993.40 | 6996 |
| NA-57 | 8329.34 | 8330 |
| NA-58 | 8642.55 | 8643 |
| NA-59 | 9268.97 | 9268 |
| NA-60 | 9582.18 | 9582 |
| NA-61 | 7104.62 | 7105 |
| NA-62 | 7104.62 | 7105 |
| NA-63 | 7160.73 | 7163 |
| NA-64 | 8911.71 | 8912 |
| NA-65 | 6936.34 | 6938 |
| NA-66 | 6992.45 | 6994 |
| NA-67 | 7048.56 | 7050 |
| NA-68 | 7076.61 | 7078 |
| NA-69 | 7160.78 | 7162 |
| NA-70 | 6978.42 | 6980 |
| NA-71 | 6992.45 | 6994 |
| NA-72 | 7104.67 | 7106 |
| NA-73 | 7032.52 | 7034 |
| NA-74 | 7035.43 | 7037 |
| NA-75 | 7048.47 | 7051 |
| NA-76 | 7005.45 | 7007 |
| NA-77 | 7164.70 | 7166 |
| NA-78 | 7447.10 | 7448 |
| NA-79 | 7588.10 | 7590 |
| NA-80 | 8269.90 | 8272 |
| NA-81 | 9024.10 | 9026 |
| NA-82 | 9068.20 | 9070 |
| NA-83 | 9020.00 | 9021 |

TABLE 12-continued

| Oligonucleotide | Theoretical Mw [M − H]⁻ | Found Mw [M − H]⁻ |
|---|---|---|
| NA-84 | 8987.90 | 8989 |
| NA-85 | 9036.10 | 9037 |
| NA-86 | 8987.90 | 8989 |

TABLE 13

| Oligonucleotide | Theoretical Mw [M − H]⁻ | Found Mw [M − H]⁻ |
|---|---|---|
| NA-87 | 8969.90 | 8971 |
| NA-88 | 9596.30 | 9598 |
| NA-89 | 7048.50 | 7050 |
| NA-90 | 7140.66 | 7142 |
| NA-91 | 8927.04 | 8930 |
| NA-92 | 9584.04 | 9585 |
| NA-93 | 7322.96 | 7325 |
| NA-94 | 7403.09 | 7406 |
| NA-95 | 7090.60 | 7093 |
| NA-96 | 8857.60 | 8860 |
| NA-97 | 8913.70 | 8916 |
| NA-98 | 6993.44 | 6995 |
| NA-99 | 8931.82 | 8934 |
| NA-100 | 7689.20 | 7692 |
| NA-101 | 7774.40 | 7777 |
| NA-102 | 6627.80 | 6630 |
| NA-103 | 8825.39 | 8825 |
| NA-104 | 6831.19 | 6833 |
| NA-105 | 6957.39 | 6959 |
| NA-106 | 7041.55 | 7043 |

H) Preparation of the Double-Stranded Oligonucleotide

After mixing the equimolecular amount of 100μM solution of each oligonucleotide, the solution was heated at 75° C. for 5 minutes, and naturally cooled to room temperature to obtain the double-stranded nucleic acids. Conformation of the double-stranded formation was carried out with size exclusion chromatography.

Column: YMC-PAC Diol-120 (4.6×300 mm) (YMC co., ltd.)

Mobile phases: 40% acetonitrile in 1×PBS solution

Flow rate: 0.5 mL/min

Temperature: room temperature

The synthesized oligonucleotides (siRNAs) are shown in Tables 14 to 15.

TABLE 14

| siRNA | ID |
|---|---|
| siRNA-1 | NA-1 |
|  | NA-8 |
| siRNA-2 | NA-1 |
|  | NA-2 |
| siRNA-3 | NA-1 |
|  | NA-3 |
| siRNA-4 | NA-1 |
|  | NA-4 |
| siRNA-5 | NA-1 |
|  | NA-5 |
| siRNA-6 | NA-6 |
|  | NA-2 |
| siRNA-7 | NA-7 |
|  | NA-2 |
| siRNA-8 | NA-9 |
|  | NA-10 |
| siRNA-9 | NA-9 |
|  | NA-11 |
| siRNA-10 | NA-9 |
|  | NA-12 |
| siRNA-11 | NA-9 |
|  | NA-13 |
| siRNA-12 | NA-9 |
|  | NA-14 |
| siRNA-13 | NA-9 |
|  | NA-15 |
| siRNA-14 | NA-9 |
|  | NA-16 |
| siRNA-15 | NA-9 |
|  | NA-17 |
| siRNA-16 | NA-9 |
|  | NA-18 |
| siRNA-17 | NA-9 |
|  | NA-19 |
| siRNA-18 | NA-9 |
|  | NA-20 |
| siRNA-19 | NA-21 |
|  | NA-22 |
| siRNA-20 | NA-21 |
|  | NA-23 |
| siRNA-21 | NA-9 |
|  | NA-24 |
| siRNA-22 | NA-9 |
|  | NA-25 |
| siRNA-23 | NA-9 |
|  | NA-26 |
| siRNA-24 | NA-9 |
|  | NA-27 |
| siRNA-25 | NA-9 |
|  | NA-28 |
| siRNA-26 | NA-9 |
|  | NA-29 |
| siRNA-27 | NA-9 |
|  | NA-30 |
| siRNA-28 | NA-9 |
|  | NA-31 |
| siRNA-29 | NA-9 |
|  | NA-32 |
| siRNA-30 | NA-9 |
|  | NA-33 |
| siRNA-31 | NA-9 |
|  | NA-34 |
| siRNA-32 | NA-9 |
|  | NA-35 |
| siRNA-33 | NA-9 |
|  | NA-36 |
| siRNA-34 | NA-9 |
|  | NA-37 |
| siRNA-35 | NA-9 |
|  | NA-38 |
| siRNA-36 | NA-9 |
|  | NA-39 |
| siRNA-37 | NA-9 |
|  | NA-40 |
| siRNA-38 | NA-9 |
|  | NA-41 |
| siRNA-39 | NA-9 |
|  | NA-42 |
| siRNA-40 | NA-9 |
|  | NA-43 |
| siRNA-41 | NA-9 |
|  | NA-44 |
| siRNA-42 | NA-9 |
|  | NA-45 |
| siRNA-43 | NA-9 |
|  | NA-46 |
| siRNA-44 | NA-9 |
|  | NA-47 |
| siRNA-45 | NA-9 |
|  | NA-48 |
| siRNA-46 | NA-9 |
|  | NA-49 |
| siRNA-47 | NA-9 |
|  | NA-50 |
| siRNA-48 | NA-9 |
|  | NA-51 |

TABLE 14-continued

| siRNA | ID |
|---|---|
| siRNA-49 | NA-9 |
| | NA-52 |
| siRNA-50 | NA-9 |
| | NA-53 |
| siRNA-51 | NA-9 |
| | NA-54 |
| siRNA-52 | NA-9 |
| | NA-55 |
| siRNA-53 | NA-9 |
| | NA-56 |
| siRNA-54 | NA-9 |
| | NA-57 |
| siRNA-55 | NA-9 |
| | NA-58 |
| siRNA-56 | NA-9 |
| | NA-59 |
| siRNA-57 | NA-9 |
| | NA-60 |
| siRNA-58 | NA-9 |
| | NA-61 |
| siRNA-59 | NA-9 |
| | NA-62 |
| siRNA-60 | NA-9 |
| | NA-63 | siRNA-1, 18, 19 and 20 are the comparative examples.

TABLE 15

| siRNA | ID |
|---|---|
| siRNA-61 | NA-9 |
| | NA-64 |
| siRNA-62 | NA-9 |
| | NA-65 |
| siRNA-63 | NA-9 |
| | NA66 |
| siRNA-64 | NA-9 |
| | NA-67 |
| siRNA-65 | NA-9 |
| | NA-68 |
| siRNA-66 | NA-9 |
| | NA-69 |
| siRNA-67 | NA-9 |
| | NA-70 |
| siRNA-68 | NA-9 |
| | NA-71 |
| siRNA-69 | NA-9 |
| | NA-72 |
| siRNA-70 | NA-9 |
| | NA-73 |
| siRNA-71 | NA-9 |
| | NA-74 |
| siRNA-72 | NA-9 |
| | NA-75 |
| siRNA-73 | NA-9 |
| | NA-76 |
| siRNA-74 | NA-9 |
| | NA-77 |
| siRNA-75 | NA-9 |
| | NA-78 |
| siRNA-76 | NA-9 |
| | NA-79 |
| siRNA-77 | NA-9 |
| | NA-80 |
| siRNA-78 | NA-9 |
| | NA-81 |
| siRNA-79 | NA-9 |
| | NA-82 |
| siRNA-80 | NA-9 |
| | NA-83 |
| siRNA-81 | NA-9 |
| | NA-84 |
| siRNA-82 | NA-9 |
| | NA-85 |

TABLE 15-continued

| siRNA | ID |
|---|---|
| siRNA-83 | NA-9 |
| | NA-86 |
| siRNA-84 | NA-9 |
| | NA-87 |
| siRNA-85 | NA-9 |
| | NA-88 |
| siRNA-86 | NA-9 |
| | NA-89 |
| siRNA-87 | NA-9 |
| | NA-90 |
| siRNA-88 | NA-9 |
| | NA-91 |
| siRNA-89 | NA-9 |
| | NA-92 |
| siRNA-90 | NA-9 |
| | NA-93 |
| siRNA-91 | NA-9 |
| | NA-94 |
| siRNA-92 | NA-9 |
| | NA-95 |
| siRNA-93 | NA-9 |
| | NA-96 |
| siRNA-94 | NA-9 |
| | NA-97 |
| siRNA-95 | NA-9 |
| | NA-98 |
| siRNA-96 | NA-9 |
| | NA-99 |
| siRNA-97 | NA-9 |
| | NA-100 |
| siRNA-98 | NA-9 |
| | NA-101 |
| siRNA-99 | NA-9 |
| | NA-105 |
| siRNA-100 | NA-9 |
| | NA-106 |
| siRNA-101 | NA-9 |
| | NA-103 | siRNA-101 is a comparative example.

Example 2: Evaluation of siRNAs by Free Uptake (Transfection without Gene Transfection Reagents)

Experiment 1

HeLa cells, human cervical cancer cell line, were cultured in DMEM Low Glucose (Sigma)+10% Fetal Bovine Serum (FBS)+Penicillin (100 units/mL)+Streptomycin (100 ug/mL). The cells were maintained at 37° C., 95 to 98% humidity and 5% $CO_2$. In all cells for this experiment, siRNAs were transfected into cells without any gene transfection reagent. To a culture supernatant of the HeLa cells, the complex of the present invention comprising siRNA as a nucleic acid medicine or siRNA without a lipid (siRNA-1) as a comparative example was added to be at final concentration of 1 µM. After 72 hours, the cells were collected with CellAmp RNA Prep Kit (Takara) and quantitative PCR was performed with One Step SYBR PrimeScript PLUS RT-PCR Kit (Takara). GAPDH was used as an endogenous control. The primer sequences for measuring the level of human HPRT1 expression are

```
Fw primer:
                               (SEQ ID NO: 5)
CTACCCTCTGGTAGATTGTCG;
and Rv primer:
                               (SEQ ID NO: 6)
TCGAGAGCTTCAGACTCGTCTA.
```

The primer sequences for measuring the level of human GAPDH expression are

```
Fw primer:
                                    (SEQ ID NO: 7)
GCACCGTCAAGGCTGAGAAC;
and Rv primer:
                                    (SEQ ID NO: 8)
TGGTGAAGACGCCAGTGGA.
```

The results are shown in Table 16. In the table, the ratios of the amount of Hprt1 mRNA normalized with Gapdh compared to untreated cells were shown as the knockdown efficiency.

TABLE 16

| siRNA | % mRNA |
|---|---|
| siRNA-1 | 96 |
| siRNA-2 | 10 |
| siRNA-3 | 7 |
| siRNA-4 | 28 |
| siRNA-5 | 30 |

Experiment 2

Hepa1c1c7 cells, mouse hepatoma cell line, were cultured in MEM Alpha (Thermo Fisher Scientific)+10% Fetal Bovine Serum (FBS)+Penicillin (100 units/mL)+Streptomycin (100 ug/mL). The cells were maintained at 37° C., 95 to 98% humidity and 5% $CO_2$. In all cells for this experiment, siRNAs were transfected into cells without any gene transfection reagent. To a culture supernatant of the Hepa1c1c7 cells, the complex of the present invention comprising siRNA as a nucleic acid medicine was added to be at final concentration of 2 μM. After 72 hours, the cells were collected with CellAmp RNA Prep Kit (Takara) and quantitative PCR was performed with One Step SYBR PrimeScript PLUS RT-PCR Kit (Takara). Gapdh was used as an endogenous control.

The primer sequences for measuring the level of mouse Hprt1 expression are

```
Fw primer:
                                    (SEQ ID NO: 9)
TTGTTGTTGGATATGCCCTTGACTA;
and Rv primer:
                                    (SEQ ID NO: 10)
AGGCAGATGGCCACAGGACTA.
```

The primer sequences for measuring the level of mouse Gapdh expression are

```
Fw primer:
                                    (SEQ ID NO: 11)
TGTGTCCGTCGTGGATCTGA;
and Rv primer:
                                    (SEQ ID NO: 12)
TTGCTGTTGAAGTCGCAGGAG.
```

The results are shown in Table 17. In the table, the ratios of the amount of Hprt1 mRNA normalized with Gapdh compared to untreated cells were shown as the knockdown efficiency.

TABLE 17

| siRNA | % mRNA |
|---|---|
| siRNA-22 | 45 |
| siRNA-23 | 45 |
| siRNA-24 | 20 |
| siRNA-27 | 11 |
| siRNA-28 | 36 |
| siRNA-29 | 25 |
| siRNA-31 | 35 |
| siRNA-32 | 45 |
| siRNA-36 | 14 |
| siRNA-37 | 16 |
| siRNA-38 | 18 |
| siRNA-39 | 13 |
| siRNA-40 | 33 |
| siRNA-41 | 16 |
| siRNA-42 | 18 |
| siRNA-44 | 26 |
| siRNA-45 | 17 |
| siRNA-46 | 18 |
| siRNA-47 | 19 |
| siRNA-49 | 37 |
| siRNA-50 | 36 |
| siRNA-51 | 29 |
| siRNA-52 | 27 |
| siRNA-54 | 16 |
| siRNA-55 | 16 |
| siRNA-56 | 18 |
| siRNA-57 | 17 |
| siRNA-59 | 19 |
| siRNA-60 | 44 |
| siRNA-61 | 16 |
| siRNA-62 | 37 |
| siRNA-63 | 31 |
| siRNA-64 | 20 |
| siRNA-65 | 21 |
| siRNA-66 | 42 |
| siRNA-67 | 44 |
| siRNA-68 | 49 |
| siRNA-69 | 51 |
| siRNA-70 | 32 |
| siRNA-71 | 41 |
| siRNA-72 | 54 |
| siRNA-73 | 50 |
| siRNA-74 | 20 |
| siRNA-75 | 49 |
| siRNA-76 | 39 |
| siRNA-77 | 23 |
| siRNA-78 | 29 |
| siRNA-79 | 30 |
| siRNA-80 | 22 |
| siRNA-81 | 21 |
| siRNA-82 | 28 |
| siRNA-83 | 23 |
| siRNA-84 | 19 |
| siRNA-85 | 21 |
| siRNA-86 | 25 |
| siRNA-89 | 32 |
| siRNA-92 | 21 |
| siRNA-93 | 20 |
| siRNA-94 | 20 |
| siRNA-95 | 35 |
| siRNA-96 | 25 |
| siRNA-97 | 27 |
| siRNA-98 | 38 |
| siRNA-99 | 36 |
| siRNA-100 | 19 |
| siRNA-101 | 104 |

As the above, both the complexes of the present invention whose lipid was bound at the 3'-end of the second strand (siRNA-2, siRNA-3, etc.) and the complexes of the present invention whose lipid was bound at the 5'-end of the second strand (siRNA-4, siRNA-5, etc.) showed higher knockdown activities against HPRT1 compared to the comparative example without lipid (siRNA-1) or the comparative example with the eight-branched lipid (siRNA-101). It is thought that the complexes of the present invention with high knockdown activity without any gene transfection reagent are capable of fully exerting the effects of the comprised nucleic acid medicines and are very useful in drug discovery.

Experiment 3

As Experiment 1, to a culture supernatant of the HeLa cells, the complex of the present invention (siRNA-2, siRNA-6 or siRNA-7) or siRNA without a lipid (siRNA-1) as a comparative example was added to be at final concentration of 0.5 μM. After 72 hours, the cells were collected, and quantitative PCR was performed. GAPDH was used as an endogenous control. The primer sequences for measuring the level of HPRT1 and GAPDH are the same as Experiment 1. The results are shown in Table 18.

TABLE 18

| siRNA | % mRNA |
|---|---|
| siRNA-1 | 67 |
| siRNA-2 | 21 |
| siRNA-6 | 10 |
| siRNA-7 | 16 |

As a result, the complexes of the present invention whose comprised nucleic acid medicine were modified (the oligonucleotide of the first strand comprises phosphorothioates) (siRNA-6 and siRNA-7) also showed higher knockdown activities against HPRT1.

Example 3: Evaluation of In Vivo Activity (Animal)

C57BL/6JJcl mice (8 weeks old male and 8 weeks old female mice) were introduced from CLEA Japan, Inc. Tumor-bearing model mice were produced as follows. The cell line A431 from human epithelioid cell carcinoma was cultured in DMEM Low Glucose (Sigma)+10% Fetal Bovine Serum (FBS)+Penicillin (100 units/mL)+Streptomycin (100 ug/mL). Approximately 100,000 cells were implanted in the back of nude mouse, Balbc-nu/nu (5 weeks old male mice). After about 10 days, the tumor diameters were reached about 1 cm, then the mice were subjected to the experiments.

Approximately 0.2 mL of the complex of the present invention (siRNA-8 to siRNA-17) dissolved in saline (OTSUKA NORMAL SALINE, Otsuka Pharmaceutical Factory, Inc.), or siRNA without lipid (siRNA-18) or siRNA which has an only linker bound to the second strand (siRNA-21) as a comparative example was administered intravenously to each mouse at a dose of 50 mg/kg or 25 mg/kg. Three days after administration to male mice, approximately 0.5 mL of whole blood and tissue of liver, kidney, lung, spleen, fat, muscle, small intestine, large intestine, testis, bone, bone marrow, thymus, respiratory tract, skin, dorsal root ganglia, spinal cord and brain were collected under isoflurane anesthesia. Three days after administration to female mice, uteri and ovaries were collected under isoflurane anesthesia. Tumor tissues were collected from the tumor-bearing model mice 3 days after administration. The RNAs were extracted according to the manufacturer's recommended protocols using RNeasy 96 Universal Tissue Kit (Qiagen) from the collected tissues and QIAamp RNA Blood Mini Kit (Qiagen) from the blood cells comprising whole blood. Quantitative PCR was performed with One Step SYBR PrimeScript PLUS RT-PCR Kit (Takara) using 20 ng (dorsal root ganglion and blood cells) or 100 ng (the other tissues) of the obtained RNAs. Gapdh was used as an endogenous control. The primer sequences for measuring the level of mouse Hprt1 and mouse Gapdh are the same as Experiment 2.

The results are shown in Tables 19 to 21 (Dose: 50 mg/kg) and Tables 22 and 23 (Dose: 25 mg/kg). In the tables, the ratios of the amount of Hprt1 mRNA normalized with Gapdh compared to the saline group were shown as the knockdown efficiency.

TABLE 19

| siRNA | % mRNA (Liver) | % mRNA (Heart) | % mRNA (Muscle) |
|---|---|---|---|
| siRNA-18 | 86 | 86 | 102 |
| siRNA-21 | 59 | 75 | 74 |
| siRNA-8 | 20 | 35 | 39 |
| siRNA-9 | 12 | 30 | 34 |
| siRNA-10 | 10 | 25 | 27 |
| siRNA-11 | 9 | 21 | 17 |
| siRNA-12 | 7 | 23 | 24 |
| siRNA-13 | 7 | 29 | 27 |
| siRNA-14 | 8 | 29 | 59 |
| siRNA-15 | 7 | 30 | 72 |
| siRNA-16 | 8 | 31 | 78 |
| siRNA-17 | 12 | 21 | 28 |

TABLE 20

| siRNA | % mRNA (Liver) |
|---|---|
| siRNA-22 | 8 |
| siRNA-24 | 6 |
| siRNA-25 | 6 |
| siRNA-26 | 6 |
| siRNA-27 | 7 |
| siRNA-28 | 8 |
| siRNA-29 | 11 |
| siRNA-30 | 7 |
| siRNA-31 | 5 |
| siRNA-32 | 7 |
| siRNA-33 | 8 |
| siRNA-34 | 5 |
| siRNA-35 | 7 |
| siRNA-42 | 6 |
| siRNA-43 | 6 |
| siRNA-76 | 9 |
| siRNA-90 | 9 |
| siRNA-91 | 10 |
| siRNA-95 | 11 |
| siRNA-93 | 9 |
| siRNA-101 | 130 |

TABLE 21

| siRNA | % mRNA (Muscle) |
|---|---|
| siRNA-22 | 44 |
| siRNA-25 | 39 |
| siRNA-26 | 35 |
| siRNA-27 | 24 |
| siRNA-28 | 29 |
| siRNA-29 | 39 |
| siRNA-30 | 35 |
| siRNA-31 | 19 |
| siRNA-32 | 30 |
| siRNA-33 | 34 |
| siRNA-34 | 34 |
| siRNA-35 | 27 |
| siRNA-42 | 23 |
| siRNA-76 | 24 |
| siRNA-90 | 55 |
| siRNA-95 | 21 |
| siRNA-101 | 100 |

TABLE 22

| siRNA | % mRNA (Liver) |
| --- | --- |
| siRNA-36 | 13 |
| siRNA-37 | 9 |
| siRNA-39 | 10 |
| siRNA-40 | 12 |
| siRNA-41 | 14 |
| siRNA-44 | 10 |
| siRNA-45 | 10 |
| siRNA-46 | 11 |
| siRNA-47 | 11 |
| siRNA-48 | 12 |
| siRNA-49 | 14 |
| siRNA-50 | 22 |
| siRNA-51 | 13 |
| siRNA-52 | 13 |
| siRNA-53 | 33 |
| siRNA-63 | 12 |
| siRNA-79 | 15 |
| siRNA-80 | 12 |
| siRNA-81 | 10 |
| siRNA-82 | 15 |
| siRNA-83 | 13 |
| siRNA-86 | 11 |
| siRNA-87 | 13 |
| siRNA-88 | 30 |
| siRNA-89 | 15 |
| siRNA-54 | 13 |
| siRNA-57 | 15 |
| siRNA-58 | 18 |
| siRNA-59 | 11 |
| siRNA-60 | 13 |
| siRNA-61 | 15 |
| siRNA-92 | 9 |

TABLE 23

| siRNA | % mRNA (Muscle) |
| --- | --- |
| siRNA-36 | 33 |
| siRNA-37 | 33 |
| siRNA-39 | 35 |
| siRNA-41 | 33 |
| siRNA-44 | 31 |
| siRNA-45 | 44 |
| siRNA-46 | 42 |
| siRNA-47 | 37 |
| siRNA-49 | 48 |
| siRNA-50 | 46 |
| siRNA-51 | 38 |
| siRNA-52 | 31 |
| siRNA-63 | 38 |
| siRNA-79 | 40 |
| siRNA-80 | 42 |
| siRNA-81 | 43 |
| siRNA-82 | 36 |
| siRNA-83 | 36 |
| siRNA-86 | 31 |
| siRNA-87 | 43 |
| siRNA-88 | 42 |
| siRNA-89 | 33 |
| siRNA-54 | 36 |
| siRNA-57 | 48 |
| siRNA-59 | 39 |
| siRNA-61 | 30 |
| siRNA-92 | 35 |
| siRNA-93 | 26 |

As a result, the complexes of the present invention whose lipid were bound at the 3'-end of the second strand showed activity with higher efficiency not only in liver but also in skeletal muscle, heart and fat compared to the comparative example without lipid (siRNA-18) and the comparative example with the eight-branched lipid (siRNA-101). About 40% knockdown was also observed in lung, spleen, small intestine, large intestine, bone, ovary, uterus, and tumor.

For example, because of "the ability to knock down with high efficiently in skeletal muscle" of the above results, it is thought that the complex of the present invention comprising a nucleic acid medicine with activity against diseases with muscle lesions, particularly diseases such as muscular dystrophy, myotonic dystrophy, myopathy, amyotrophic lateral sclerosis, age-related amyotrophy, cancerous amotorism, spinal muscular atrophy, myasthenia gravis, Guillain Valley's syndrome and polymyositis, can deliver the nucleic acid medicine and exert effects on skeletal muscle. Therefore, the complexes of the present invention are very useful.

Example 4: Evaluation of Lipolytic Enzyme Resistant 20 nmol of the complex of the present invention (siRNA-11), and siRNA without lipid (siRNA-18) or the compound described in Patent Document 8 (siRNA-19 and siRNA-20) as a comparative example were reacted with 0.27 units of phospholipase A2 (Wako Pure Chemical Industries, Ltd.) in 10 1l1 of a reaction buffer. 10 mM Tris HCl, 10 mM $CaCl_2$) and 150 mM NaCl$_2$ (pH 8.5) were used as the reaction buffer. Samples were taken 5, 15 and 60 minutes after the initiation of the reactions, and the free fatty acid concentrations (uM) in the solutions were measured with NEFA measuring kit Wako (Wako Pure Chemical Industries, Ltd.).

The results are shown in Table 24.

TABLE 24

| siRNA | 0 min | 5 min | 15 min | 60 min |
| --- | --- | --- | --- | --- |
| siRNA-20 | 0 | 14.9 | 14.2 | 8.8 |
| siRNA-19 | 0 | 332.3 | 428.1 | 854.3 |
| siRNA-18 | 0 | 1.8 | 4.9 | 0 |
| siRNA-11 | 0 | 2.6 | 0 | 0 |

The release of fatty acids by phospholipase A2 was not detected for siRNA-18 or siRNA-20, which is a siRNA without lipid. For siRNA-19, which is siRNA with phosphatidylethanolamine, fatty acids were degraded over time and released. On the other hand, for the complex of the present invention whose lipid was bound at the 3'-end of the second strand (siRNA-11), fatty acids were not released. Based on the above results, it is thought that the complexes of the present invention have resistant to degradation by many lipolytic enzymes in vivo, and this is one of the reasons why the nucleic acid medicines comprised in the complex of the present invention can exhibit a highly efficient knockdown effect in vivo.

INDUSTRIAL APPLICABILITY

As the above examples, the complexes of the present invention show excellent knockdown activity. In addition, they are resistant to degradation by lipolytic enzymes and suggested to have metabolic stability. Therefore, the activity of a nucleic acid medicine in vivo can be improved by comprising the nucleic acid medicine in the complex of the present invention.

The invention claimed is:

1. A complex, comprising:
an oligonucleotide having suppressing activity of a target gene expression;
a linker; and
a lipid binding through the linker to the oligonucleotide and comprising a group of formula

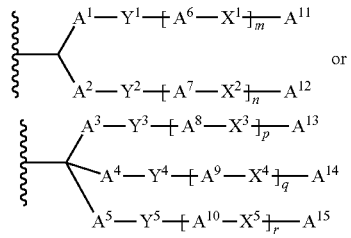

wherein
$A^{11}$ is substituted or unsubstituted alkyl, substituted or unsubstituted alkenyl, substituted or unsubstituted alkynyl or a group of formula:

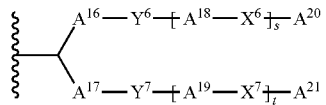

$A^1$ to $A^{10}$ and $A^{16}$ to $A^{17}$ are each independently a bond, substituted or unsubstituted alkylene, substituted or unsubstituted alkenylene, or substituted or unsubstituted alkynylene,
when $A^1$ and $A^2$ or $A^{16}$ and $A^{17}$ are substituted or unsubstituted alkylene, substituted or unsubstituted alkenylene, or substituted or unsubstituted alkynylene, any carbon atom of $A^1$ and any carbon atom of $A^2$, or any carbon atom of $A^{16}$ and any carbon atom of $A^{17}$ taken together may form substituted aromatic carbocycle or substituted non-aromatic carbocycle, $Y^1$ to $Y^7$ are each independently a bond or O, $X^1$, $X^3$ and $X^6$ are each independently $NR^1C(=O)$, $C(=O)NR^1$, $R^2C(=O)NR^1$ or $NR^1C(=O)R^2$,
$X^2$, $X^4$, $X^5$ and $X^7$ are each independently a bond, $NR^3C(=O)$, $C(=O)NR^3$, $R^4C(=O)NR^3$, $NR^3C(=O)R^4$ or S—S,
$R^2$ and $R^4$ are each independently O or $NR^5$,
$R^1$, $R^3$ and $R^5$ are each independently hydrogen, substituted or unsubstituted alkyl, substituted or unsubstituted alkenyl, or substituted or unsubstituted alkynyl,
$A^{12}$ and $A^{14}$ are substituted or unsubstituted alkyl, substituted or unsubstituted alkenyl, substituted or unsubstituted alkynyl, or a group comprising a fat-soluble compound,
$A^{13}$, $A^{15}$, $A^{20}$ and $A^{21}$ are each independently substituted or unsubstituted alkyl, substituted or unsubstituted alkenyl, or substituted or unsubstituted alkynyl, and
m, n, p, q, r, s and t are each independently 1 or 2,
provided that a substituent for the alkyls, alkenyls, alkynyls, alkylenes, alkenylenes and alkynylenes is halogen, hydroxy, carboxy, amino, imino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureide, amidino, guanidino, trialkylsilyl, aromatic carbocyclyl, non-aromatic carbocyclyl, non-aromatic heterocyclyl, non-aromatic heterocyclyl, aromatic carbocyclylcarbonyl, non-aromatic carbocyclylcarbonyl, aromatic heterocyclylcarbonyl or non-aromatic heterocyclylcarbonyl, and the substituent is unsubstituted or comprises one or more substituents selected from Group α consisting of hydroxy, alkyl, alkyloxy, mercapto, alkylthio, amino, alkylamino and halogen, and
wherein the linker is a group of formula

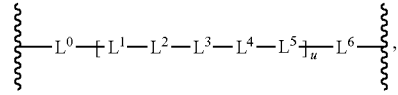

wherein
L⁰ binds to the oligonucleotide and L⁶ binds to the lipid,
L⁰ is a bond, a nucleotide linker or a non-nucleotide linker, and
L¹ is a group of formula

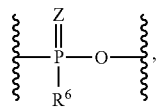

wherein
Z are each independently O or S,
R⁶ are each independently hydroxy, alkyl or alkyloxy,
L² and L⁴ are each independently a bond or substituted or unsubstituted C1 to C20 alkylene,
L³ are each independently C(=O)NR⁷, NR⁸C(=O), or S—S, wherein R⁷ is hydrogen or substituted or unsubstituted alkyl and R⁸ is hydrogen, substituted or unsubstituted alkyl or R⁸ and a carbon atom in alkylene of L² taken together may form substituted or unsubstituted nitrogen-containing ring,
L⁵ are each independently a bond, substituted or unsubstituted C1 to C20 alkylene, C(=O)NR⁹, NR⁹C(=O), NR⁹, O, or substituted or unsubstituted non-aromatic heterocyclyl,
R⁹ is each independently hydrogen, substituted or unsubstituted alkyl, substituted or unsubstituted alkenyl, or substituted or unsubstituted alkynyl,
u is 1 or 2, and
L⁶ is a bond or an amino acid linker.

2. The complex of claim 1, wherein, in the lipid,
A¹ to A⁵ and Y¹ to Y⁵ are a bond,
A⁶ to A¹⁰ are each independently a bond, substituted or unsubstituted alkylene, substituted or unsubstituted alkenylene, or substituted or unsubstituted alkynylene,
X¹ to X⁵ are NHC(=O), and
n, p, q and r are 1.

3. The complex of claim 1, wherein A¹¹ and A¹³ are C6 to C30 alkyl.

4. The complex of claim 1, wherein the lipid binds at the 3'-end and/or 5'-end of the oligonucleotide.

5. A complex of one of formulas (C-2) to (C-7)

(C-2)

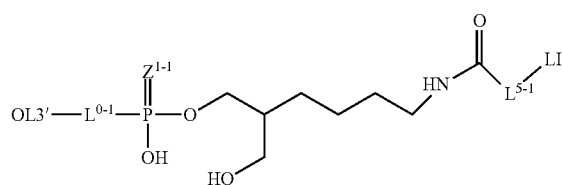

(C-3)

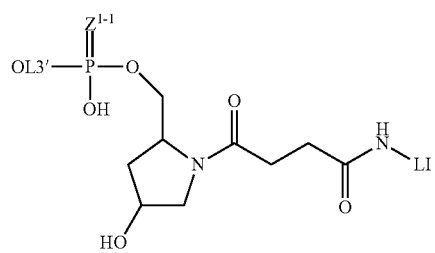

(C-4)

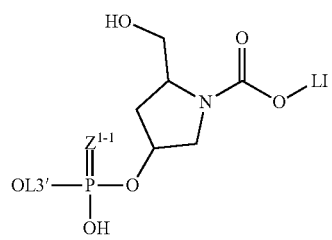

(C-5)

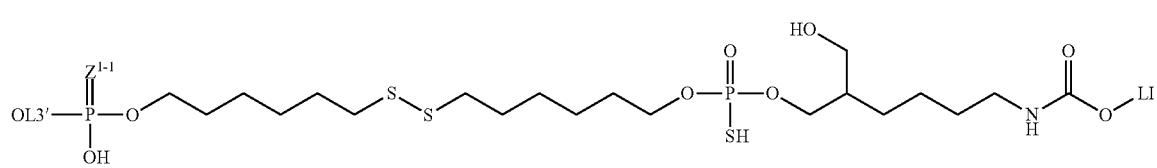

(C-6)

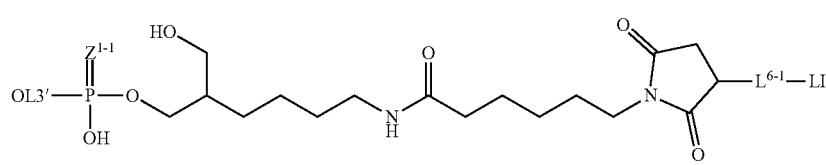

-continued (C-7)
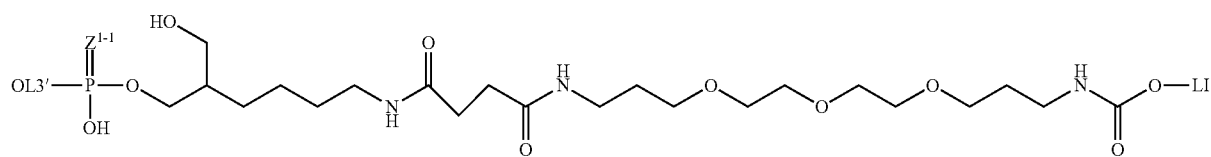

wherein

OL is an oligonucleotide having suppressing activity of a target gene expression, 5' represents that the oligonucleotide binds at the 5'-end of the oligonucleotide, 3' represents that the oligonucleotide binds at the 3'-end of the oligonucleotide, $Z^{1-1}$ is O or S, $L^{0-1}$ is a bond, a nucleotide linker or a non-nucleotide linker, $L^{5-1}$ is a bond, NH or O, $L^{6-1}$ is a bond or an amino acid linker, LI is a lipid comprising a group of one of formulas (LI-1) to (LI-9)

(LI-1)
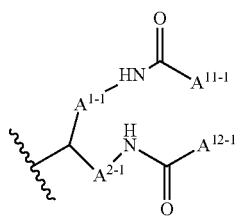

wherein $A^{1-1}$ is a bond or methylene, $A^{2-1}$ is C1 to C4 straight alkylene, $A^{11-1}$ is C7 to C23 straight or branched alkyl, and $A^{12-1}$ is C3 to C23 straight or branched alkyl or alkenyl, a group comprising a fat-soluble compound, or a group of formula

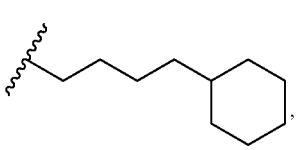

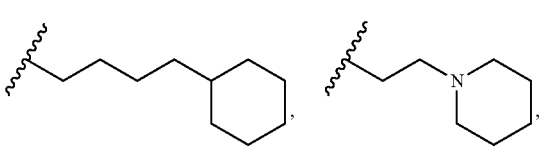

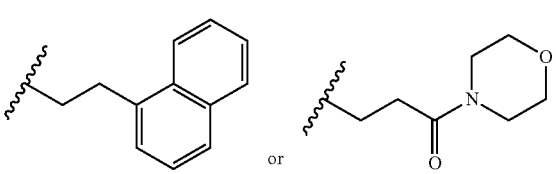 or (LI-2)
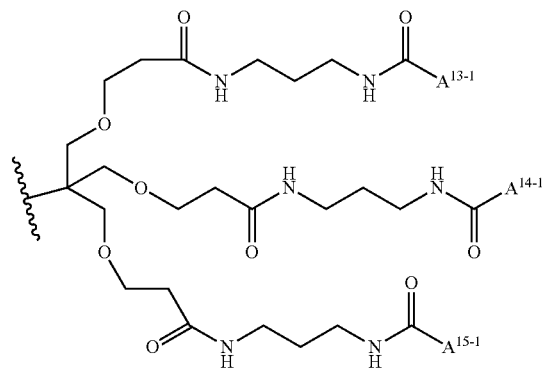

wherein $A^{13-1}$, $A^{14-1}$ and $A^{15-1}$ are C9 to C13 straight alkyl, (LI-3)
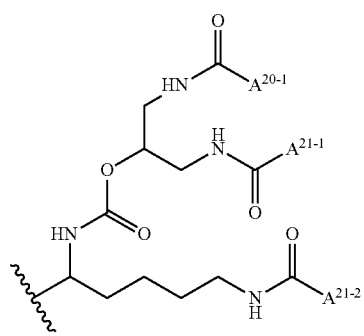

wherein $A^{20-1}$ and $A^{21-1}$ is C13 straight alkyl, and $A^{12-2}$ is C15 straight alkyl or a group comprising a fat-soluble compound, (LI-4)
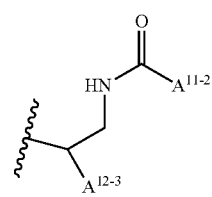

wherein
$A^{11-2}$ is C15 straight alkyl, and
$A^{12-3}$ is C1 to C4 straight alkyl substituted with amino,
wherein
$A^{20-2}$ and $A^{21-2}$ are C13 straight alkyl, and
$A^{12-4}$ is C4 straight alkyl substituted with amino,
(LI-5)
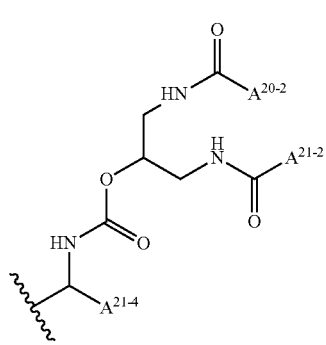
(LI-6)
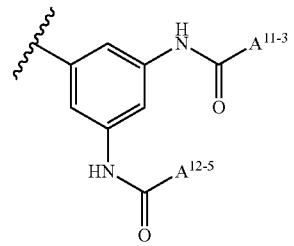
wherein $A^{11-3}$ and $A^{12-5}$ are C15 straight alkyl,
(LI-7)
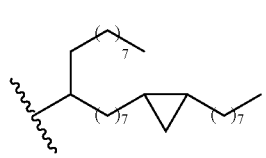
(LI-8)
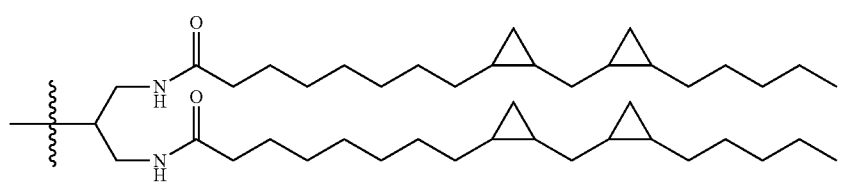
(LI-9)
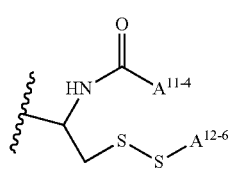

wherein $A^{11-4}$ is C14 straight alkyl, and $A^{12-6}$ is C6 to C12 straight alkyl.

6. A pharmaceutical composition, comprising: the complex of claim 1.

7. The complex of claim 2, wherein $A^{11}$ and $A^{13}$ are C6 to C30 alkyl.

8. The complex of claim 2, wherein the lipid binds at the 3'-end and/or 5'-end of the oligonucleotide.

9. The complex of claim 3, wherein the lipid binds at the 3'-end and/or 5'-end of the oligonucleotide.

10. A pharmaceutical composition, comprising: the complex of claim 2.

11. A pharmaceutical composition, comprising: the complex of claim 3.

12. A pharmaceutical composition, comprising: the complex of claim 4.

13. A pharmaceutical composition, comprising: the complex of claim 5.

14. The complex of claim 7, wherein the lipid binds at the 3'-end and/or 5'-end of the oligonucleotide.

15. The complex of claim 1, wherein the lipid binds at the 3'-end and 5'-end of the oligonucleotide.

16. The complex of claim 1, wherein the lipid binds at the 3'-end of the oligonucleotide.

17. The complex of claim 1, wherein the lipid binds at the 5'-end of the oligonucleotide.

18. A pharmaceutical composition, comprising: the complex of claim 15.

19. A pharmaceutical composition, comprising: the complex of claim 16.

20. A pharmaceutical composition, comprising: the complex of claim 17.

* * * * *